(12) United States Patent
Saab et al.

(10) Patent No.: US 8,394,056 B2
(45) Date of Patent: Mar. 12, 2013

(54) APPARATUS AND METHODS FOR BONE, TISSUE AND DUCT DILATATION

(76) Inventors: Mark A. Saab, Lowell, MA (US);
Michael D. Barbere, Dunstable, MA (US)

( * ) Notice: Subject to any disclaimer, the term of this patent is extended or adjusted under 35 U.S.C. 154(b) by 0 days.

(21) Appl. No.: 13/199,083

(22) Filed: Aug. 18, 2011

(65) Prior Publication Data

US 2012/0053611 A1 Mar. 1, 2012

Related U.S. Application Data

(62) Division of application No. 12/322,825, filed on Feb. 6, 2009, now Pat. No. 8,216,182, which is a division of application No. 10/674,031, filed on Sep. 29, 2003, now Pat. No. 7,488,337.

(60) Provisional application No. 60/414,766, filed on Sep. 30, 2002.

(51) Int. Cl.
*A61M 31/00* (2006.01)
*A61M 29/00* (2006.01)

(52) U.S. Cl. ........... 604/103.08; 604/96.01; 604/500; 604/103.14; 606/192

(58) Field of Classification Search ........... 604/96.01, 604/103.07, 103.08, 103.13, 103.14; 606/192
See application file for complete search history.

(56) References Cited

U.S. PATENT DOCUMENTS

| | | | | |
|---|---|---|---|---|
| 624,811 A * | 5/1899 | Hunt et al. | 212/81 |
| 3,779,239 A * | 12/1973 | Fischer et al. | 606/63 |
| 4,406,656 A * | 9/1983 | Hattler et al. | 604/523 |
| 4,969,888 A * | 11/1990 | Scholten et al. | 606/94 |
| 5,108,404 A * | 4/1992 | Scholten et al. | 606/94 |
| 5,163,989 A * | 11/1992 | Campbell et al. | 65/110 |
| 5,290,306 A * | 3/1994 | Trotta et al. | 606/194 |
| 5,295,994 A * | 3/1994 | Bonutti | 606/192 |
| 5,331,975 A * | 7/1994 | Bonutti | 128/898 |
| 5,342,301 A * | 8/1994 | Saab | 604/103.13 |
| 5,352,199 A * | 10/1994 | Tower | 604/103.07 |
| 5,361,752 A * | 11/1994 | Moll et al. | 600/205 |
| 5,411,477 A * | 5/1995 | Saab | 604/103.13 |
| 5,499,973 A * | 3/1996 | Saab | 604/96.01 |
| 5,569,195 A * | 10/1996 | Saab | 604/103.13 |
| 5,624,392 A * | 4/1997 | Saab | 604/43 |
| 5,741,282 A * | 4/1998 | Anspach et al. | 606/151 |
| 5,766,151 A * | 6/1998 | Valley et al. | 604/103.07 |
| 5,772,681 A * | 6/1998 | Leoni | 606/192 |
| 5,795,325 A * | 8/1998 | Valley et al. | 604/509 |
| 5,827,289 A * | 10/1998 | Reiley et al. | 606/86 R |
| 5,972,015 A * | 10/1999 | Scribner et al. | 606/192 |
| 6,048,346 A * | 4/2000 | Reiley et al. | 606/92 |
| 6,066,154 A * | 5/2000 | Reiley et al. | 606/192 |
| 6,235,043 B1 * | 5/2001 | Reiley et al. | 606/192 |
| 6,241,734 B1 * | 6/2001 | Scribner et al. | 606/93 |
| 6,383,190 B1 * | 5/2002 | Preissman | 606/94 |
| 6,528,446 B1 * | 3/2003 | Stensrud | 501/148 |
| 6,607,544 B1 * | 8/2003 | Boucher et al. | 606/192 |
| 6,613,054 B2 * | 9/2003 | Scribner et al. | 606/93 |
| 6,719,773 B1 * | 4/2004 | Boucher et al. | 606/192 |
| 6,780,183 B2 * | 8/2004 | Jimenez et al. | 606/41 |
| 6,979,341 B2 * | 12/2005 | Scribner et al. | 606/192 |
| 2001/0007938 A1 * | 7/2001 | Long | 606/41 |
| 2002/0156482 A1 * | 10/2002 | Scribner et al. | 606/92 |
| 2002/0161373 A1 * | 10/2002 | Osorio et al. | 606/86 |
| 2002/0183778 A1 * | 12/2002 | Reiley et al. | 606/192 |
| 2003/0050702 A1 * | 3/2003 | Berger | 623/17.12 |

* cited by examiner

*Primary Examiner* — Victoria P Shumate
(74) *Attorney, Agent, or Firm* — David Silverstein

(57) ABSTRACT

Apparatus and methods are disclosed for medical treatment comprising bone, tissue or duct dilatation using inflatable dilatation elements together with apparatus and techniques for tensioning, stretching, folding, and/or wrapping the dilatation elements externally as well as in situ to facilitate insertion, positioning and withdrawal procedures.

30 Claims, 42 Drawing Sheets

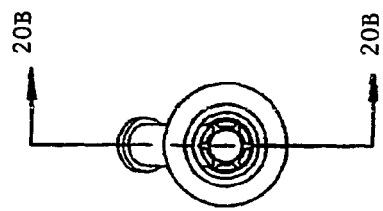
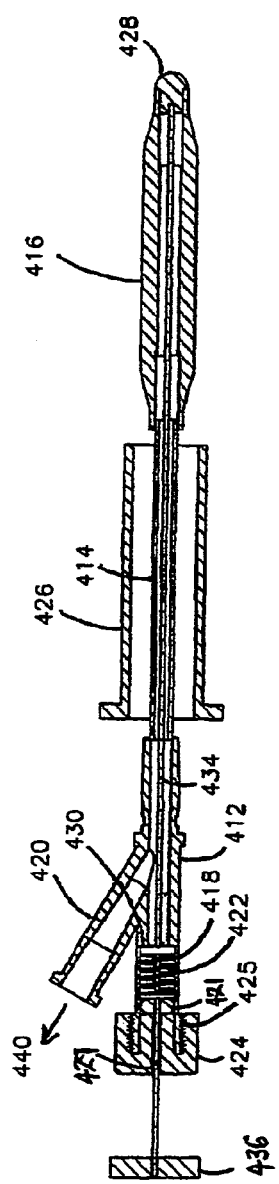
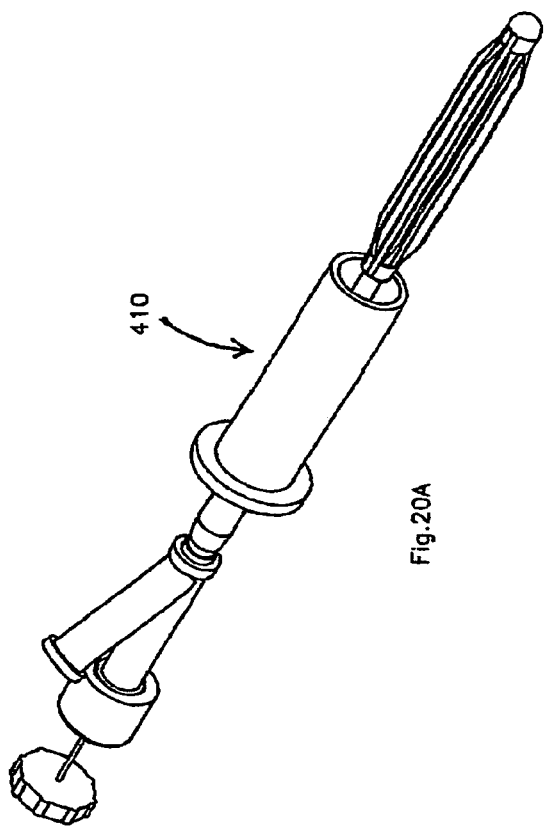

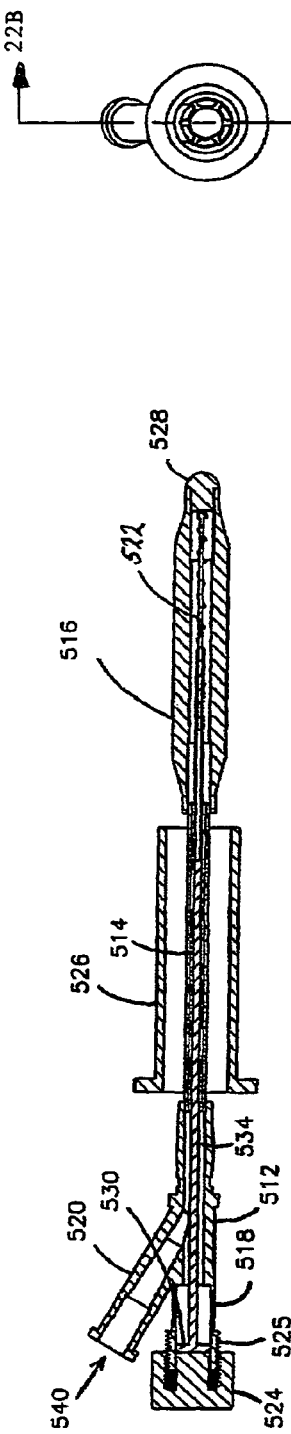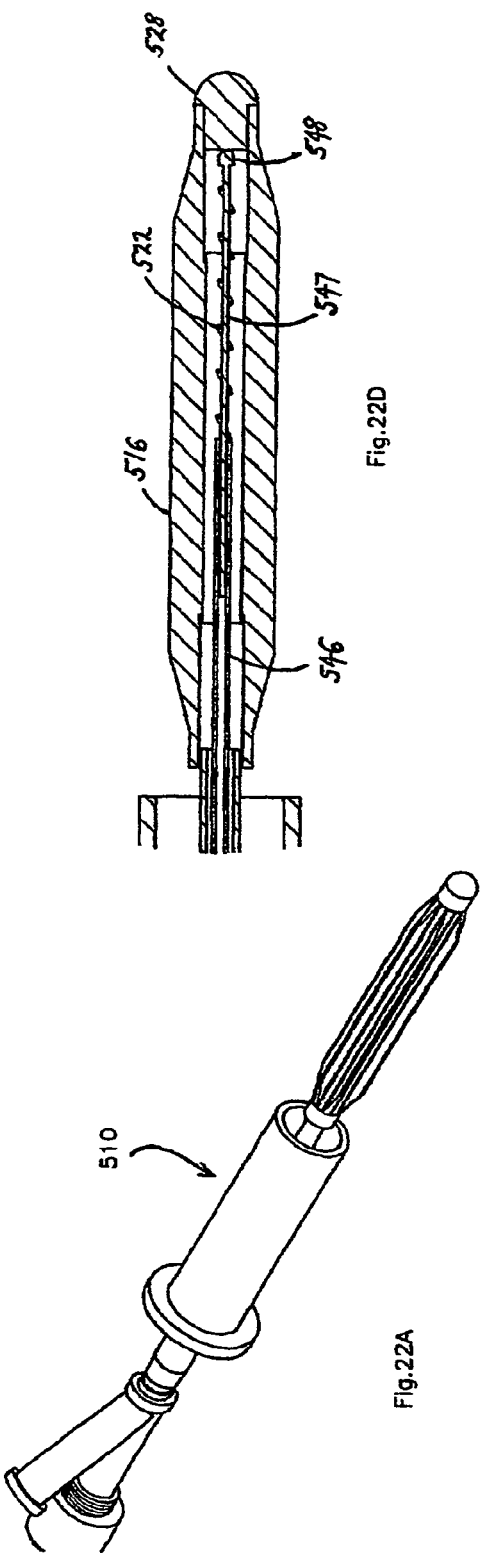

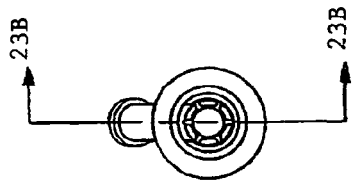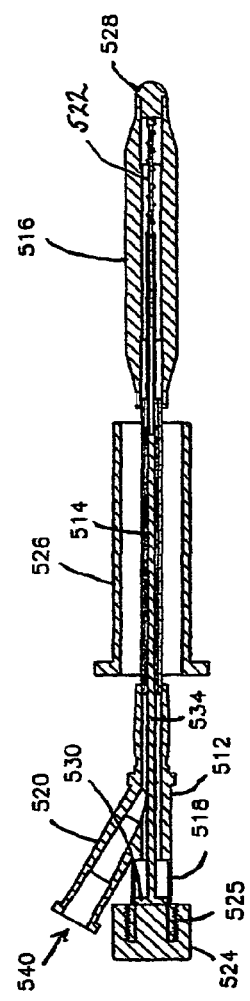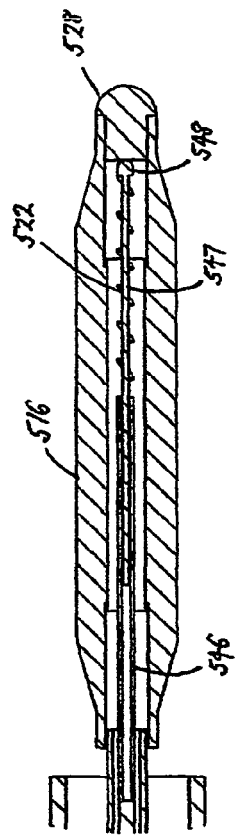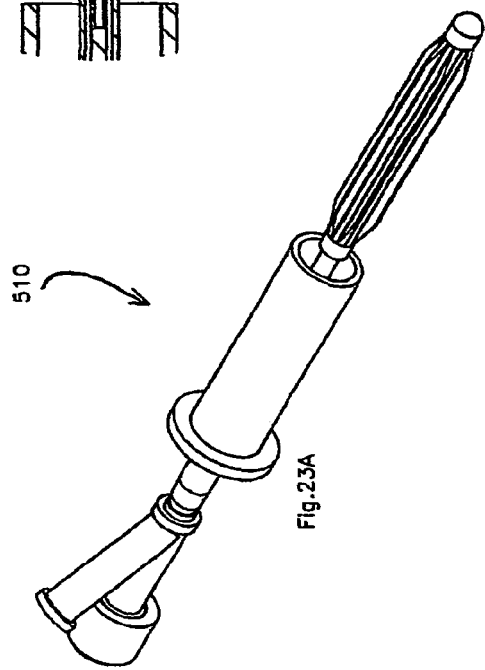

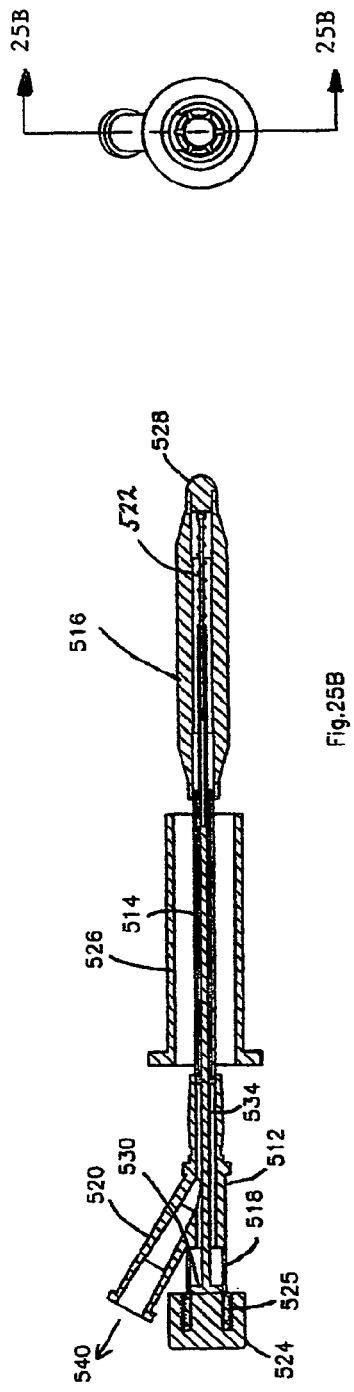
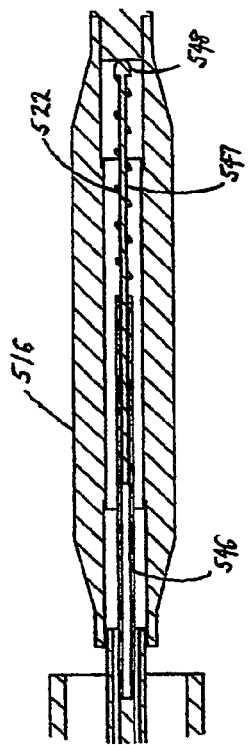
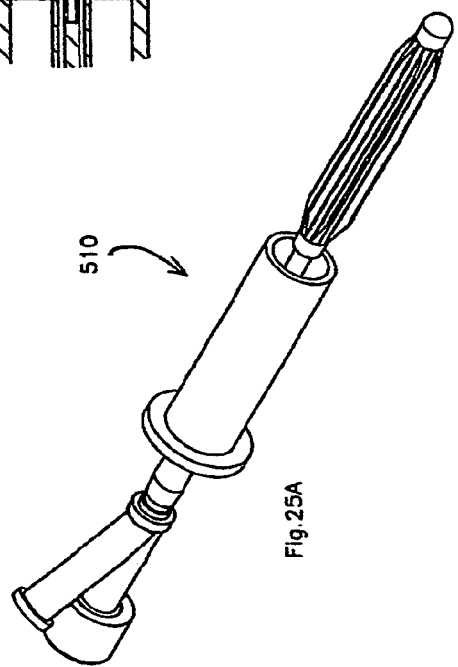
Fig.25C
Fig.25B
Fig.25D
Fig.25A

APPARATUS AND METHODS FOR BONE, TISSUE AND DUCT DILATATION

CROSS-REFERENCE TO RELATED APPLICATIONS

This application is a Division of U.S. Ser. No. 12/322,825, filed Feb. 6, 2009 (now pending), which is a Division of U.S. Ser. No. 10/674,031, filed Sep. 29, 2003, now U.S. Pat. No. 7,488,337 issued Feb. 10, 2009, which claims the benefit of the filing date of U.S. Provisional application Ser. No. 60/414,766, filed Sep. 30, 2002. The complete contents of these earlier applications are incorporated herein by reference.

FIELD OF THE INVENTION

The present invention relates generally to methods and apparatus for bone, tissue and duct dilatation, for example in surgically treating bone deformities and bones suffering from or predisposed to fracture or to collapse, particularly spinal fractures such as those commonly resulting from osteoporosis. In the example of bone treatment, an inflatable balloon element in accordance with the present invention is inserted into an interior region, cavity or passage of a damaged, collapsed, or deformed bone segment; and, thereafter the balloon element is inflated to form, enlarge or support the interior bone region thereby to effect a desirable realignment of the damaged bone segment with adjacent bone portions. In alternative embodiments of this invention, following the dilatation step, the balloon element may be collapsed and withdrawn from the interior bone region utilizing the special methods and apparatus of this invention or, in some embodiments, the dilated balloon element may be left in place, and the cavity or the interior of the dilated balloon element may be filled with a suitable support material. The present invention has particular application in, but is not limited to, treatment of vertebral body compression fractures.

BACKGROUND OF THE INVENTION

A number of diseases, illnesses and other medical conditions are treatable at least in part by dilatation of a bone, tissue or duct. For example, medical conditions and/or physical injuries can lead to or predispose a bone to deformity, such as a fracture. A familiar example is osteoporosis, in which bones lose calcium and break more easily. The human spinal column, comprised of interconnected vertebrae or vertebral bodies, has proven to be especially susceptible to the effects of osteoporosis. A vertebral body weakened by osteoporosis can fracture from a fall, or simply during routine activities. When a vertebral body fractures, it can collapse and change the shape of the spine. The damaged portion of the spine becomes shorter, and the rest of the spine above the broken vertebral body bends forward. As additional vertebral fractures occur, the spine shortens further, increasingly forcing the individual into a hunched-over posture.

As taught by U.S. Pat. No. 6,066,154 (Reiley et al.), which is incorporated herein by reference, it is known in the art to use an inflatable balloon-like device to treat certain bone conditions, resulting from osteoporosis, avascular necrosis, bone cancer and the like, that predispose a bone to, or lead to, fracture or collapse. A particularly common application is in the treatment of vertebral body compression fractures resulting from osteoporosis.

Typical treatment of such conditions includes a series of steps which a surgeon or health care provider can perform to form a cavity in an interior region of pathological bone, including but not limited to osteoporotic bone, osteoporotic fractured metaphyseal and epiphyseal bone, osteoporotic vertebral bodies, fractured osteoporotic vertebral bodies, fractures of vertebral bodies due to tumors especially round cell tumors, avascular necrosis of the epiphyses of long bones, especially avascular necrosis of the proximal femur, distal femur and proximal humerus and defects arising from endocrine conditions.

The method typically further includes the steps of making an incision in the skin (usually one incision, but a second small incision may also be required if a suction egress is used) followed by the placement of a guide pin which is passed through the soft tissue down to and into the bone.

The method of the Reiley '154 patent further includes the steps of drilling the bone to be treated to form a cavity or passage in the bone, following which an inflatable balloon-like device is inserted into the cavity or passage where it is inflated. The inflation of the inflatable device causes a compacting of the cancellous bone and bone marrow against the inner surface of the cortical wall of the bone to further enlarge the cavity or passage. The inflatable device is then deflated and then is completely removed from the bone. The art further teaches that a smaller inflatable device (a starter balloon) can be used initially, if needed, to initiate the compacting of the bone marrow and to commence the formation of the cavity or passage in the cancellous bone and marrow. After this has occurred, a larger, inflatable device can be inserted into the cavity or passage to further compact the bone marrow in all directions.

At this point in accordance with Reiley '154, a flowable biocompatible filling material, such as methylmethacrylate cement or a synthetic bone substitute, is directed into the bone cavity or passage that has been formed and enlarged, and the filling material is allowed to set to a hardened condition to provide ongoing structural support for the bone. Following this latter step, the insertion instruments are removed from the body and the incision in the skin is covered with a bandage.

A related U.S. Pat. No. 6,048,346 (Reiley et al.), which is also incorporated herein by reference, teaches an improved mechanical bone cement injection assembly, which is described as constituting an improvement over prior art devices that operated "similar to a household caulking gun" in that it facilitates greater control over the placement of cement and other flowable liquids into an interior region of a bone.

Another inflatable apparatus intended for deployment into interior body regions is described in U.S. Pat. No. 5,972,015 (Scribner et al.), which is also incorporated herein by reference. The Scribner '015 patent describes a catheter tube extending along a first axis in conjunction with an expandable structure having an expanded geometry oriented about a second axis, not aligned with the first axis, so as to treat an asymmetrically-shaped interior body region or where the access channel cannot be aligned with the body region to be treated. A particular application of this technology is stated to be for the fixation of fractures or other osteoporotic and non-osteoporotic conditions of human and animal bones, specifically for treating a human lumbar vertebra.

Two somewhat earlier patents describing similar apparatus and methods for treating vertebral body compression fractures and the like using an inflatable balloon-like element inserted into the bone cavity are U.S. Pat. Nos. 5,108,404 (Scholten et al.) and 4,969,888 (Scholten et al.), both of which are also incorporated herein by reference.

Numerous problems remain, however, with the prior art apparatuses and methods. For successful expansion of a fractured vertebral body, an expandable element inserted into the vertebral cavity must be capable of being inflated to a relatively large working diameter of about 12 mm-25 mm, starting with a relatively short balloon working length, e.g., about 12 mm-25 mm, sized to fit inside the vertebral cavity, at very high working pressures on the order of 200-400 psi or higher. It has been found that the use of lower inflation pressure in such applications results in only a partial, incomplete expansion of the fractured vertebral body. When that partially-expanded vertebral body is subsequently filled with cement or comparable material, which then hardens, there is a permanent remaining spinal deformity at that vertebral body. Not only must the expandable/inflatable element in the vertebral cavity be capable of inflation to very high pressure without potentially disastrous rupture in order to fully expand a collapsed/fractured vertebral body, in addition the inflated element must resist puncture by hard, sharp cancellous bone and surface irregularities around the outer edges of the vertebral cavity. Standard materials commonly used in the prior art for constructing the expandable, balloon-like element used to expand bone cavities cannot be safely inflated to very high pressures on the order of 200-400 psi or higher, and, when inflated, typically do not have a high degree of puncture resistance.

One possible approach to improve the strength of the balloon-like elements to make them better able to withstand very high inflation pressures would be to use thicker balloon walls and/or to make these elements out of stiffer, stronger materials. There are several reasons, however, why these seemingly straightforward solutions have not proven successful in practice. One is the need to limit the balloon wall thickness and the need to maintain balloon wall flexibility to facilitate access to, and withdrawal from, a bone cavity.

In treating a vertebral fracture, for example, the vertebral cavity is typically accessed by drilling a small hole and locating a short, hollow, metallic tubular element (canula) through the left or right pedicle portion (or sometimes both) of the vertebral arch (see, e.g., FIG. 2 of U.S. Pat. No. 5,972,015, which shows the left and right pedicle portions 42 of vertebral arch 40, and FIG. 6 of the same patent which shows an access hole for catheter tube 50 and expandable structure 56 through one pedicle portion 42 into the interior volume 30 of reticulated cancellous, or spongy, bone 32). Because pedicle portion 42 shown in FIGS. 2 and 6 of the Scribner '015 patent is relatively small and is itself readily susceptible to fracture if its structural integrity is impaired by too large a hole, it is crucial to keep the diameter of the hole, therefore also of the canula, to a minimum, typically no larger than about 4-5 mm. The canula helps to protect surrounding bone portions from abrasion and from expansion forces while inserting or removing the catheter shaft or while inflating the balloon element.

Thus, conventional practice has been to fold or wrap the balloon-like element relatively tightly around the end of a catheter shaft in order to keep the maximum diameter of the unit at the balloon end small enough to fit through the canula of a small-diameter pedicle hole. If a balloon-like expandable element was fabricated having relatively thick walls and/or made from a relatively stiff, less flexible material, such an element might well be inflatable to a higher pressure, but it generally could not be wound tightly enough about the distal end of a catheter shaft to fit through a narrow-diameter pedicle hole.

Even assuming that it were possible somehow to wrap a relatively thick-walled and/or stiff balloon element sufficiently tightly to facilitate insertion of the device through a narrow-diameter pedicle hole, it then would be virtually impossible using prior art technology to remove or withdraw the balloon element through the same hole or canula following dilatation. The reason is that, after a cycle of inflation and deflation inside the vertebral cavity, a thick-walled/relatively inflexible balloon element cannot be refolded or rewrapped in-situ to a sufficiently small diameter to be capable of being withdrawn through the canula without the use of excessive force which might crack or break the pedicle.

In another example, a balloon catheter according to the present invention can be used to treat congenital obstructions of the nasal lacrimal duct. This procedure requires inserting an inflatable element at the distal end of a catheter through the very narrow and sensitive lacrimal duct, inflating the balloon to compress the obstruction and open the passageway, deflating the balloon, and thereafter removing the deflated balloon element through the lacrimal duct. Following inflation, however, the balloon element may not return to its pre-inflation profile making withdrawal difficult.

These and other deficiencies in and limitations of the prior art approaches to treating bone deformities, such as vertebral body compression fractures, and other medical treatments involving inserting, inflating, and thereafter deflating and removing a balloon element through a relatively narrow body passageway are largely if not completely overcome with the apparatus and methods of this invention for bone, tissue and duct dilatation.

OBJECTS OF THE INVENTION

Accordingly, a general object of the present invention is to provide improved apparatus and methods for bone, tissue and duct dilatation.

Another general object of the present invention is to provide improved inflatable balloon-like elements for dilatation of interior bone regions, tissue portions, or duct segments in combination with balloon withdrawal systems and methods of using the same.

Still another general object of the present invention is to provide inflatable balloon-like elements able to expand to relatively large diameters, to withstand relatively high inflation pressures, and to resist damage by hard, sharp cancellous bone for use in dilating an interior region of a damaged bone.

A specific object of the present invention is to provide apparatus and methods for more effectively treating vertebral body compression fractures.

Another specific object of the present invention is to provide apparatus and methods for removing congenital obstructions of the nasal lacrimal duct.

Another specific object of the present invention is to provide inflatable balloon-like elements for dilatation of an interior region of a damaged bone capable of expansion to inflated working diameters of about 12 mm-25 mm, starting with relatively short balloon working lengths sized to fit inside a vertebral or other bone or body cavity, at working pressures of about 200-400 psi or higher.

Still another specific object of the present invention is to provide inflatable balloon structures, capable of inflation to high working pressures, which are relatively easily introduced into the interior region of a bone, tissue or duct through a small diameter opening, on the order of about 4 to about 5 mm or less in diameter or width, and which balloon structures are capable of being collapsed to a very small diameter following inflation to facilitate withdrawal after use.

Yet another specific object of the present invention is to provide active or passive balloon wrapping or tensioning assemblies, or both for use in conjunction with inflatable balloon structures according to the present invention to facilitate insertion of a balloon structure through a narrow diameter opening or passageway and/or withdrawal of a balloon structure through a narrow diameter opening or passageway following an inflation-deflation cycle.

Another specific object of the present invention is to provide assemblies comprising in combination an inflatable balloon element, a catheter shaft connected to the balloon element to provide a working fluid for inflating the balloon element and for withdrawing the fluid to deflate the balloon element, and at least a balloon tensioning and/or wrapping device or both for stretching the balloon element and/or folding, pleating or wrapping the balloon element to facilitate insertion and/or removal of the balloon element through a narrow diameter duct, access channel or canula typically having an opening of about 4 to 5 mm or less.

Other objects and advantages of the present invention will in part be obvious and will in part appear hereinafter. The invention accordingly comprises, but is not limited to, the apparatus and related methods, involving the several steps and the various components, and the relation and order of one or more such steps and components with respect to each of the others, as exemplified by the following description and the accompanying drawings. Various modifications of and variations on the apparatus and methods as herein described will be apparent to those skilled in the art, and all such modifications and variations are considered within the scope of the invention.

SUMMARY OF THE INVENTION

The present invention provides for the fabrication, deployment, inflation, deflation and withdrawal of very high-pressure, puncture- and abrasion-resistant balloon catheters that are capable of being relatively easily introduced and withdrawn through a hole or canula in the pedicle of a spine, or through the lacrimal duct, and in similar body treatment applications. In other embodiments of the present invention, the balloons, expansion elements, and balloon catheters described herein function to increase the surface area of dilation in order to more readily compress cancellus or other bone matter thereby to expand a vertebral or other bone element, to compress or remove a lacrimal duct obstruction, and in similar medical treatment applications.

Balloon catheter designs described herein provide for either active or passive axial tension on the balloon or expansion element, or an assembly for wrapping the balloon element, or both. Tension and/or wrapping may be needed for both insertion and withdrawal, but has been found to be primarily needed for in-situ tensioning/wrapping prior to withdrawal where one does not have the benefit of being able to wrap the balloon down with one's fingers as is commonly done prior to insertion.

In accordance with the present invention, a balloon or expansion element may be mounted on the distal end of a hollow tube which may be either metal or plastic. These devices need not be flexible/bendable as is common with standard balloon catheters because the devices of the present invention typically are not intended to be snaked through the tortuous path of a blood vessel. The proximal end of the balloon is bonded to or integrally connected with the tube at or near the distal end of the tube to create a fluid passage through the tube to the interior of the balloon element. The distal end of the balloon can be configured in several different ways.

In one embodiment, the distal end of the balloon is sealed off either by integral manufacturing of a sealed end balloon, for example in accordance with U.S. Pat. No. 5,411,477, which is incorporated herein by reference, or by sealing or potting the distal balloon neck. This end is left unattached and an axially-oriented push rod is used to push against the sealed end of the balloon causing tension and axial elongation or movement of the balloon during deflation, which causes the balloon to form a number of longitudinal pleats or folds which substantially reduces the profile of the deflated balloon allowing it to be more easily withdrawn. The fact that the distal end is not attached makes this embodiment easier to manufacture and reduces the chance of a leak point by eliminating a glue or bond joint.

In an alternative embodiment, the distal end of the balloon can be attached to the push rod by adhesive or thermal bonding if desired. The push rod can be rotated and pushed to produce an even tighter re-wrap of the balloon. Both active and passive rotation of the push rod can be used.

The push rod can be spring loaded anywhere along the shaft, preferably at the back (proximal) end of the catheter inside a suitable manifold where the force, distance and other important parameters can be easily controlled, permanently set, or be made adjustable by the device user. The force can be active or passive, it can be adjusted so that there is always an axial load on the balloon or only a load when the balloon is inflated and deflated. Once the balloon is stretched a predetermined amount the tension is released. The removal of constant tension during sterilization, storage, etc. can be important to prevent creep or weakening of the balloon and at the bond areas. A method of passive tension, but with an active preparation before using it, may be the most desirable approach for many applications.

The push rod itself can be a compressive spring or a spring can be incorporated anywhere along the length of the push rod or machined as part of the rod. Alternatively, the design can be fabricated such that there is no push rod, but the hollow tube has a spring section either attached or integrally formed somewhere along its length inside the balloon, and the balloon is attached to this rod at one or both ends. The tension can also be provided by hydraulic or pneumatic actuation on the back end of the device, or a pneumatic bladder can be inflated in the back.

An adjustable position/tension rod may be preferred in some applications in which the balloon may be inflated to very high pressure beyond its elastic limit where permanent axial and radial deformation may occur. Such deformation would require the catheter design to accommodate this growth to insure that enough tension and axial displacement takes place to fold the balloon down.

In all of these designs, inflation of the balloon will cause the balloon to fill up in diameter while causing the overall length of the balloon to shorten, which will push or compress the shaft. The tension is designed to allow the balloon to fully expand. As the balloon is deflated, the tension in the shaft pushes the distal end in the distal direction and begins folding or collapsing the balloon and may also assist in more rapid deflation of the balloon. In another embodiment, elastomeric tubing can be placed over the balloon to help it refold and to protect the balloon from damage. The balloon can also be coated to help improve its puncture and abrasion resistance.

In still another embodiment of the present invention, a balloon that is longer than the length necessary to fill a bone or similar body cavity can be used, and the canula can be designed so as to restrict any expansion thereby creating an absolute maximal dilation region for each and every application without wasting space for the balloon transitions or requiring multiple length balloons for treating various size vertebral or other bone or body cavities. All that would be necessary is to have available several balloon diameters or a more compliant balloon, but of only one length. In this embodiment, it is also envisioned to size or position the canula such that the distal end may extend partially into the cavity to be dilated so as to further control balloon length and area of dilation.

In still another embodiment, after dilating a balloon or inflation element in accordance with this invention, the rod structure is removed, the balloon is filled with cement or a cement-like material that cures and hardens in situ and left in place as an implant. After removing the canula, the long proximal neck can be cut off to separate the proximal end of the catheter from the filled balloon element. In another variation, a hollow push rod could be left in place during cement filling of the balloon to act as a vent tube, which would be removed after the balloon is full of cement.

In yet another embodiment of this invention, multi-lumen balloon elements, for example as described in my U.S. Pat. Nos. 5,342,301; 5,569,195; and 5,624,392, which are incorporated herein by reference, may be used as the balloon elements for the catheters of this invention.

Other specific embodiments of the present invention include the following:

(1) An assembly adapted for bone, tissue and/or duct dilatation of a living being comprising in combination: a hollow tube; an inflatable and deflatable balloon element having proximal and distal ends in fluid communication with the hollow tube; and, balloon tensioning and/or balloon wrapping device(s) for stretching the balloon element and/or folding, pleating or wrapping the balloon element to facilitate insertion and/or removal of the balloon element through a narrow diameter duct, access channel or cannula.

(2) An assembly according to paragraph (1) above in which said balloon element is capable of being inflated to a working diameter of about 12 mm to about 25 mm.

(3) An assembly according to paragraph (1) above in which said balloon element is capable of being inflated to a working pressure of about 200-400 psi over a relatively short balloon working length.

(4) An assembly according to paragraph (1) above in which said balloon element is stretched and/or folded, pleated or wrapped to a diameter of about 4-5 mm or less for insertion through and/or removal from said duct, access channel or canula.

(5) An assembly according to paragraph (1) above in which said balloon tensioning and/or balloon wrapping device(s) is/are selected from the group consisting of active and passive tensioning and wrapping devices.

(6) An assembly according to paragraph (1) above in which, upon inflation to its working pressure, the balloon element maintains a high degree of puncture and abrasion resistance.

(7) An assembly according to paragraph (1) above in which the balloon element is mounted on the distal end of the hollow tube, and the proximal end of the balloon element is bonded to or integrally connected with an end of the tube to create a passage through the tube to the interior of the balloon element.

(8) An assembly according to paragraph (7) above in which the distal end of the balloon element is sealed, and the assembly further comprises a rod element running through the passage of the tube and the interior of the balloon element to the sealed distal end of the balloon element.

(9) An assembly according to paragraph (8) above in which axial force can be applied manually or automatically to push the rod element against the sealed distal end of the balloon element causing tension and axial elongation of the balloon element.

(10) An assembly according to paragraph (9) above in which the rod element is not attached to the balloon element.

(11) An assembly according to paragraph (9) above in which the rod element is attached to or otherwise engages the balloon element.

(12) An assembly according to paragraph (11) above in which wherein rotational force can be applied manually or automatically to rotate the rod element from its free-standing position causing the balloon element at least in part to wrap around the rod element.

(13) An assembly according to paragraph (9) above in which wherein said rod element is spring loaded to apply axial tensioning and elongation to the balloon element.

(14) An assembly according to paragraph (11) above in which said rod element is spring loaded to apply rotational tensioning to the balloon element.

(15) An assembly according to paragraph (11) above in which said rod element is spring loaded to apply both automatic axial and rotational tensioning to the balloon element.

(16) An assembly according to paragraph (9) above in which said rod element comprises a compressive or rotational spring element.

(17) An assembly according to paragraph (7) above in which said hollow tube comprises a compressive spring element.

(18) An assembly according to paragraph (1) above in which the balloon tensioning and/or wrapping device is hydraulically or pneumatically actuated.

(19) An assembly according to paragraph (8) above in which said rod element is adjustable in length.

(20) An assembly according to paragraph (1) above including elastomeric tubing placed over said balloon element.

(21) An assembly according to paragraph (1) above in which wherein the exterior of said balloon element is coated with a material to improve puncture and abrasion resistance.

(22) An assembly according to paragraph (11) above including at least a cannula element wherein at least one end of the balloon element extends into or completely through said cannula element when the balloon element is positioned in a cavity to be dilated.

(23) An assembly according to paragraph (22) above in which said cannula element is adapted to restrict expansion forces of the balloon element during inflation.

(24) An assembly according to paragraph (8) above in which, after the balloon element is inserted in a cavity to be dilated and inflated to working pressure for a sufficient period of time, the interior of the inflated balloon element is filled in situ with a cement material.

(25) An assembly according to paragraph (24) above in which the rod element is removed before the balloon element is filled with a cement material.

(26) An assembly according to paragraph (24) above in which the rod element has a hollow interior to act as a vent for working fluid while the balloon element is filled with a cement material, and is removed before the cement hardens.

(27) An assembly according to paragraph (24) above in which the hollow tube is detached from the balloon element after the balloon element is filled with the cement material.

(28) An assembly according to paragraph (1) above in which said balloon element comprises a multi-lumen balloon.

(29) An assembly according to paragraph (11) above in which said rod element is spring loaded to apply automatic axial tensioning to the balloon element and is adapted for optional manual rotational tensioning of the balloon element.

(30) An assembly according to paragraph (1) above including a pre-curved guidewire in the interior of the balloon element.

(31) An assembly according to paragraph (8) above in which said rod element comprises concentric inner and outer tubular members which are rotatable relative to one another and said balloon element is attached to or engages one of said tubular members whereby rotational forces can be applied to cause the balloon element at least in part to wrap around one of said tubular members.

(32) An assembly according to paragraph (8) above in which wherein said rod element is pre-curved and consists essentially of a material having memory properties.

(33) An assembly according to paragraph (1) above in which said balloon element is pre-curved.

(34) An assembly according to paragraph (1) above in which said balloon element consists essentially of a non-elastomeric material.

(35) A method for treating a living being for bone, tissue and/or body duct dilatation comprising the sequential steps of: inserting an inflatable balloon element in an uninflated state into an interior region, cavity or passage of a damaged, collapsed or deformed bone, tissue or duct through a first narrow diameter opening or passageway to position the balloon element at a body location requiring dilatation; inflating the balloon element with a working fluid to a working pressure and for a time period sufficient to substantially completely dilate the interior region, cavity or passage to substantially restore its normal size, shape and/or alignment; deflating the balloon element by withdrawing the working fluid; during and/or subsequent to said deflating step, stretching and/or folding, pleating or wrapping the balloon element to reduce its profile; and, withdrawing the previously-inflated balloon element through a narrow diameter opening or passageway, which may be the same as or different than said first narrow diameter opening or passageway.

(36) A method according to paragraph (35) above in which said balloon element is inflated to a working diameter of about 12 mm to about 25 mm during the inflating step.

(37) A method according to paragraph (35) above in which said balloon element is inflated to a working pressure of about 200-400 psi over a relatively short balloon working length during the inflating step.

(38) A method according to paragraph (1) above in which said balloon element is stretched and/or folded, pleated or wrapped to a diameter of about 4-5 mm or less for the steps of inserting and/or withdrawing the balloon element.

(39) A method according to paragraph (35) above in which said balloon element is stretched and/or folded, pleated or wrapped using at least a balloon tensioning and/or balloon wrapping device selected from the group consisting of active and passive tensioning and wrapping devices.

(40) A method according to paragraph (35) above in which, following inflation to its working pressure, the balloon element maintains a high degree of puncture and abrasion resistance.

(41) A method according to paragraph (35) above including the step of applying a vacuum to the inflated balloon element during the deflating step to assist with withdrawal of the working fluid.

(42) A method according to paragraph (35) above in which the balloon element is mounted on the distal end of a hollow tube, and the proximal end of the balloon element is bonded to or integrally connected with an end of the tube to create a passage through the tube to the interior of the balloon element.

(43) A method according to paragraph (42) above in which the distal end of the balloon element is sealed.

(44) A method according to paragraph (43) above in which a rod element passes through the tube and the interior of the balloon element to the sealed end of the balloon element.

(45) A method according to paragraph (44) above including the step of applying axial force manually or automatically to said sealed end of the balloon element through said rod element during and/or subsequent to the deflating step causing tension and axial elongation of the balloon element.

(46) A method according to paragraph (45) above in which the rod element is not attached to the balloon element.

(47) A method according to paragraph (45) above in which the rod element is attached to or otherwise engages the balloon element.

(48) A method according to paragraph (47) above including the step of applying rotational force manually or automatically to said rod element during and/or subsequent to the deflating step causing the balloon element at least in part to wrap around the rod element.

(49) A method according to paragraph (45) above in which said rod element is spring loaded to apply axial tensioning and elongation to the balloon element.

(50) A method according to paragraph (48) above in which said rod element is spring loaded to apply rotational tensioning to the balloon element.

(51) A method according to paragraph (35) above in which the balloon tensioning and/or wrapping device is hydraulically or pneumatically actuated.

(52) A method according to paragraph (44) above in which said rod element is adjustable in length, said method further comprising the step of adjusting the length of said rod element such that said rod element applies an axial tensioning to the balloon element during the deflating step.

(53) A method according to paragraph (35) above including the step of coating the exterior of the balloon element with a coating to improve puncture and abrasion resistance.

(54) A method according to paragraph (35) above in which, upon inserting the balloon element into an interior region, cavity or passage, at least one end of the balloon element extends into or completely through a cannula element positioned in one of the narrow diameter openings or passageways.

(55) A method according to paragraph (35) above in which said balloon element comprises a multi-lumen balloon.

(56) A method according to paragraph (47) above in which said rod element is spring loaded to automatically apply axial tensioning to the balloon element during the deflating step, said method further comprising the step of applying manual rotational tensioning to the balloon element during and/or subsequent to the deflating step.

(57) A method according to paragraph (35) above including the steps of positioning a guidewire through the interior region, cavity or passage to be dilated, and using the guidewire to position the balloon element during the inserting step.

(58) A method according to paragraph (57) above in which said guidewire is pre-curved.

(59) A method according to paragraph (44) above in which said rod element is pre-curved and fabricated from a material having memory properties.

(60) A method according to paragraph (35) above in which said balloon element is pre-curved.

(61) A method according to paragraph (35) above in which said balloon element consists essentially of a non-elastomeric material.

(62) A method for treating a living being for bone or tissue dilatation comprising the sequential steps of: providing a dilatation apparatus able to fit through a narrow opening, said dilatation apparatus comprising an inflatable balloon element in fluid communication with a hollow tube, and a rod element running through the interior of the hollow tube and the inflatable balloon element, wherein said balloon element is uninflated and is wrapped, folded, pleated or stretched at least in part about said rod element to reduce the profile of the balloon portion of the dilatation apparatus; inserting the dilatation apparatus into an interior region, cavity or passage of a damaged, collapsed or deformed bone or tissue region through a first narrow diameter opening or passageway to position the balloon element at a body location requiring dilatation; inflating the balloon element through the hollow tube with a working fluid to a working pressure and for a time period sufficient to substantially completely dilate the interior region, cavity or passage to substantially its normal size, shape and/or alignment; and, filling the inflated balloon element in situ through the hollow tube with a cement material.

(63) A method according to paragraph (62) above including the further steps of removing the rod element before filling the balloon element with cement material and detaching the hollow tube from the balloon element after it is filled with cement.

(64) A method according to paragraph (62) above in which the rod element has a hollow interior which is used for venting working fluid from the balloon element while it is being filled with cement material.

(65) A method according to paragraph (64) above including the steps of removing the rod element and detaching the hollow tube from the balloon element after it is filled with cement.

(66) A method according to paragraph (62) above in which said balloon element is inflated to a working diameter of about 12 mm to about 25 mm during the inflating step.

(67) A method according to paragraph (62) above in which said balloon element is inflated to a working pressure of about 200-400 psi over a relatively short balloon working length during the inflating step.

(68) A method according to paragraph (62) above in which said balloon element is wrapped, folded, stretched and/or pleated about said rod element such that the balloon portion of the dilatation apparatus has a diameter of about 4-5 mm or less for the inserting step.

(69) A method according to paragraph (62) above in which said balloon element comprises a multi-lumen balloon.

(70) A method according to paragraph (62) above including the steps of positioning a guidewire through the interior region, cavity or passage to be dilated, and using the guidewire to position the balloon element during the inserting step.

(71) A method according to paragraph (62) above in which said guidewire is pre-curved.

(72) A method according to paragraph (62) above in which said rod element is pre-curved and fabricated from a material having memory properties.

(73) A method according to paragraph (62) above in which said rod element is pre-curved and fabricated from a material having memory properties.

(74) A method according to paragraph (62) above in which said balloon element consists essentially of a non-elastomeric material.

(75) A method for treating a living being for dilatation of a section of a body duct to relieve a collapse or blockage condition comprising the sequential steps of: providing a dilatation apparatus able to fit through a narrow opening, said dilatation apparatus comprising an inflatable balloon element in fluid communication with a hollow tube, and a rod element running through the interior of the hollow tube and the inflatable balloon element, wherein said balloon element is uninflated and is wrapped, folded, pleated or stretched at least in part about said rod element to reduce the profile of the balloon portion of the dilatation apparatus; inserting the dilatation apparatus into a body duct to be dilated to position the balloon element at a duct section requiring dilatation; inflating the balloon element through the hollow tube with a working fluid to a working pressure and for a time period sufficient to substantially completely dilate the duct section to substantially its normal size; deflating the balloon element by withdrawing the working fluid; during and/or subsequent to said deflating step, stretching and/or folding, pleating or wrapping the balloon element to reduce its profile; and, withdrawing the dilatation apparatus including the previously-inflated balloon element from the treated duct.

(76) A method according to paragraph (75) above in which said balloon element is inflated to a working diameter of about 12 mm to about 25 mm during the inflating step.

(77) A method according to paragraph (75) above in which said balloon element is inflated to a working pressure of about 200-400 psi over a relatively short balloon working length during the inflating step.

(78) A method according to paragraph (75) above in which said balloon element is stretched and/or folded, pleated or wrapped to a diameter of about 4-5 mm or less for the steps of inserting and/or withdrawing the balloon element.

(79) A method according to paragraph (75) above in which said balloon element is stretched and/or folded, pleated or wrapped using at least a balloon tensioning and/or balloon wrapping device selected from the group consisting of active and passive tensioning and wrapping devices.

(80) A method according to paragraph (75) above including the step of applying a vacuum to the inflated balloon element during the deflating step to assist with withdrawal of the working fluid.

(81) A method according to paragraph (75) above in which the distal end of the balloon element is sealed, said method further comprising the step of applying axial force manually or automatically to said sealed end of the balloon element through said rod element during and/or subsequent to the deflating step causing tension and axial elongation of the balloon element.

(82) A method according to paragraph (81) above in which the rod element is not attached to the balloon element.

(83) A method according to paragraph (81) above in which the rod element is attached to or otherwise engages the balloon element.

(84) A method according to paragraph (83) above including the step of applying rotational force manually or automatically to said rod element during and/or subsequent to the deflating step causing the balloon element at least in part to wrap around the rod element.

(85) A method according to paragraph (81) above in which said rod element is spring loaded to apply axial tensioning and elongation to the balloon element.

(86) A method according to paragraph (84) above in which said rod element is spring loaded to apply rotational tensioning to the balloon element.

(87) A method according to paragraph (75) above in which the balloon tensioning and/or wrapping device is hydraulically or pneumatically actuated.

(88) A method according to paragraph (75) above in which said rod element is adjustable in length, said method further comprising the step of adjusting the length of said rod element such that said rod element applies an axial tensioning to the balloon element during the deflating step.

(89) A method according to paragraph (84) above in which said rod element is spring loaded to automatically apply axial tensioning to the balloon element during the deflating step, said method further comprising the step of applying manual rotational tensioning to the balloon element during and/or subsequent to the deflating step.

(90) A method according to paragraph (75) above in which said rod element comprises concentric inner and outer tubular members which are rotatable relative to one another, and said balloon element is attached to or engages one of said tubular members, said method further comprising the step of rotating said tubular members relative to one another during an/or subsequent to the deflating step to cause the balloon element to wrap at least in part around one of said tubular members.

These and other variations and embodiments of the apparatus of this invention, and different applications for and methods of using such apparatus, will be apparent from the drawings and the following description of the drawings.

BRIEF DESCRIPTION OF THE DRAWINGS

In FIG. 1A, the catheter is shown in a neutral position as it would be for shipping and storage prior to use. The cap portion is loose, and there is no compression of the spring element. The balloon element is shown extended, pleated and/or folded for compactness.

In FIG. 5A, the catheter is shown in a neutral position as it would be for shipping and storage prior to use. The cap is loose, the balloon element is prefolded and/or pleated, and, optionally, wrapped around a push rod extending along the longitudinal axis of the device. The sealing gasket is not compressed, and the push rod is in a forward position (toward the distal end of the device). In one variation of this embodiment of the invention, the push rod may be attached to the distal tip of the balloon element or otherwise capable of engaging the balloon element to enable twisting the balloon element to wrap it around the push rod as described further below.

In FIG. 13A, the cap portion is loose, and there is no compression of the spring element.

In FIG. 17A, the catheter is shown in a neutral position as it would be for shipping and storage prior to use. The cap portion is loose, and there is no compression of the spring element. The balloon element is shown extended, pleated and/or folded for compactness.

FIG. 20A is a schematic elevation view of the same apparatus shown in FIGS. 17A, 18A and 19A, except that in FIG. 20A dilatation pressure has been removed and, optionally, a vacuum may be applied to the fluid inlet/outlet conduit to withdraw fluid from the formerly inflated balloon element thereby collapsing it. As the balloon element is deflated, the compressed spring element exerts a force on the disc and rod pushing them axially toward the distal end of the apparatus. This results in stretching and tensioning the balloon element thereby assisting in collapsing, folding and/or pleating the balloon element for easier withdrawal from the dilated bone cavity.

FIG. 20C is an end view of the apparatus of FIG. 20A as seen from the distal end.

FIG. 20B is a cross-sectional view of the device as shown in FIG. 20C taken along line 20B-20B.

FIG. 22A is a schematic elevation view of apparatus according to a sixth embodiment of the present invention designed for automatic tensioning of a balloon element using a spring tensioning system located at the distal (internal) end of the device to facilitate withdrawal through a small diameter canula from a bone cavity following dilatation and subsequent deflation. In FIG. 22A, the catheter is shown in a neutral position as it would be for shipping and storage prior to use. The cap portion is loose, and there is little or no compression of the spring element. The balloon element is shown extended, pleated and/or folded for compactness.

FIG. 22C is an end view of the apparatus of FIG. 22A as seen from the distal end.

FIG. 22B is a cross-sectional view of the device as shown in FIG. 22C taken along line 22B-22B.

FIG. 22D is an enlarged cross-sectional view of the distal end of the device as shown in FIG. 22B to better illustrate details of the spring tensioning system at the balloon end of the apparatus.

FIG. 23A is a schematic elevation view of the same apparatus shown in FIG. 22A, except that in FIG. 23A the cap has been screwed down resulting in at least partially compressing the spring element and applying axial tension to the balloon in preparation for using the device. The balloon element remains extended and folded and/or pleated.

FIG. 23C is an end view of the apparatus of FIG. 23A as seen from the distal end.

FIG. 23B is a cross-sectional view of the device as shown in FIG. 23C taken along line 23B-23B.

FIG. 23D is an enlarged cross-sectional view of the distal end of the device as shown in FIG. 23B to better illustrate details of the spring tensioning system at the balloon end of the apparatus.

FIG. 25A is a schematic elevation view of the same apparatus shown in FIGS. 22A, 23A and 24A, except that in FIG. 25A dilatation pressure has been removed and, optionally, a vacuum may be applied to the fluid inlet/outlet conduit to withdraw fluid from the formerly inflated balloon element thereby collapsing it. As the balloon element is deflated, the compressed spring element exerts a force on the rod pushing it axially toward the distal end of the apparatus. This results in stretching and tensioning the balloon element thereby assisting in collapsing, folding and/or pleating the balloon element for easier withdrawal from the dilated bone cavity.

FIG. 25C is an end view of the apparatus of FIG. 25A as seen from the distal end.

FIG. 25B is a cross-sectional view of the device as shown in FIG. 25C taken along line 25B-25B.

FIG. 25D is an enlarged cross-sectional view of the distal end of the device as shown in FIG. 25B to better illustrate details of the spring tensioning system at the balloon end of the apparatus.

Similar to the embodiments of FIGS. 5-9 and 17-21, the embodiment of FIGS. 22-25 can readily be adapted to add a rod rotation/balloon wrapping capability if the rod is equipped with a rotation-resisting element and the rod engages or can engage the end of the balloon.

FIGS. 26A-26D show schematic cross-sectional views of a vertebral segment with a V-shaped catheter access channel formed through both pedicle portions and the cancellous bone being treated in accordance with one embodiment of the present invention.

FIGS. 27A-27D show schematic cross-sectional views of a vertebral segment with a V-shaped catheter access channel formed through both pedicle portions and the cancellous bone being treated in accordance with another embodiment of the present invention.

FIGS. 28A-28E show schematic cross-sectional views of a vertebral segment with a U-shaped catheter access channel formed through both pedicle portions and the cancellous bone being treated in accordance with still another embodiment of the present invention.

Figure 29:
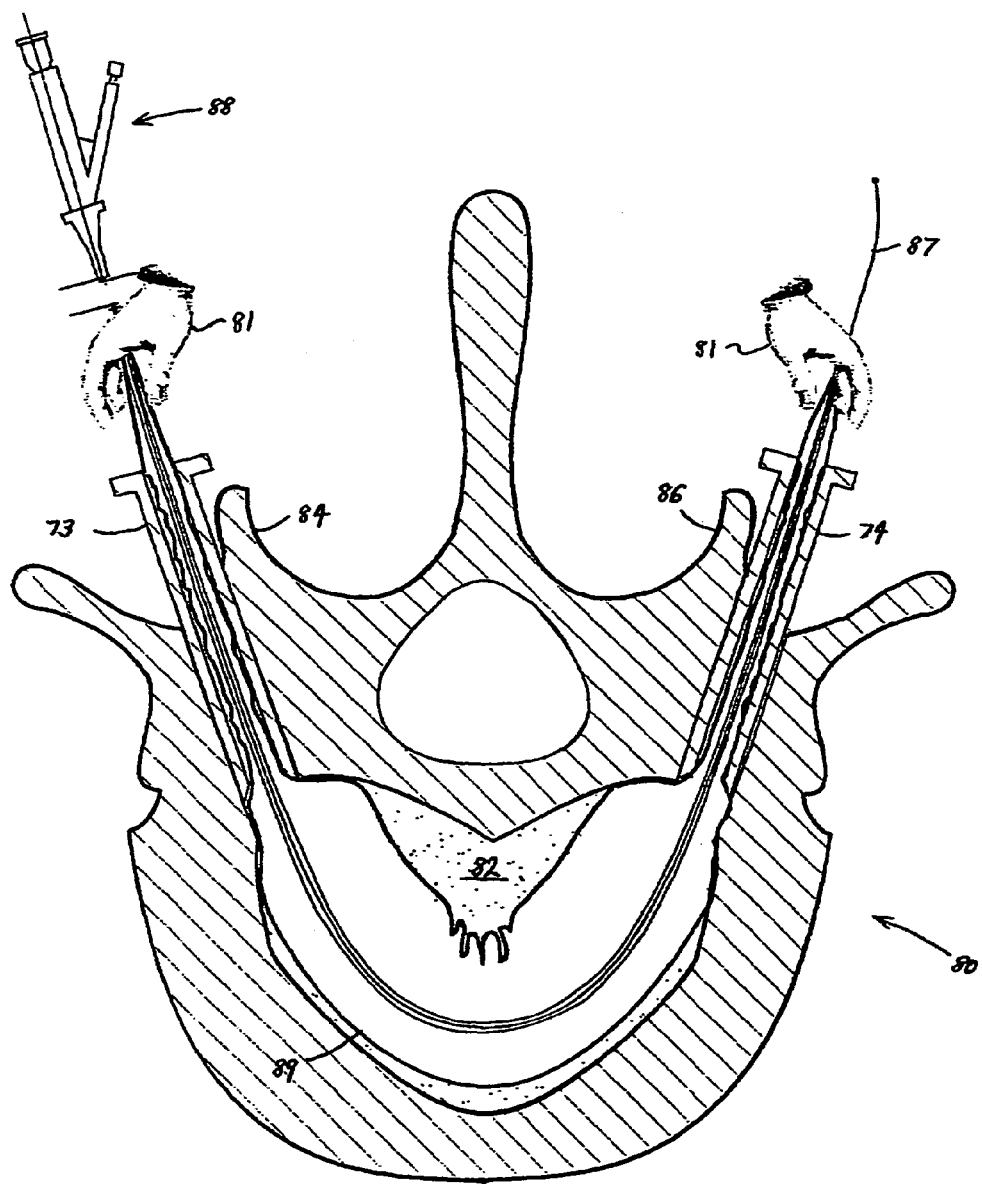

FIG. 29 shows a schematic cross-sectional view of a vertebral segment with a U-shaped catheter access channel formed through both pedicle portions and the cancellous bone being treated in accordance with still another embodiment of the present invention.

Figure 30:
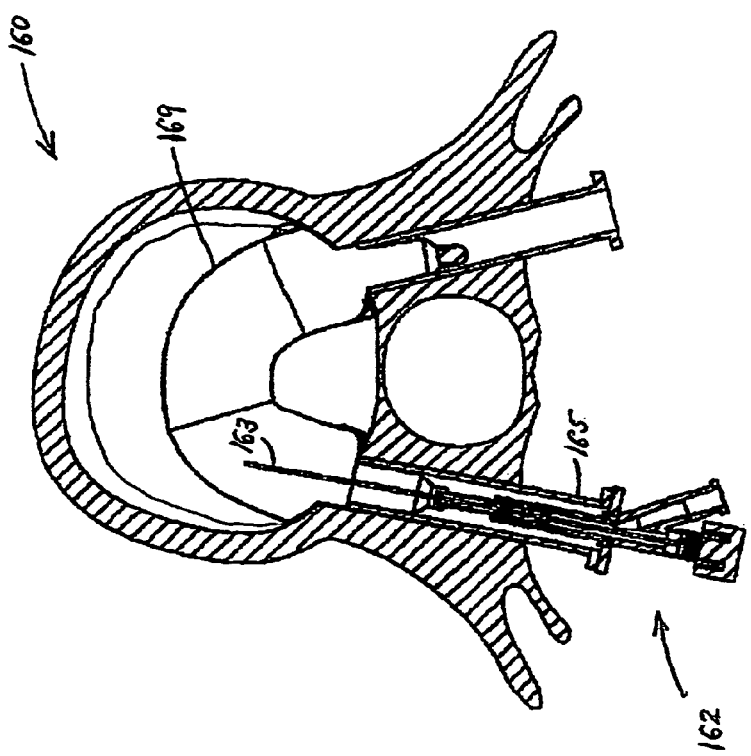

FIG. 30 shows a schematic cross-sectional view of a vertebral segment with a U-shaped catheter access channel formed through both pedicle portions and the cancellous bone being treated with a catheter apparatus using a pre-curved guidewire in accordance with another embodiment of the present invention.

Figure 31:
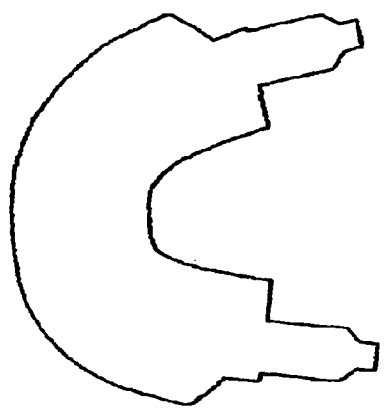

FIG. 31 is a schematic side view of a pre-curved balloon element designed for use in some embodiments of the present invention.

Figure 32:
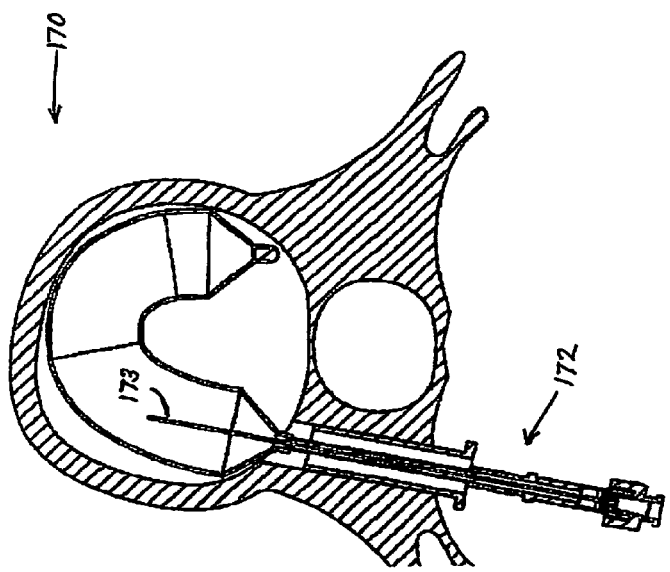

FIG. 32 is a schematic cross-sectional view of a vertebral segment with a catheter access channel formed through only one pedicle portion being treated with a catheter apparatus using a pre-curved guidewire in accordance with another embodiment of the present invention.

Figure 33:
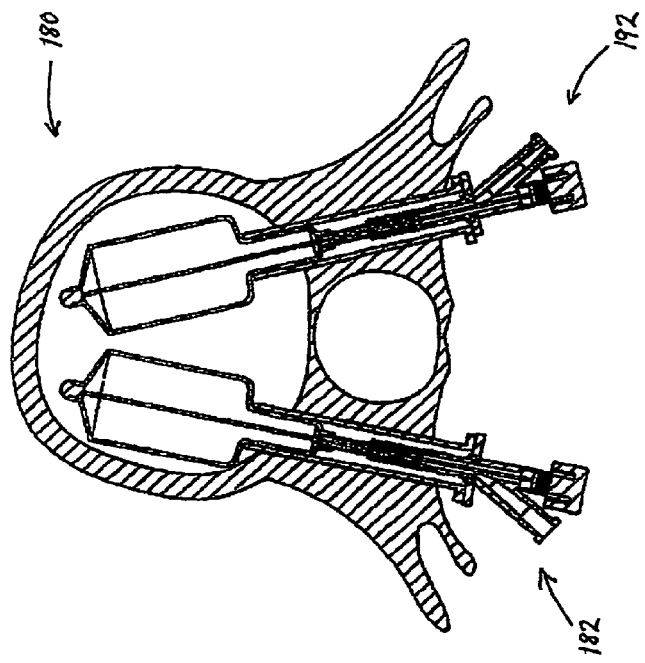

FIG. 33 is a schematic cross-sectional view of a vertebral segment with catheter access channels formed through both pedicle portions for treatment with two catheter apparatuses in accordance with still another embodiment of the present invention.

Figure 34C:
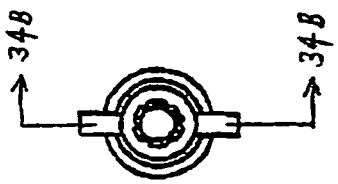
Figure 34B:
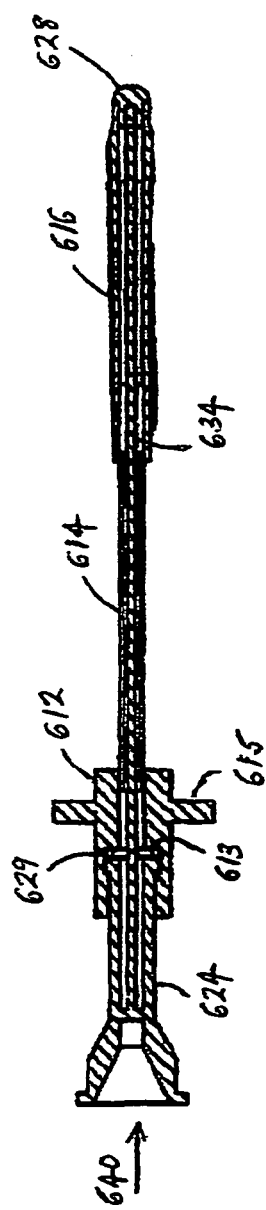
Figure 34A:
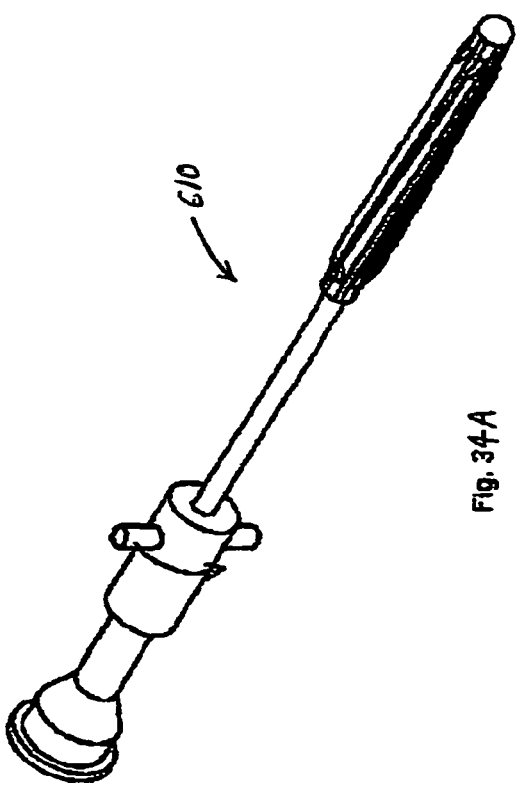

FIG. 34A is a schematic elevation view of apparatus according to still another embodiment of the present invention designed for wrapping a balloon or inflation element to facilitate withdrawal through a small diameter canula from a bone cavity or through a small diameter duct following dilatation and subsequent deflation. The apparatus of FIG. 34A is configured somewhat similar to that shown in FIG. 10A except that in FIG. 34A there is a fixed inner shaft and the balloon is wrapped by rotating the outer shaft. This can be accomplished with or without tensioning of the balloon or inflation element.

FIG. 34C is an end view of the apparatus of FIG. 34A as seen from the distal end.

FIG. 34B is a cross-sectional view of the device as shown in FIG. 34C taken along line 34B-34B.

DETAILED DESCRIPTION OF PREFERRED EMBODIMENTS

FIGS. 1-4 illustrate a dilatation balloon tensioning apparatus according to a first embodiment of the present invention. The balloon dilatation catheter apparatus 10 in FIGS. 1A-1C generally comprises a proximal end catheter sleeve portion 12, a middle sleeve portion 14, and a balloon or inflation element 16 at or near the distal end of the catheter. As best seen in FIG. 1B, proximal end catheter sleeve portion 12 comprises a branched or Y-shaped element, of which one arm or branch 18 comprises a tubular shell with external threads 25 at its proximal end, and the second arm or branch 20 comprises a fluid inlet/outlet conduit for introducing pressurized fluid 40 into catheter 10 for inflating balloon 16 or for withdrawing fluid 40 after a dilatation procedure.

Figure 1C:
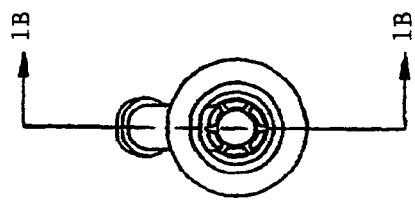
FIG. 1C is an end view of the apparatus of FIG. 1A as seen from the distal end.
Figure 1B:
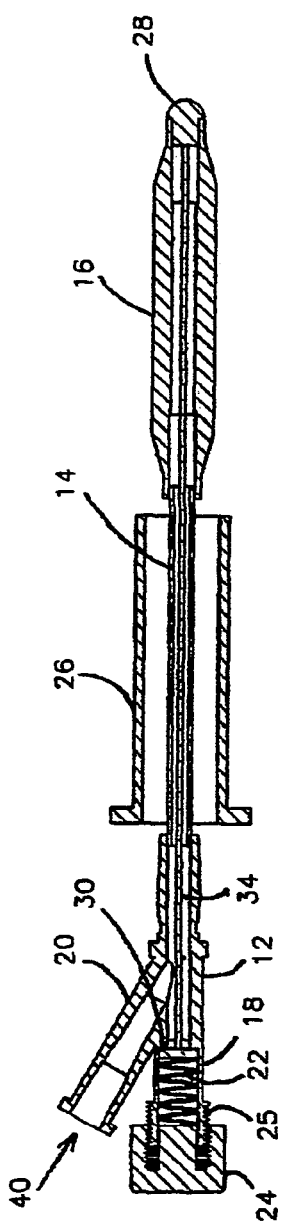
FIG. 1B is a cross-sectional view of the device as shown in FIG. 1C taken along line 1B-1B.
Figure 1A:
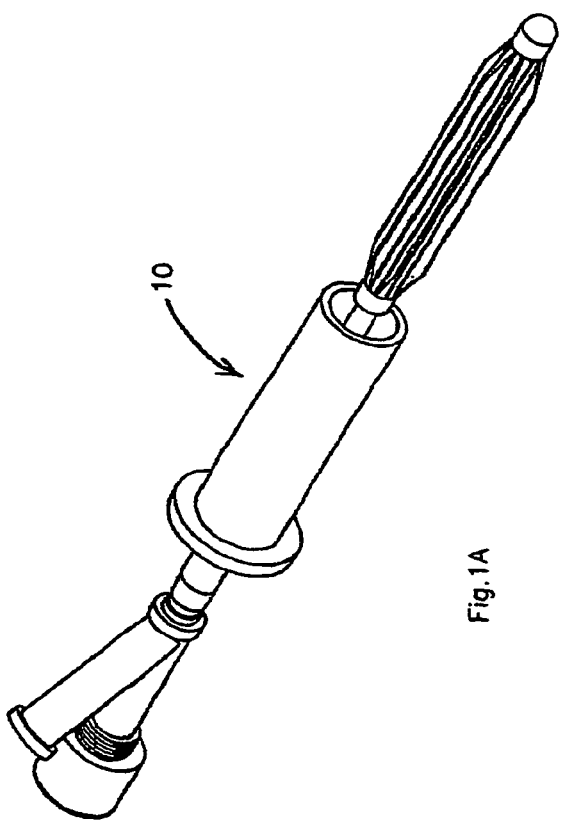
FIG. 1A is a schematic elevation view of apparatus according to a first embodiment of the present invention designed for automatic tensioning of a balloon element using a spring tensioning system located at the proximal (external) end of the device to facilitate withdrawal through a small diameter canula from a bone cavity following dilatation and subsequent deflation.

The tubular shell of branch 18 comprises a region adjacent to the threaded region for housing a spring element 22. Cap element 24 has internal threads and is sized to mate with the external threads 25 at the proximal end of branch 18. As seen in FIGS. 1A-1C, the cap element 24 is loosely threaded onto branch 18, and there is no compression of spring element 22, the condition in which catheter 10 would ordinarily be shipped and stored. Balloon element 16 is shown extended, and, as seen in FIGS. 1A and 1C, is preferably pleated or folded for compactness.

Balloon elements suitable for use with the various catheter designs described herein may be elastomeric or non-elastomeric, depending on the particular application, and may be fabricated from various conventional balloon catheter materials, for example the various catheter and balloon materials taught by U.S. Pat. No. 5,499,973, which is incorporated herein by reference. It is also within the scope of this invention to coat the exterior of the balloon elements to prevent or minimize damage or rupture from sharp bones. It is also within the scope of this invention to cover the balloon elements with elastomeric tubes both to help squeeze and deflate the balloons during deflation and to resist damage from surrounding bone.

At the distal end of the region for housing spring element 22 (i.e., at the end opposite from where the cap 24 is threaded onto branch 18), a disc element or circular fitting 30 is sized to slide inside the region housing spring element 22 so as to compress the spring element by displacement in the proximal direction or to decompress the spring element by displacement in the distal direction. Associated with disc element 30 is axially moveable rod element 34 (which may or may not be physically connected to disc element 30) which runs axially through the interior of the catheter from the distal side of disc element 30 to the sealed tip portion 28 of balloon 16. Rod element 34 may or may not be physically connected to or may or may not engage balloon tip portion 28. Rod element 34 operating in conjunction with disc element 30 thus can act like a piston to alternately compress and allow decompression of spring element 22.

Also shown in FIGS. 1A-1C, although it is typically not attached to catheter apparatus 10, is a small diameter canula 26 which provides a channel for the catheter apparatus through a bone portion into the bone interior. Balloon element 16 must be able to slide through the hollow interior of canula 26 during insertion of the catheter and, more importantly, during removal of the catheter after the balloon has undergone an inflation/deflation cycle.

Figure 2C:
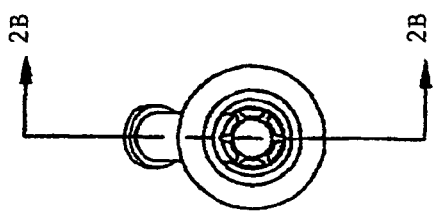
FIG. 2C is an end view of the apparatus of FIG. 2A as seen from the distal end.
Figure 2B:
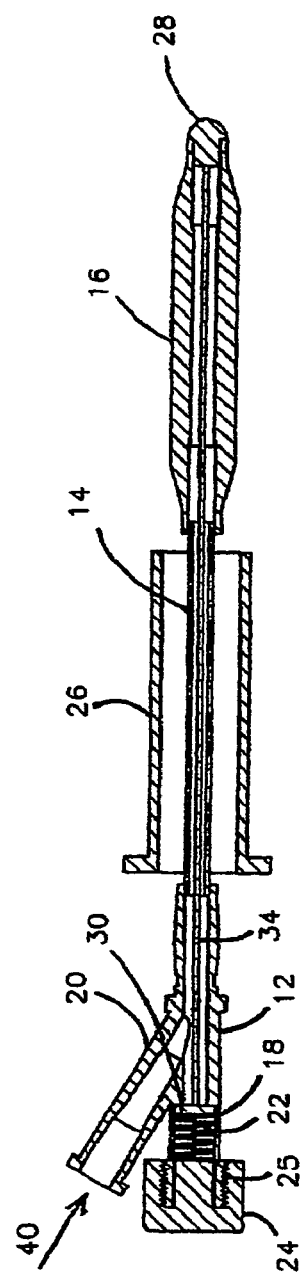
FIG. 2B is a cross-sectional view of the device as shown in FIG. 2C taken along line 2B-2B.
Figure 2A:
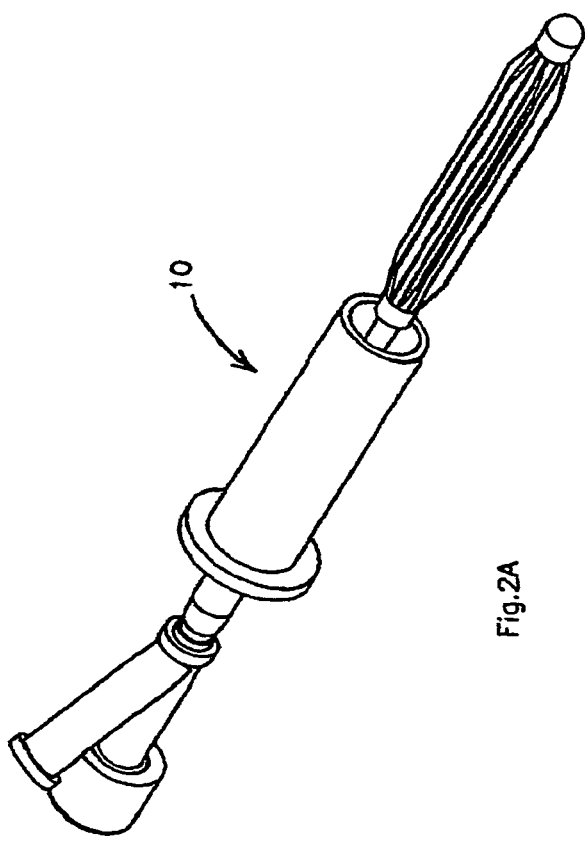
FIG. 2A is a schematic elevation view of the same apparatus shown in FIG. 1A, except that in FIG. 2A the cap has been screwed down resulting in at least partially compressing the spring element in preparation for using the device. The balloon element remains extended and folded and/or pleated.
Figure 3C:
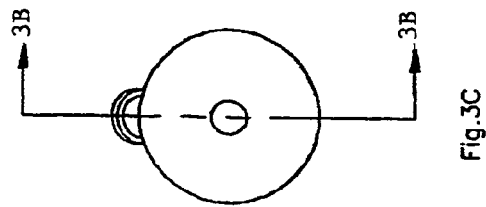
FIG. 3C is an end view of the apparatus of FIG. 3A as seen from the distal end.
Figure 3B:
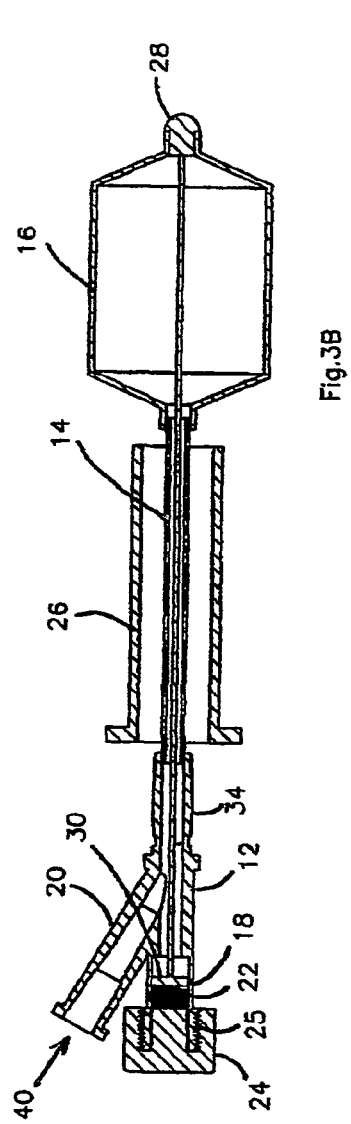
FIG. 3B is a cross-sectional view of the device as shown in FIG. 3C taken along line 3B-3B.
Figure 3A:
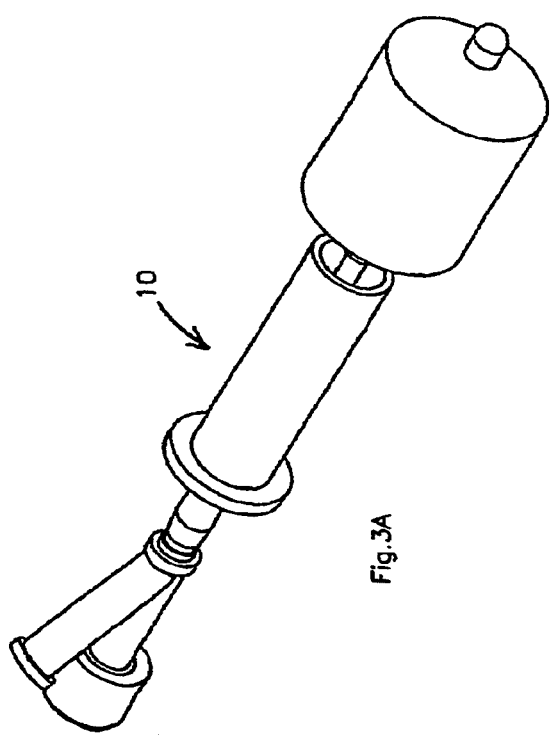
FIG. 3A is a schematic elevation view of the same apparatus shown in FIGS. 1A and 2A, except that in FIG. 3A pressurized fluid has been introduced to fully inflate the balloon element. As a consequence of the balloon being inflated, it expands in diameter and shortens in length causing the rod/disc elements to be displaced toward the proximal end of the apparatus thereby further compressing the spring element.

In FIGS. 2A-2C, catheter apparatus 10 of FIGS. 1A-1C is shown with cap element 24 screwed down resulting in at least partially compressing spring element 22 in preparation for use. In FIGS. 3A-3C, pressurized fluid 40 has been introduced through branch 20, through a part of the interior of proximal sleeve portion 12, and through the interior of middle sleeve portion 14 to fully inflate balloon 16. As balloon 16 is inflated, it expands in diameter and shortens in length causing rod 34 to move in a proximal direction, thereby displacing disc element 30 in a proximal direction and further compressing spring element 22.

Figure 4C:
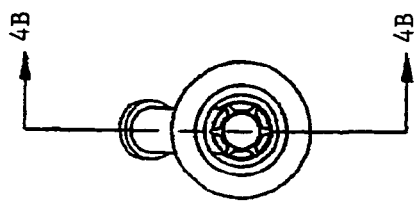
FIG. 4C is an end view of the apparatus of FIG. 4A as seen from the distal end.
Figure 4B:
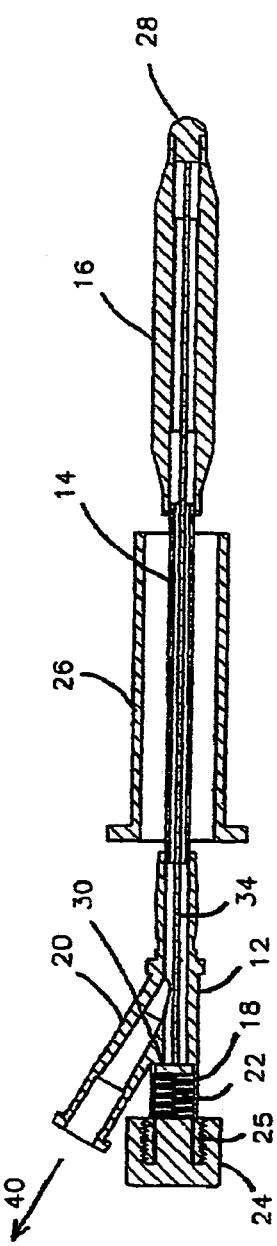
FIG. 4B is a cross-sectional view of the device as shown in FIG. 4C taken along line 4B-4B.
Figure 4A:
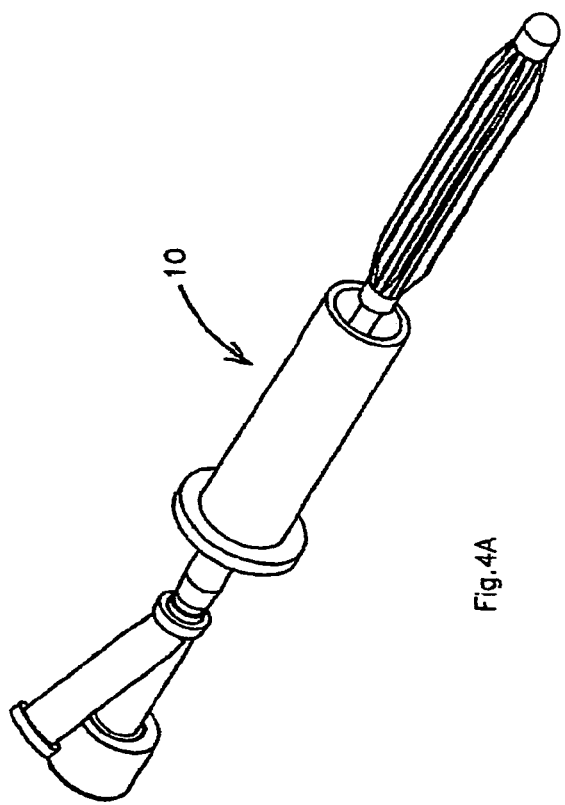
FIG. 4A is a schematic elevation view of the same apparatus shown in FIGS. 1A, 2A and 3A, except that in FIG. 4A dilatation pressure has been removed and, optionally, a vacuum may be applied to the fluid inlet/outlet conduit to withdraw fluid from the formerly inflated balloon element thereby collapsing it. As the balloon element is deflated, the compressed spring element exerts a force on the disc and rod pushing them axially toward the distal end of the apparatus. This results in stretching and tensioning the balloon element thereby assisting in collapsing, folding and/or pleating the balloon element for easier withdrawal from the dilated bone cavity.

In FIGS. 4A-4C, dilatation pressure is removed and fluid is withdrawn from balloon 16 and from the interior of catheter 10 through fluid inlet/outlet branch 20. In a preferred embodiment, a vacuum may be applied to the proximal end of branch 20 to assist in withdrawing fluid and fully collapsing balloon 16. As balloon 16 becomes deflated, the force exerted by the compressed spring element 22 becomes greater than the force exerted by the collapsing balloon. Eventually this results in displacing disc element 30 toward the distal end of the catheter, in turn driving rod 34 in the distal direction, and thereby stretching and tensioning balloon 16. This automatic tensioning of the balloon element upon deflation assists in collapsing, folding and/or pleating the balloon to minimize its lateral profile for easier withdrawal through the small diameter interior channel of canula 26.

FIGS. 5-9 illustrate a dilatation balloon tensioning apparatus according to a second embodiment of the present invention. The balloon dilatation catheter apparatus 110 in FIGS. 5A-5C generally comprises a proximal end catheter sleeve portion 112, a middle sleeve portion 114, and a balloon or inflation element 116 at the distal end of the catheter. As best seen in FIG. 5B, proximal end catheter sleeve portion 112 comprises a branched or Y-shaped element, of which one arm or branch 118 comprises a tubular shell with external threads 125 at its proximal end, and the second arm or branch 120 comprises a fluid inlet/outlet conduit for introducing pressurized fluid 140 into catheter 110 for inflating balloon 116 or for withdrawing fluid 140 after a dilatation procedure.

Figure 5C:
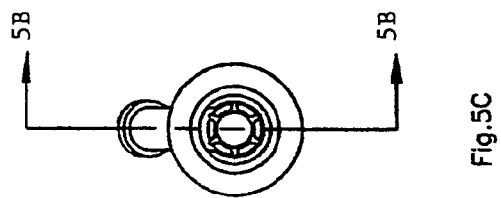
FIG. 5C is an end view of the apparatus of FIG. 5A as seen from the distal end.
Figure 5B:
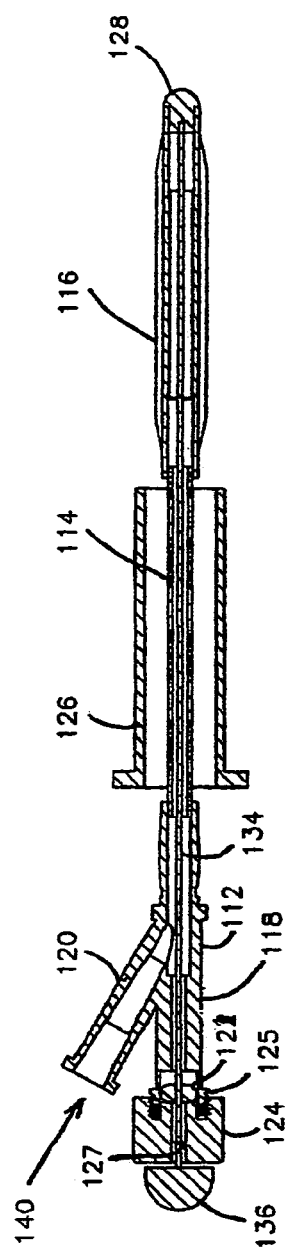
FIG. 5B is a cross-sectional view of the device as shown in FIG. 5C taken along line 5B-5B.
Figure 5A:
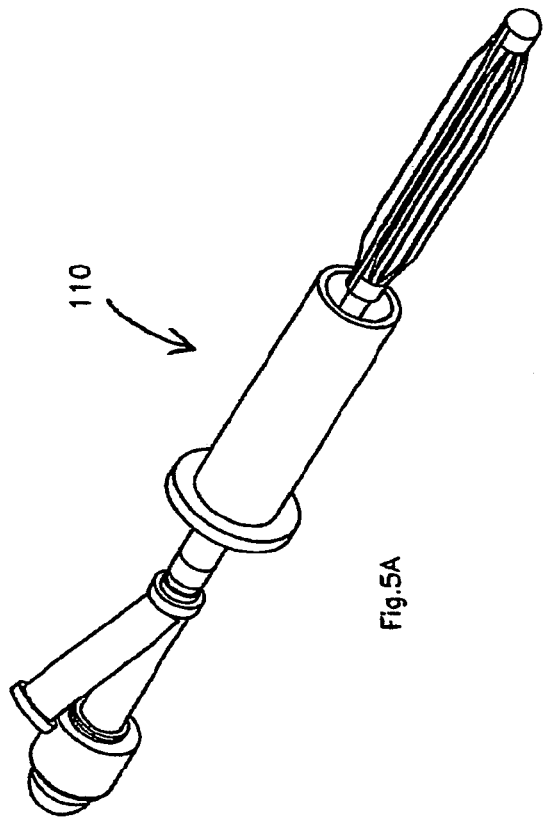
FIG. 5A is a schematic elevation view of apparatus according to a second embodiment of the present invention designed for manual tensioning and optional rotation (twisting and wrapping) of a balloon element to facilitate withdrawal through a small diameter canula from a bone cavity following dilatation and subsequent deflation.

The tubular shell of branch 118 comprises a region adjacent to the threaded region for housing a sealing gasket 122 or similar compressible sealing element having a centrally located aperture. Cap element 124 includes a centrally-located axial bore 127 to accommodate a push rod 134, and also has internal threads sized to mate with the external threads 125 at the proximal end of branch 118. As seen in FIGS. 5A-5C, cap element 124 is loosely threaded onto branch 118, rod 134 is forward (toward the distal end of the catheter), and there is no compression of sealing gasket 121, the condition in which catheter 110 would ordinarily be shipped and stored. Balloon element 116 is shown extended, as best seen in FIG. 5C, and is preferably pleated or folded for compactness.

Push rod 134, having a knob portion 136 at its proximal end, is slidably positioned inside the catheter and is sized to extend axially the full length of catheter 110. Push rod 134 extends through the central bore 127 of cap 124, through the sealing gasket 121, which acts like a bushing for supporting and centering rod 134, through the interior of sleeves 112 and 114, and through the interior of balloon 116 to the sealed tip portion 128. In one variation of this invention embodiment, rod 134 may be connected to or capable of engaging tip portion 128 to facilitate twisting or wrapping balloon element 116 about rod 134 following a dilatation and deflation cycle.

Figure 6C:
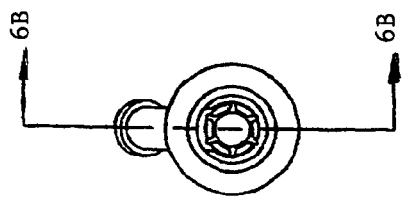
FIG. 6C is an end view of the apparatus of FIG. 6A as seen from the distal end.
Figure 6B:
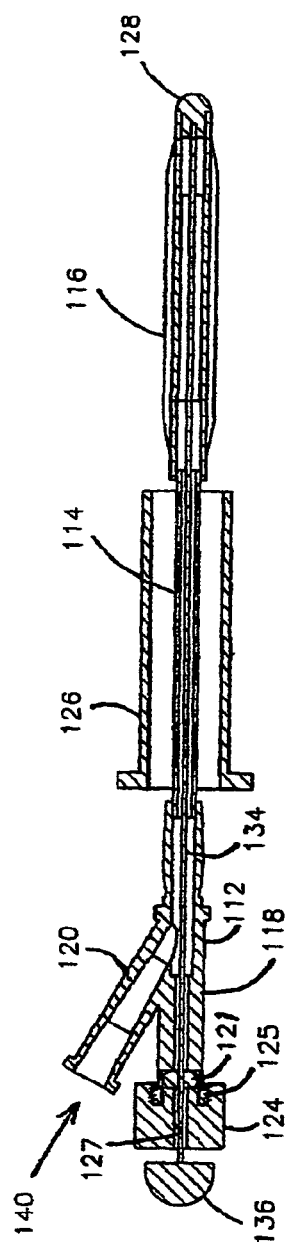
FIG. 6B is a cross-sectional view of the device as shown in FIG. 6C taken along line 6B-6B.
Figure 6A:
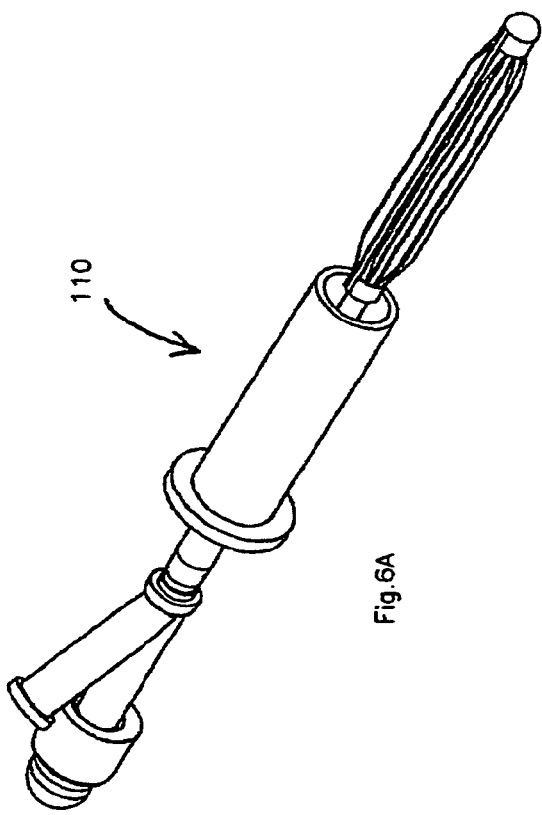
FIG. 6A is a schematic elevation view of the same apparatus shown in FIG. 5A, except that in FIG. 6A the cap has been tightened and the sealing gasket compressed in preparation for use to prevent pressurized inflation fluid from leaking out of the proximal end of the device.
Figure 7C:
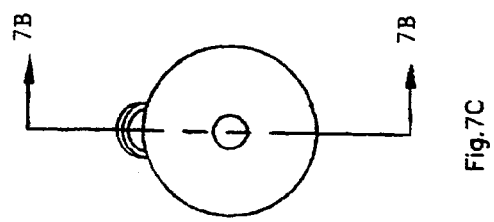
FIG. 7C is an end view of the apparatus of FIG. 7A as seen from the distal end.
Figure 7B:
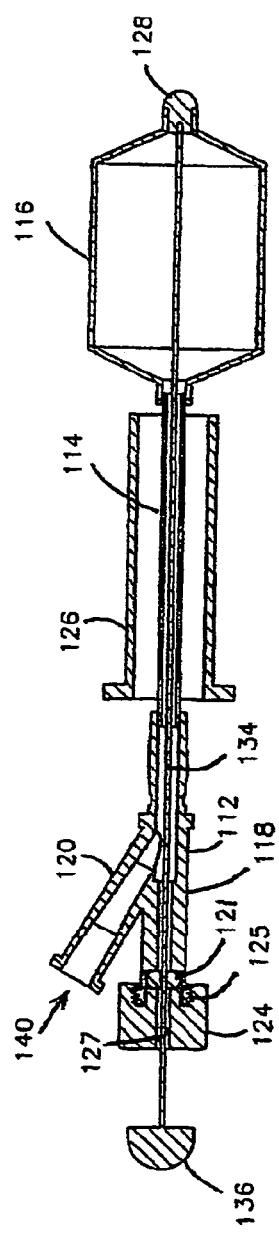
FIG. 7B is a cross-sectional view of the device as shown in FIG. 7C taken along line 7B-7B.
Figure 7A:
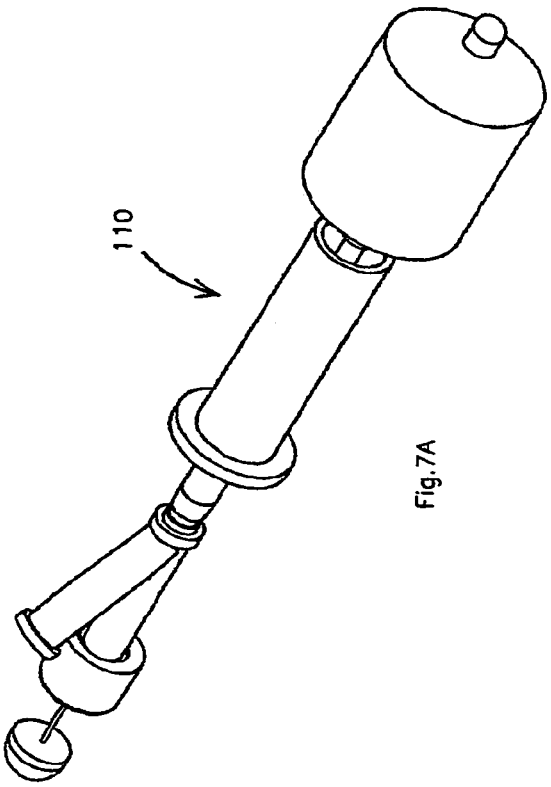
FIG. 7A is a schematic elevation view of the same apparatus shown in FIGS. 5A and 6A, except that in FIG. 7A pressurized fluid has been used to fully inflate the balloon element. As a consequence of the balloon being inflated, it expands in diameter and shortens in length causing the push rod to be displaced toward the proximal end of the apparatus.

In FIGS. 6A-6C, catheter apparatus 110 of FIGS. 5A-5C is shown with cap element 124 screwed down and tightened thereby compressing sealing gasket 121 to form a fluid-tight seal at the sealing gasket and around rod 134 in preparation for using the catheter, while still permitting rod 134 to slide through the gasket aperture. In FIGS. 7A-7C, pressurized fluid 140 has been introduced through branch 120 to fully inflate balloon 116. As balloon 116 is inflated, it expands in diameter and shortens in length causing rod 134 to slide in a proximal direction.

Figure 8C:
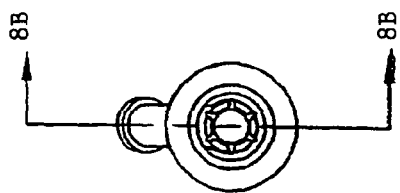
FIG. 8C is an end view of the apparatus of FIG. 8A as seen from the distal end.
Figure 8B:
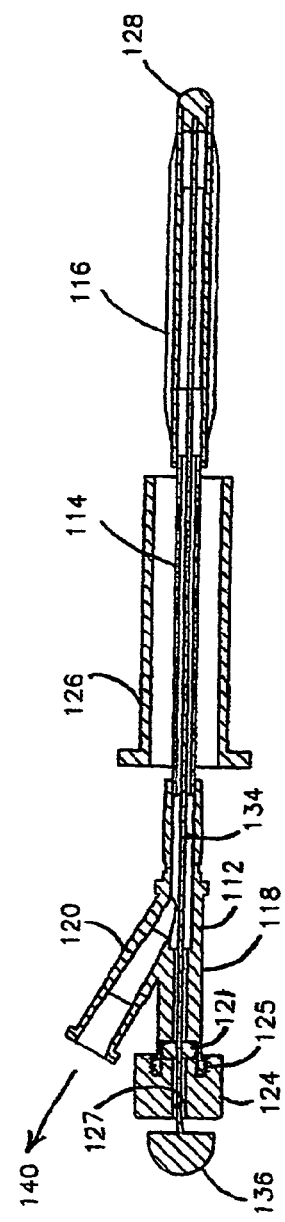
FIG. 8B is a cross-sectional view of the device as shown in FIG. 8C taken along line 8B-8B.
Figure 8A:
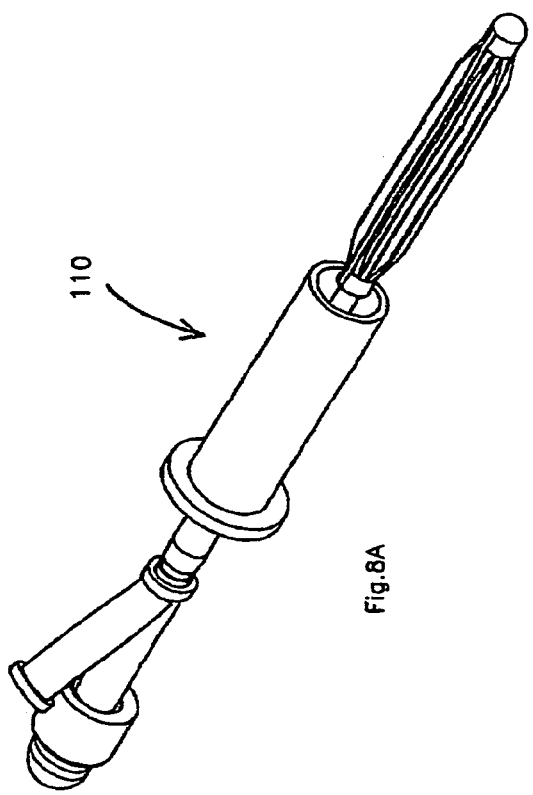
FIG. 8A is a schematic elevation view of the same apparatus shown in FIGS. 5A, 6A and 7A, except that in FIG. 8A dilatation pressure has been removed and, optionally, a vacuum may be applied to the fluid inlet/outlet conduit to withdraw fluid from the formerly inflated balloon element thereby collapsing it. As the balloon is being deflated, or after deflation, axial force is manually applied to the proximal end of the push rod to push it toward the distal end of the device thereby assisting with stretching and refolding or repleating the balloon for easier withdrawal through the canula from a dilated bone cavity.
Figure 9C:
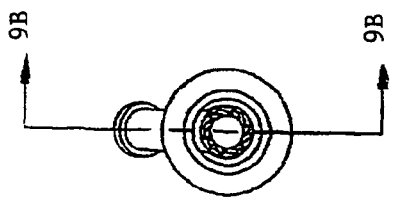
FIG. 9C is an end view of the apparatus of FIG. 9A as seen from the distal end.
Figure 9B:
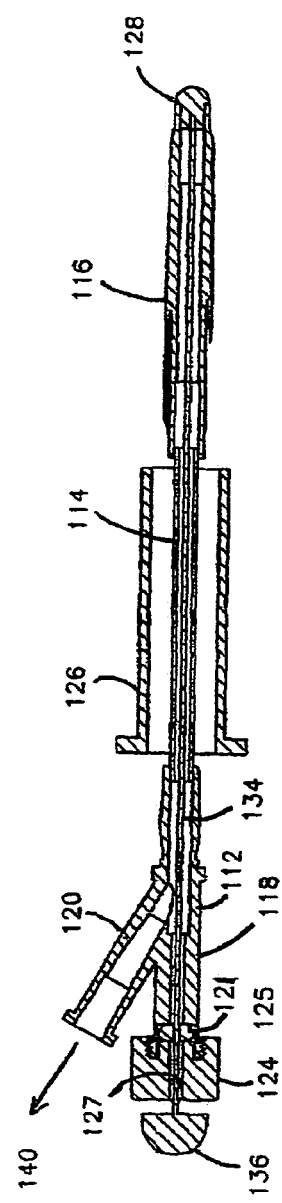
FIG. 9B is a cross-sectional view of the device as shown in FIG. 9C taken along line 9B-9B.
Figure 9A:
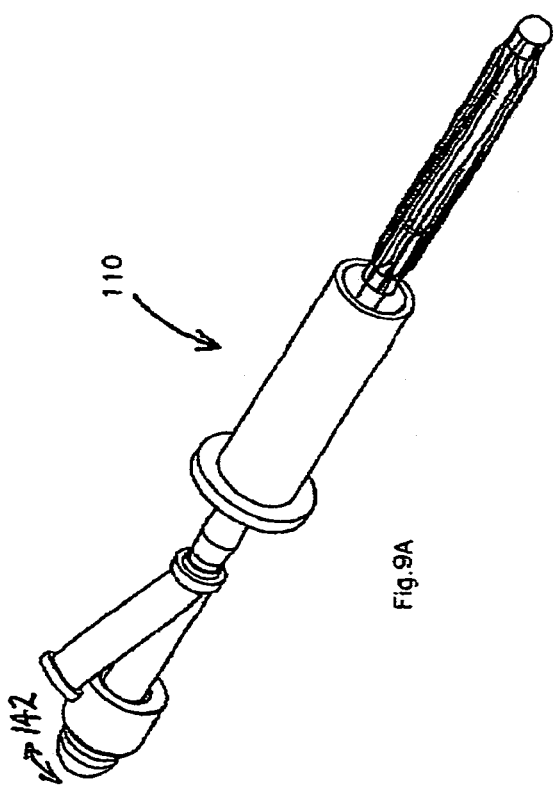
FIG. 9A is a schematic elevation view of the same apparatus shown in FIGS. 5A, 6A and 7A, except that in FIG. 9A the push rod is attached to or engages the balloon and, as the formerly inflated balloon is being deflated, or after deflation, rotational force is manually applied to the proximal end of the push rod to rotate the push rod resulting in wrapping the deflated balloon around the push rod to further reduce the balloon profile for easier withdrawal through the canula from a dilated bone cavity.

In FIGS. 8A-8C, dilatation pressure is removed and fluid is withdrawn from balloon 116 and from the interior of catheter 110 through branch 120. In a preferred embodiment, a vacuum may be applied to the proximal end of branch 20 to assist in withdrawing fluid and in fully collapsing balloon 116. As balloon 116 becomes deflated, axial force is manually applied to the proximal end of rod 134 to push it toward the distal end of the catheter thereby assisting with stretching and refolding or repleating the balloon into a set of small folds or pleats to create a smaller diameter profile for easier withdrawal of the deflated balloon through canula 126. In FIGS. 9A-9C, in addition to using rod 134 to stretch the deflated balloon 116, a rotational force (as indicated by arrows 142) is applied to knob 136 to rotate rod 134 causing balloon element 116 to be wrapped around rod 134, as best seen in FIG. 9C, thereby further reducing the profile of the deflated balloon.

Figure 10C:
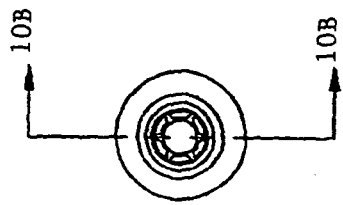
FIG. 10C is an end view of the apparatus of FIG. 10A as seen from the distal end.
Figure 10B:
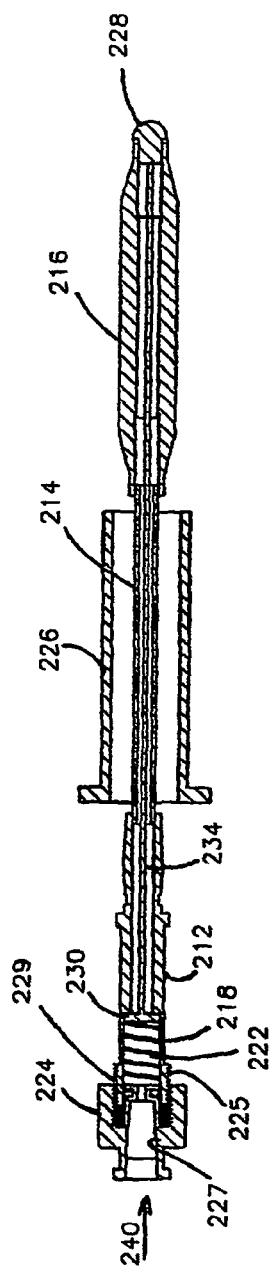
FIG. 10B is a cross-sectional view of the device as shown in FIG. 10C taken along line 10B-10B.
Figure 10A:
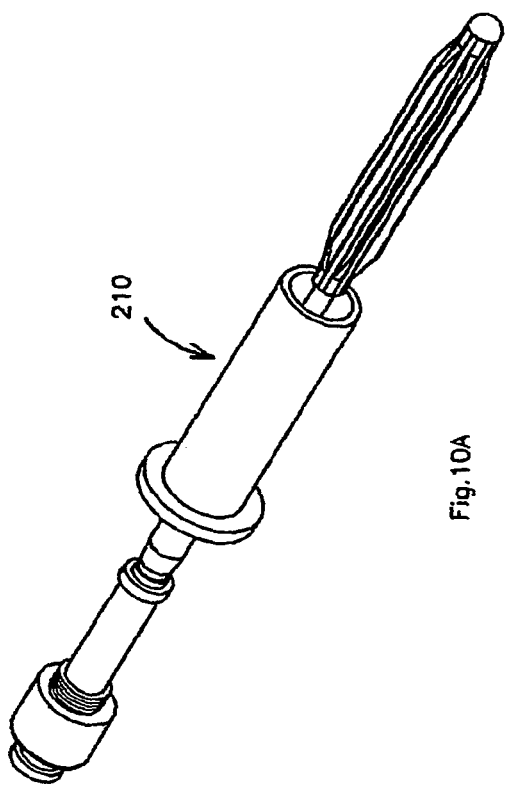
FIG. 10A is a schematic elevation view of apparatus according to a third embodiment of the present invention designed for automatic tensioning of a balloon element to facilitate withdrawal through a small diameter canula from a bone cavity following dilatation and subsequent deflation. The apparatus of FIG. 10A is configured substantially similar to that shown in FIG. 1A except that the inflation/deflation port in FIG. 10A has been integrated into the cap/proximal end structure thereby eliminating the Y-element or side branch in FIG. 1A which served as the fluid inlet/outlet conduit.

FIGS. 10-12 illustrate a dilatation balloon tensioning apparatus according to a third embodiment of the present invention. The balloon dilatation catheter apparatus 210 in FIGS. 10A-10C generally comprises a proximal end catheter sleeve portion 212, a middle sleeve portion 214, and a balloon or inflation element 216 at the distal end of the catheter. As best seen in FIG. 10B, proximal end catheter sleeve portion 212 comprises a tubular shell portion 218 with external threads 225 at its proximal end and a region adjacent to the threaded region for housing a spring element 222.

Cap element 224 includes a centrally-located axial bore 227 through which fluid 240 can be introduced to or withdrawn from catheter 210, and also has internal threads sized to mate with the external threads 225 at the proximal end of the shell portion 218. A gasket, seal, or O-ring 229, or a similar fluid-sealing element, having a centrally-located aperture, is disposed at the proximal end of the region of shell portion 218 which houses spring 222. As seen in FIGS. 10A-10C, cap element 224 is loosely threaded onto shell portion 218, and there is no compression of spring 222, the condition in which catheter 220 would ordinarily be shipped and stored. Balloon element 216 is shown extended, as best seen in FIG. 10C, and is preferably pleated or folded for compactness.

At the distal end of the region for housing spring element 222 (i.e., at the end opposite from where the cap 224 is threaded onto branch 218), a disc element or circular fitting 230 is sized to slide inside the region housing spring element 222 so as to compress the spring element by displacement in the proximal direction or to decompress the spring element by displacement in the distal direction. Associated with disc element 230 is axially moveable rod element 234 (which may or may not be physically connected to disc element 230) which runs axially through the interior of the catheter from the distal side of disc element 230 to the sealed tip portion 228 of balloon 216. Rod element 234 may or may not be physically connected to or may or may not engage balloon tip portion 228. Rod element 234 operating in conjunction with disc element 230 thus can act like a piston to alternately compress and allow decompression of spring element 222.

Also shown in FIGS. 10A-10C, although it is typically not attached to catheter apparatus 210, is a small diameter canula 226 which provides a channel for the catheter apparatus through a bone portion into the bone interior. Balloon element 216 must be able to slide through the hollow interior of canula 226 during insertion of the catheter and, more importantly, during removal of the catheter after the balloon has undergone an inflation/deflation cycle.

Figure 11C:
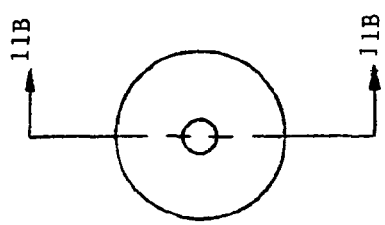
FIG. 11C is an end view of the apparatus of FIG. 11A as seen from the distal end.
Figure 11B:
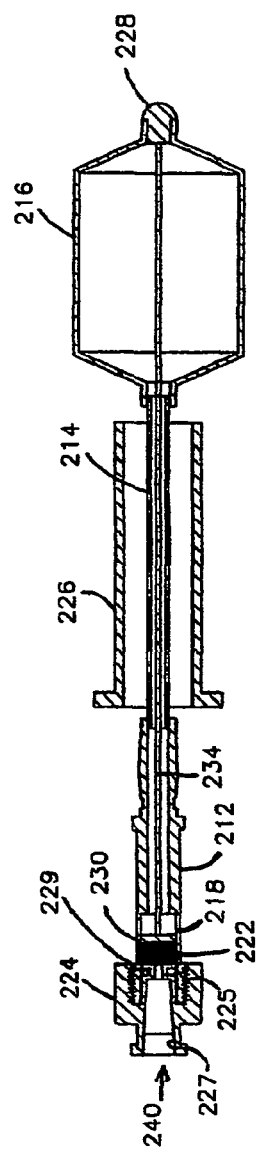
FIG. 11B is a cross-sectional view of the device as shown in FIG. 11C taken along line 11B-11B.
Figure 11A:
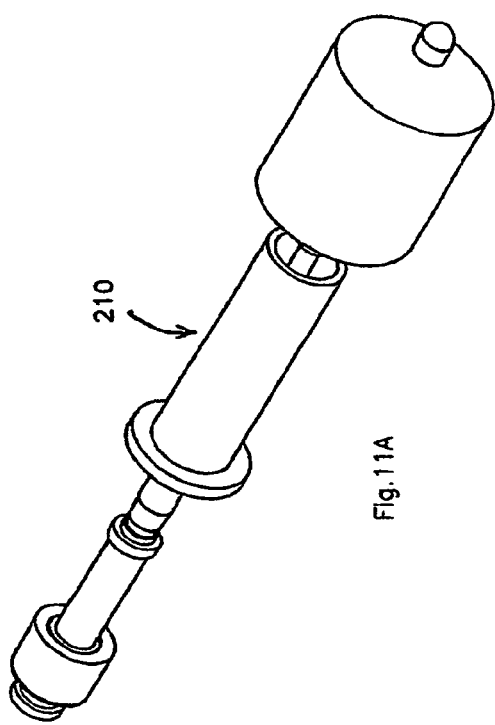
FIG. 11A is a schematic elevation view of the same apparatus shown in FIG. 10A, except that in FIG. 11A the cap has been screwed down and pressurized fluid has been introduced to fully inflate the balloon element. As a consequence of screwing down the cap and inflating the balloon, the spring element has been compressed.

In FIGS. 11A-11C, catheter apparatus 210 of FIGS. 10A-10C is shown with cap element 224 screwed down resulting in at least partially compressing spring element 222 in preparation for use. Also in FIGS. 11A-11C, pressurized fluid 240 has been introduced through axial bore 227, through the interior of proximal sleeve portion 212, and through the interior of middle sleeve portion 214 to fully inflate balloon 216. As balloon 216 is inflated, it expands in diameter and shortens in length causing rod 234 to move in a proximal direction, thereby displacing disc element 230 in a proximal direction and further compressing spring element 222.

Figure 12C:
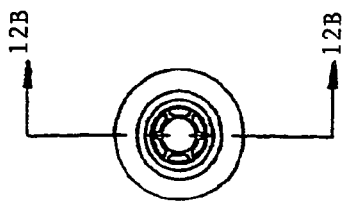
FIG. 12C is an end view of the apparatus of FIG. 12A as seen from the distal end.
Figure 12B:
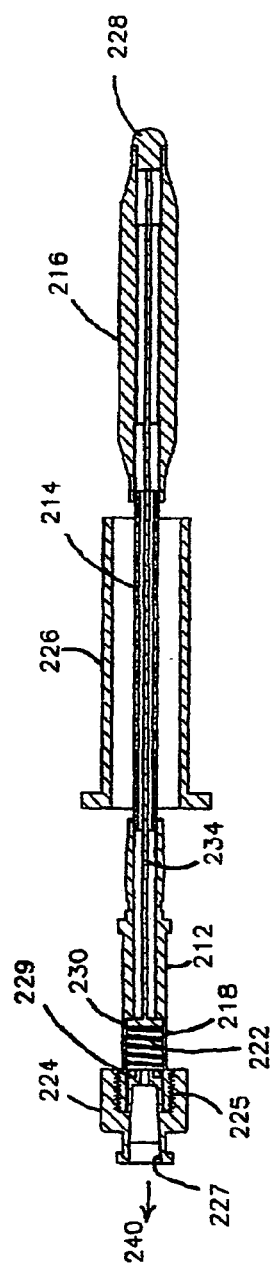
FIG. 12B is a cross-sectional view of the device as shown in FIG. 12C taken along line 12B-12B.
Figure 12A:
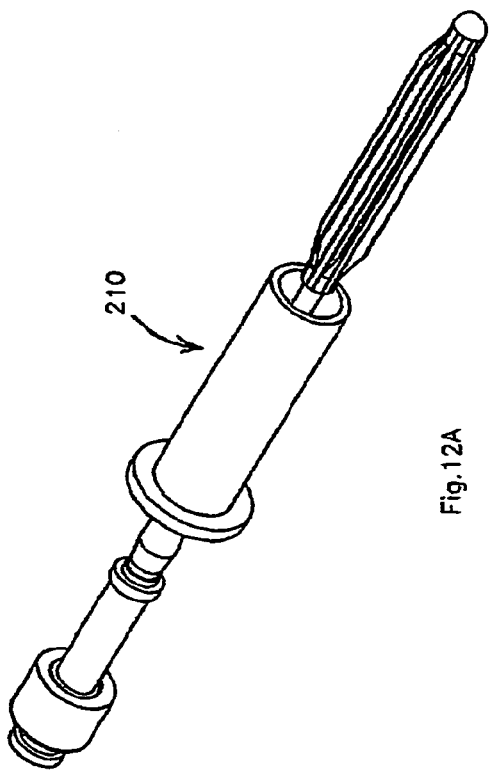
FIG. 12A is a schematic elevation view of the same apparatus shown in FIGS. 10A and 11A, except that in FIG. 12A dilatation pressure has been removed and, optionally, a vacuum may be applied to the inflation/deflation port to withdraw fluid from the formerly inflated balloon element thereby collapsing it. As the balloon element is deflated, the compressed spring element exerts a force on the disc and rod pushing them axially toward the distal end of the apparatus. This results in stretching and tensioning the balloon element thereby assisting in collapsing, folding and/or pleating the balloon element for easier withdrawal from the dilated bone cavity.

In FIGS. 12A-12C, dilatation pressure is removed and fluid 240 is withdrawn from balloon 216 and from the interior of catheter 210 through axial bore 227. In a preferred embodiment, a vacuum may be applied to the proximal end of axial bore 227 to assist in withdrawing fluid and fully collapsing balloon 216. As balloon 216 becomes deflated, the force exerted by the compressed spring element 222 becomes greater than the force exerted by the collapsing balloon. Eventually this results in displacing disc element 230 toward the distal end of the catheter, in turn driving rod 234 in the distal direction, and thereby stretching and tensioning balloon 216. This automatic tensioning of the balloon element upon deflation assists in collapsing, folding and/or pleating the balloon to minimize its lateral profile for easier withdrawal through the small diameter interior channel of canula 226.

FIGS. 13-16 illustrate a dilatation balloon tensioning apparatus according to a fourth embodiment of the present invention. The balloon dilatation catheter apparatus 310 in FIGS. 13A-13C generally comprises a proximal end catheter sleeve portion 312, a middle sleeve portion 314, and a balloon or inflation element 316 at or near the distal end of the catheter. As best seen in FIG. 13B, proximal end catheter sleeve portion 312 comprises a branched or Y-shaped element, of which one arm or branch 318 comprises a tubular shell with external threads 325 at its proximal end, and the second arm or branch 320 comprises a fluid inlet/outlet conduit for introducing pressurized fluid 340 into catheter 310 for inflating balloon 316 or for withdrawing fluid 340 after a dilatation procedure.

Figure 13C:
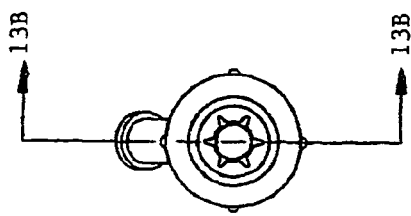
FIG. 13C is an end view of the apparatus of FIG. 13A as seen from the distal end.
Figure 13B:
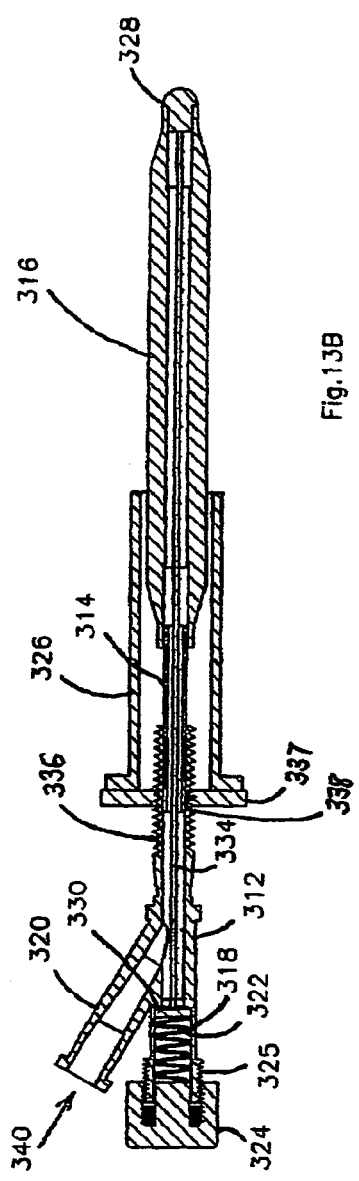
FIG. 13B is a cross-sectional view of the device as shown in FIG. 13C taken along line 13B-13B.
Figure 13A:
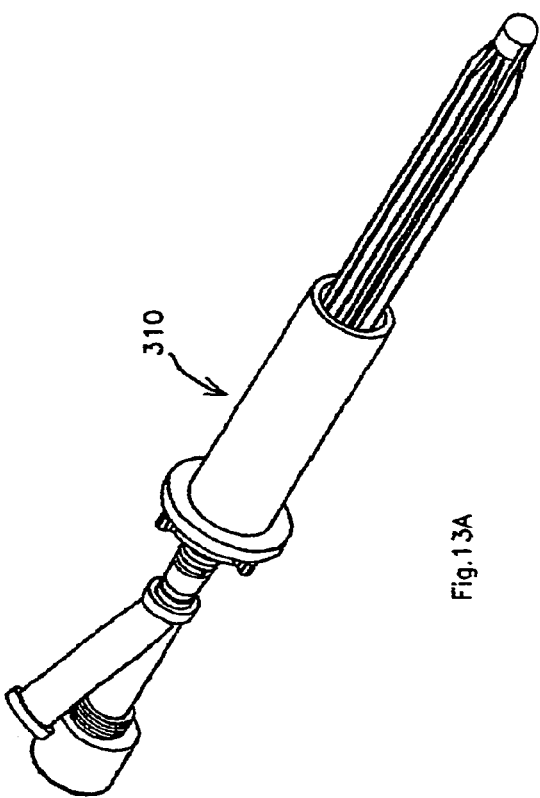
FIG. 13A is a schematic elevation view of apparatus according to a fourth embodiment of the present invention for automatic tensioning of an adjustable length balloon element to facilitate withdrawal through a small diameter canula from a bone cavity following dilatation and subsequent deflation. In this embodiment, the balloon element is designed longer than necessary to fill the bone cavity being treated, and an adjustable clamp, nut, collar or similar element is used to help maintain a precise balloon length and to resist expansion forces during balloon inflation. The apparatus of FIG. 13A is otherwise shown configured substantially similar to that of FIG. 1A with cap and spring elements to effect automatic tensioning of the balloon element upon deflation.

The tubular shell of branch 318 comprises a region adjacent to the threaded region for housing a spring element 322. Cap element 324 has internal threads and is sized to mate with the external threads 325 at the proximal end of branch 318. As seen in FIGS. 13A-13C, the cap element 324 is loosely threaded onto branch 318, and there is no compression of spring element 322, the condition in which catheter 310 would ordinarily be shipped and stored. Balloon element 316 is shown extended, and, as seen in FIGS. 13A and 13C, is preferably pleated or folded for compactness.

At the distal end of the region for housing spring element 322 (i.e., at the end opposite from where the cap 324 is threaded onto branch 318), a disc element or circular fitting 330 is sized to slide inside the region housing spring element 322 so as to compress the spring element by displacement in the proximal direction or to decompress the spring element by displacement in the distal direction. Associated with disc element 330 is axially moveable rod element 334 (which may or may not be physically connected to disc element 330) which runs axially through the interior of the catheter from the distal side of disc element 330 to the sealed tip portion 328 of balloon 316. Rod element 334 may or may not be physically connected to or may or may not engage balloon tip portion 328. Rod element 334 operating in conjunction with disc element 330 thus can act like a piston to alternately compress and allow decompression of spring element 322.

Also shown in FIGS. 13A-13C is a canula element 326. In this embodiment of the invention, however, the canula element 326 does more than just provide a channel through a bone for inserting or removing the catheter apparatus. In this embodiment, the distal section of catheter sleeve portion 312 includes external threads 336. The proximal end of canula 326 is not open, as was the case for the previously described invention embodiments. Instead, canula 326 is sealed at its proximal end by a plate member 337 having a threaded central bore 338, the threads being sized to mate with external threads 336. Thus, by turning canula 326 around the axis of sleeve portion 312, the position of canula 326 can be adjusted relative to balloon 316 by axial movement along the threaded portion of sleeve 312.

In this embodiment of the present invention, balloon element 316 is designed to be longer than the maximum length needed to fill the bone cavity being treated. By adjusting the position of canula 326 along the distal threaded portion of sleeve 312, a surgeon can expose a length of balloon element 316 just sufficient to fill a given bone cavity before inserting the balloon into the bone cavity and inflating it. In this way, a standard catheter apparatus with a standardized balloon element in accordance with the present invention can be easily customized for each application thereby avoiding the need to prepare and stock a multiplicity of balloon lengths.

Figure 14C:
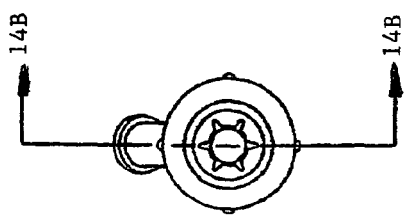
FIG. 14C is an end view of the apparatus of FIG. 14A as seen from the distal end.
Figure 14B:
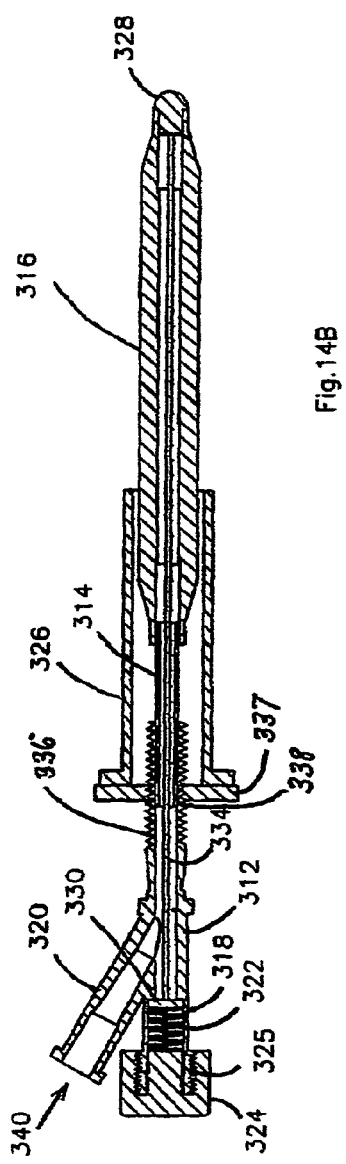
FIG. 14B is a cross-sectional view of the device as shown in FIG. 14C taken along line 14B-14B.
Figure 14A:
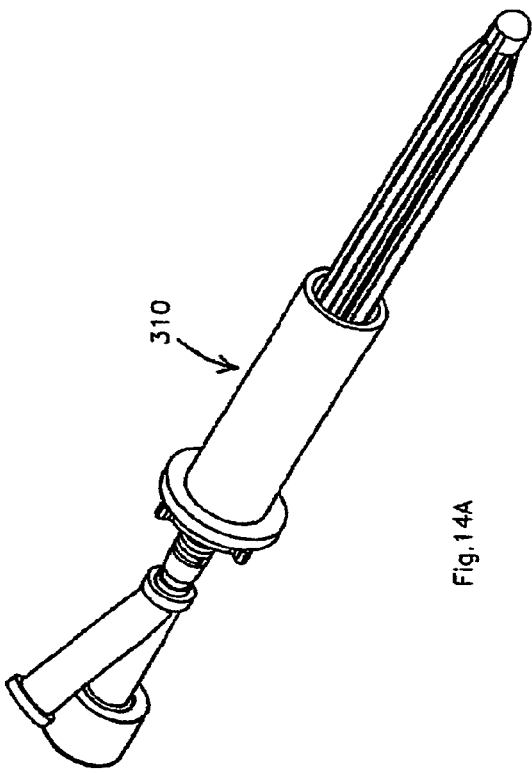
FIG. 14A is a schematic elevation view of the same apparatus shown in FIG. 13A, except that in FIG. 14A the cap has been screwed down resulting in at least partially compressing the spring element in preparation for using the device. The balloon element remains extended and folded and/or pleated.
Figure 15C:
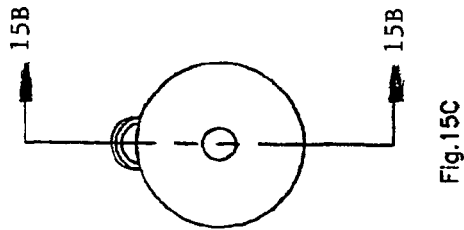
FIG. 15C is an end view of the apparatus of FIG. 15A as seen from the distal end.
Figure 15B:
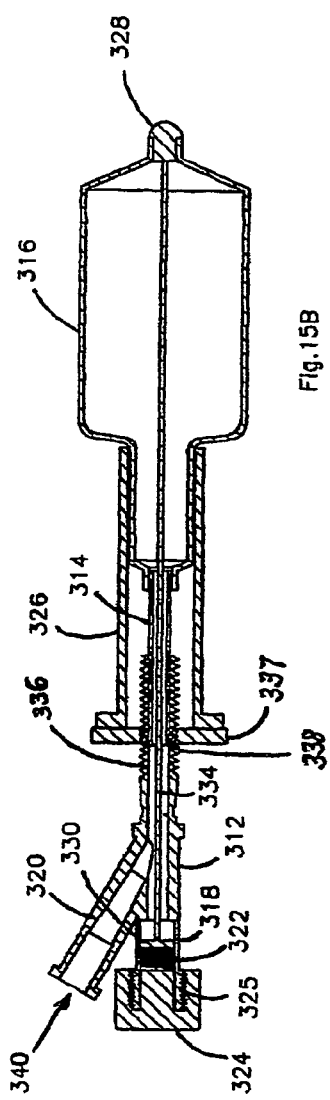
FIG. 15B is a cross-sectional view of the device as shown in FIG. 15C taken along line 15B-15B.
Figure 15A:
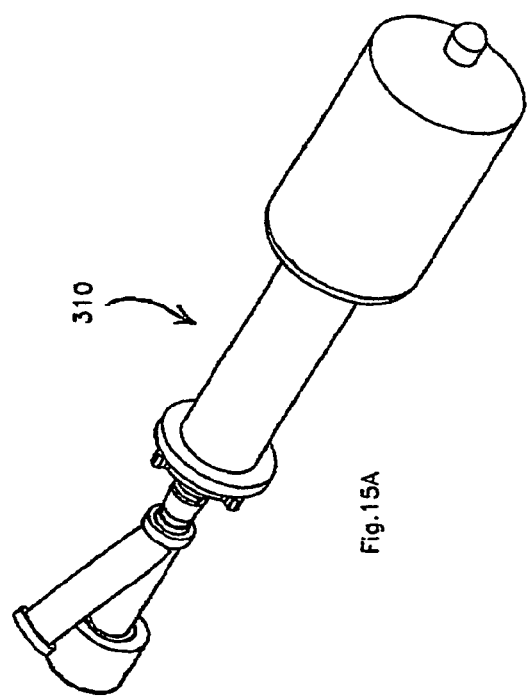
FIG. 15A is a schematic elevation view of the same apparatus shown in FIGS. 13A and 14A, except that in FIG. 15A pressurized fluid has been introduced to inflate the distal end balloon element. As a consequence of the balloon being inflated, inflation forces try to push the canula backward (toward the proximal end) and/or to pull the catheter out. The adjustable nut or comparable element prevents such undesirable movements.

In FIGS. 14A-14C, catheter apparatus 310 of FIGS. 13A-13C is shown with cap element 324 screwed down resulting in at least partially compressing spring element 322 in preparation for use. In FIGS. 15A-15C, pressurized fluid 340 has been introduced through branch 320, through a part of the interior of proximal sleeve portion 312, and through the interior of middle sleeve portion 314 to fully inflate the exposed portion of balloon 316. As seen best in FIG. 15B, the proximal end of balloon 316 is constrained from expanding beyond the internal diameter of canula 326 by the walls of canula 326. As balloon 316 is inflated, at least in part, it expands in diameter and shortens in length causing rod 334 to move in a proximal direction, thereby displacing disc element 330 in a proximal direction and further compressing spring element 322.

Figure 16C:
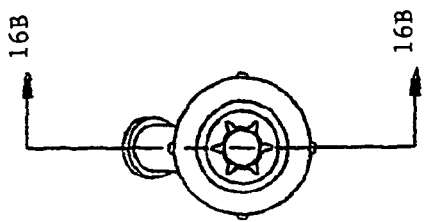
FIG. 16C is an end view of the apparatus of FIG. 16A as seen from the distal end.
Figure 16B:
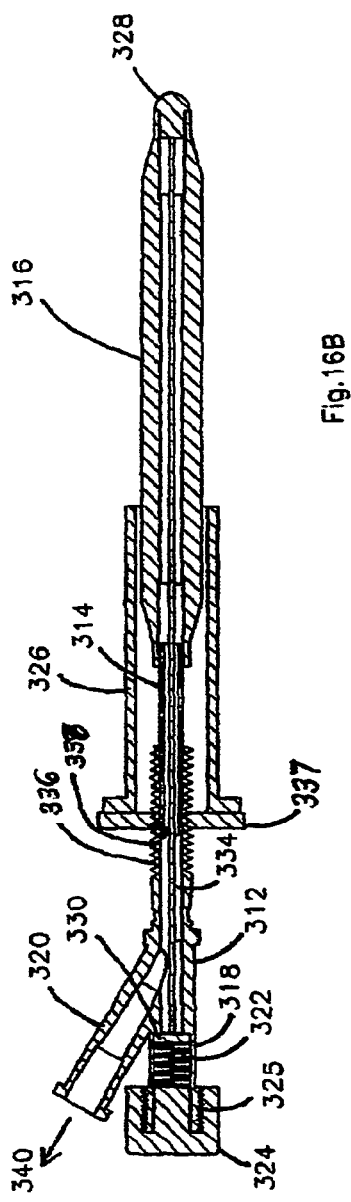
FIG. 16B is a cross-sectional view of the device as shown in FIG. 16C taken along line 16B-16B.
Figure 16A:
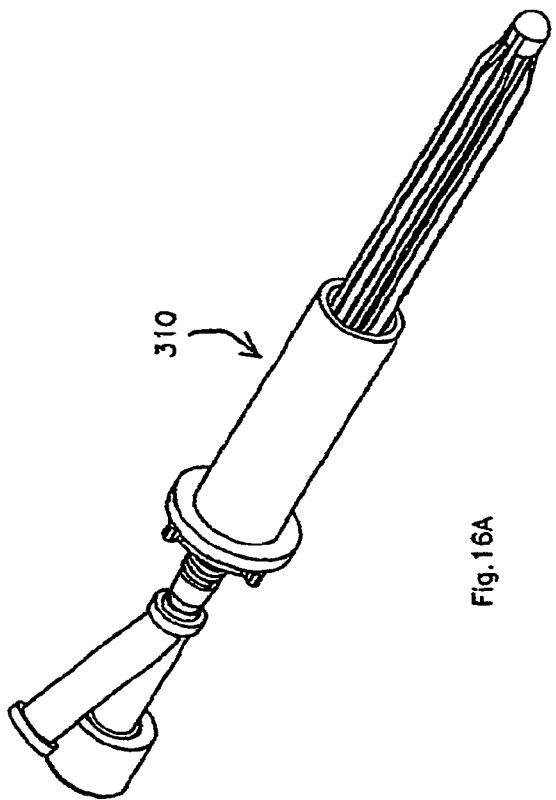
FIG. 16A is a schematic elevation view of the same apparatus shown in FIGS. 13A, 14A and 15A, except that in FIG. 16A dilatation pressure has been removed and, optionally, a vacuum may be applied to the fluid inlet/outlet conduit to withdraw fluid from the formerly inflated balloon element thereby collapsing it. As the balloon element is deflated, the compressed spring element exerts a force on the disc and rod pushing them axially toward the distal end of the apparatus. This results in stretching and tensioning the balloon element thereby assisting in collapsing, folding and/or pleating the balloon element for easier withdrawal from the dilated bone cavity.

In FIGS. 16A-16C, dilatation pressure is removed and fluid is withdrawn from balloon 316 and from the interior of catheter 310 through fluid inlet/outlet branch 320. In a preferred embodiment, a vacuum may be applied to the proximal end of branch 320 to assist in withdrawing fluid and fully collapsing balloon 316. As balloon 316 becomes deflated, the force exerted by the compressed spring element 322 becomes greater than the force exerted by the collapsing balloon. Eventually this results in displacing disc element 330 toward the distal end of the catheter, in turn driving rod 334 in the distal direction, and thereby stretching and tensioning balloon 316. This automatic tensioning of the balloon element upon deflation assists in collapsing, folding and/or pleating the balloon to minimize its lateral profile for easier withdrawal.

FIGS. 17-21 illustrate a dilatation balloon tensioning apparatus according to a fifth embodiment of the present invention. The balloon dilatation catheter apparatus 410 in FIGS. 17A-17C generally comprises a proximal end catheter sleeve portion 412, a middle sleeve portion 414, and a balloon or inflation element 416 at or near the distal end of the catheter. As best seen in FIG. 17B, proximal end catheter sleeve portion 412 comprises a branched or Y-shaped element, of which one arm or branch 418 comprises a tubular shell with external threads 425 at its proximal end, and the second arm or branch 420 comprises a fluid inlet/outlet conduit for introducing pressurized fluid 440 into catheter 410 for inflating balloon 416 or for withdrawing fluid 440 after a dilatation procedure.

Figure 17C:
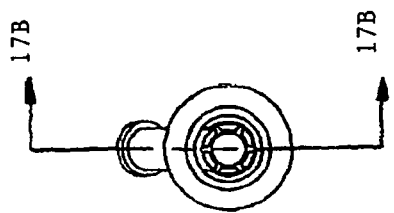
FIG. 17C is an end view of the apparatus of FIG. 17A as seen from the distal end.
Figure 17B:
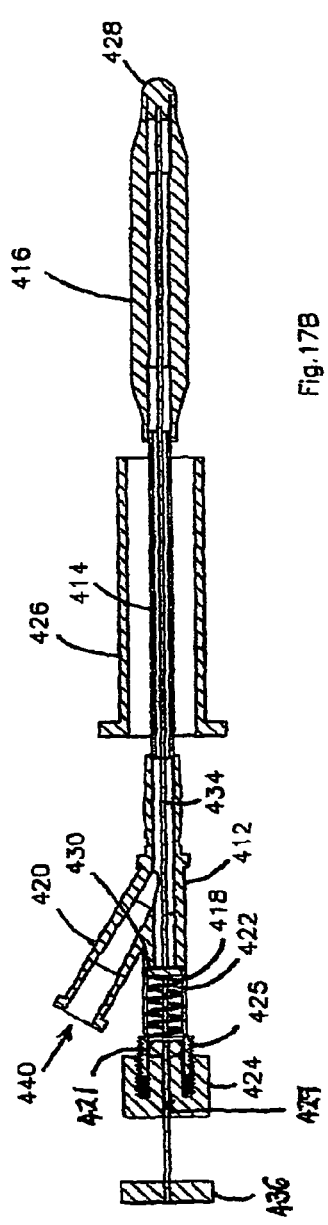
FIG. 17B is a cross-sectional view of the device as shown in FIG. 17C taken along line 17B-17B.
Figure 17A:
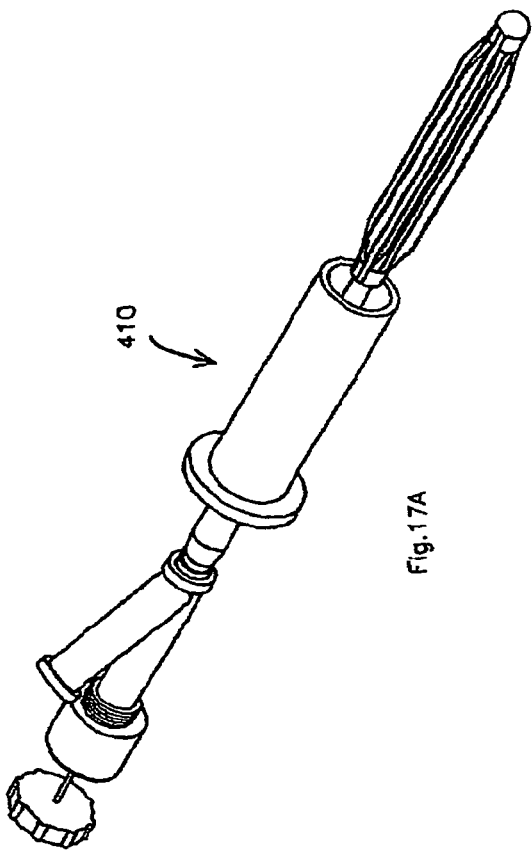
FIG. 17A is a schematic elevation view of apparatus according to a fifth embodiment of the present invention designed for automatic tensioning and optional manual rotation (twisting and wrapping) of a balloon element to facilitate withdrawal through a small diameter canula from a bone cavity following dilatation and subsequent deflation. In this configuration, the rod passes through the disc and is attached to the disc and to the balloon element.

The tubular shell of branch 418 comprises a region adjacent to the threaded region for housing a spring element 422. Cap element 424 has internal threads and is sized to mate with the external threads 425 at the proximal end of branch 418. As seen in FIGS. 17A-17C, the cap element 424 is loosely threaded onto branch 418, and there is no compression of spring element 422, the condition in which catheter 410 would ordinarily be shipped and stored. Cap element 424 further includes a centrally-located axial bore 427 to accommodate a rod element 434 as hereinafter described. Balloon element 416 is shown extended, and, as seen in FIGS. 17A and 17C, is preferably pleated or folded for compactness.

Push rod 434, having a knob portion 436 at its proximal end, is slidably positioned inside the catheter and is sized to extend axially the full length of catheter 410. Push rod 434 extends through the central bore 427 of cap 424, through a sealing gasket 421, which acts like a bushing for supporting and centering rod 434, through the center of spring element 422 and the interior of sleeves 412 and 414, and through the interior of balloon 416 to the sealed tip portion 428. In one variation of this invention embodiment, rod 434 may be connected to or capable of engaging tip portion 428 to facilitate twisting or wrapping balloon element 416 about rod 434 following a dilatation and deflation cycle.

At the distal end of the region for housing spring element 422 (i.e., at the end opposite from where the cap 424 is threaded onto branch 418), a disc element or circular fitting 430 is sized to slide inside the region housing spring element 422 so as to compress the spring element by displacement in the proximal direction or to decompress the spring element by displacement in the distal direction. Disc element 430 has a centrally-located axial bore to accommodate axially moveable rod element 434. Rod element 434 may or may not be physically connected to balloon tip portion 428. Rod element 434 operating in conjunction with disc element 430 thus can act like a piston to alternately compress and allow decompression of spring element 422.

Also shown in FIGS. 17A-17C, although it is typically not attached to catheter apparatus 410, is a small diameter canula 426 which provides a channel for the catheter apparatus through a bone portion into the bone interior. Balloon element 416 must be able to slide through the hollow interior of canula 426 during insertion of the catheter and, more importantly, during removal of the catheter after the balloon has undergone an inflation/deflation cycle.

Figure 18C:
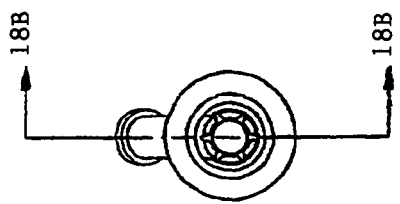
FIG. 18C is an end view of the apparatus of FIG. 18A as seen from the distal end.
Figure 18B:
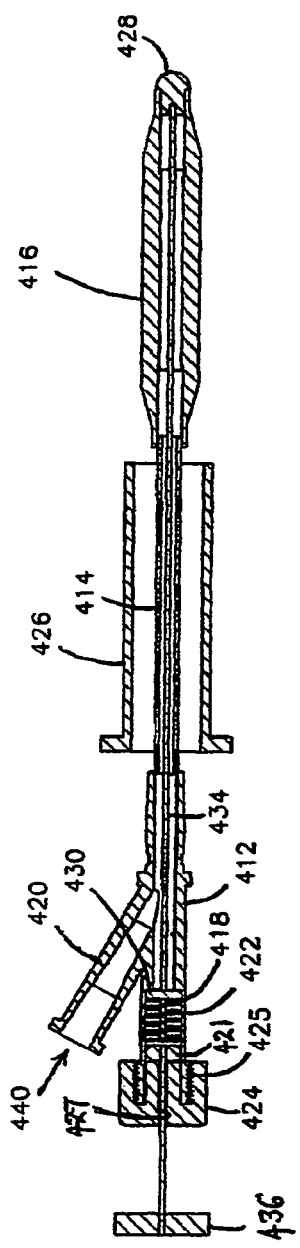
FIG. 18B is a cross-sectional view of the device as shown in FIG. 18C taken along line 18B-18B.
Figure 18A:
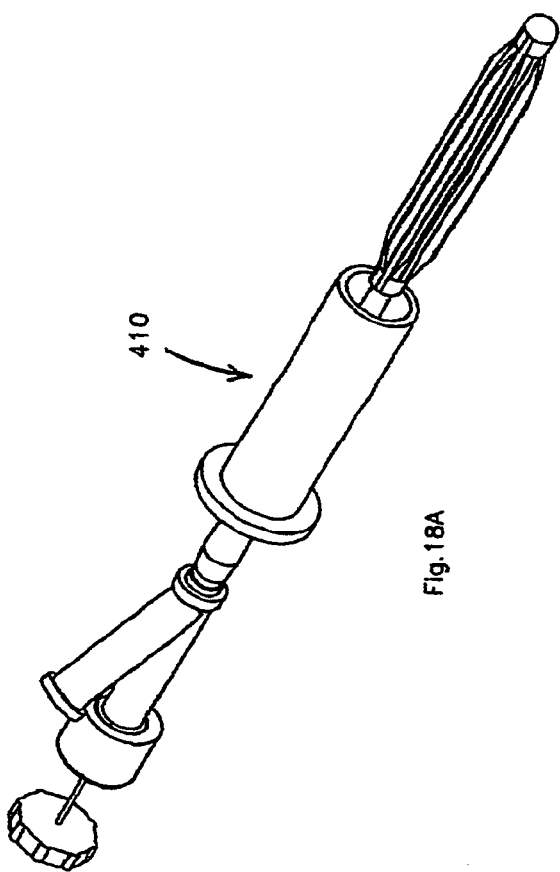
FIG. 18A is a schematic elevation view of the same apparatus shown in FIG. 17A, except that in FIG. 18A the cap has been screwed down resulting in at least partially compressing the spring element in preparation for using the device. The balloon element remains extended and folded and/or pleated.
Figure 19C:
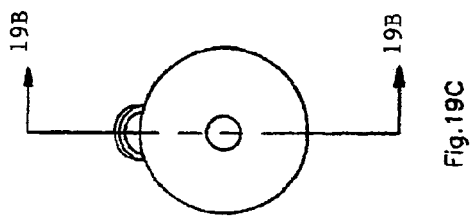
FIG. 19C is an end view of the apparatus of FIG. 19A as seen from the distal end.
Figure 19B:
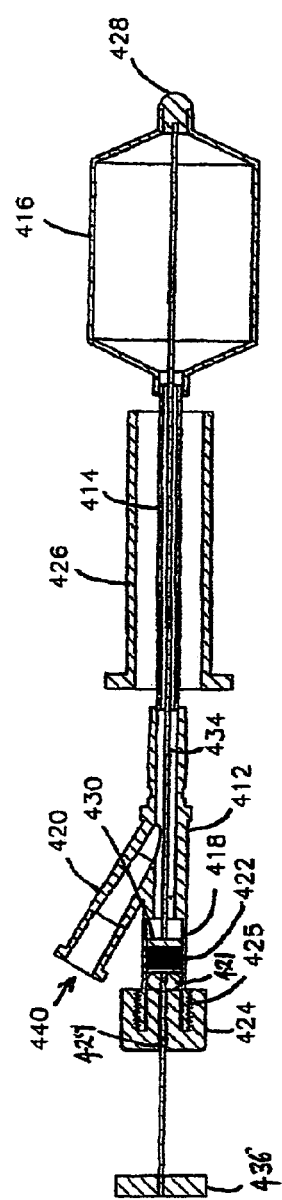
FIG. 19B is a cross-sectional view of the device as shown in FIG. 19C taken along line 19B-19B.
Figure 19A:
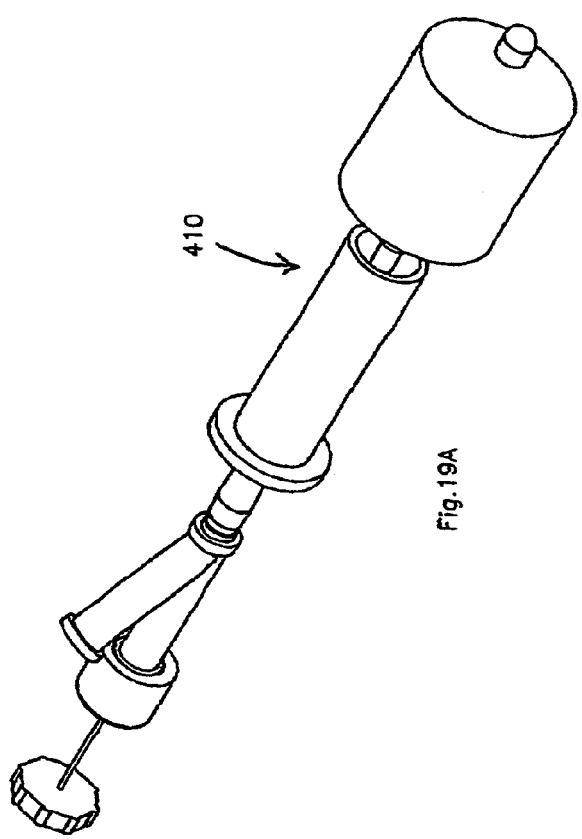
FIG. 19A is a schematic elevation view of the same apparatus shown in FIGS. 17A and 18A, except that in FIG. 19A pressurized fluid has been introduced to fully inflate the balloon element. As a consequence of the balloon being inflated, it expands in diameter and shortens in length causing the rod/disc elements to be displaced toward the proximal end of the apparatus thereby further compressing the spring element.

In FIGS. 18A-18C, catheter apparatus 410 of FIGS. 17A-17C is shown with cap element 424 screwed down resulting in at least partially compressing spring element 422 in preparation for use. In FIGS. 19A-19C, pressurized fluid 440 has been introduced through branch 420, through a part of the interior of proximal sleeve portion 412, and through the interior of middle sleeve portion 414 to fully inflate balloon 416. As balloon 416 is inflated, it expands in diameter and shortens in length causing rod 434 to move in a proximal direction, thereby displacing disc element 430 in a proximal direction and further compressing spring element 422.

Figure 21C:
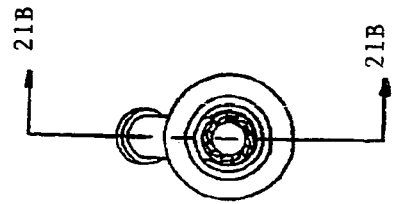
FIG. 21C is an end view of the apparatus of FIG. 21A as seen from the distal end.
Figure 21B:
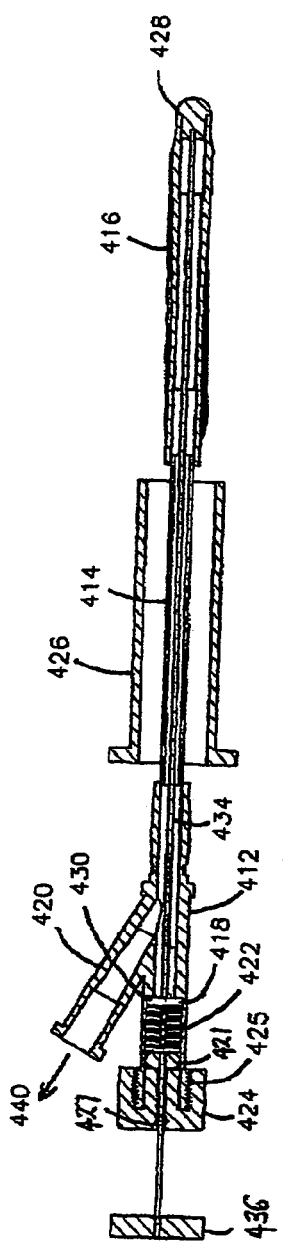
FIG. 21B is a cross-sectional view of the device as shown in FIG. 21C taken along line 21B-21B.
Figure 21A:
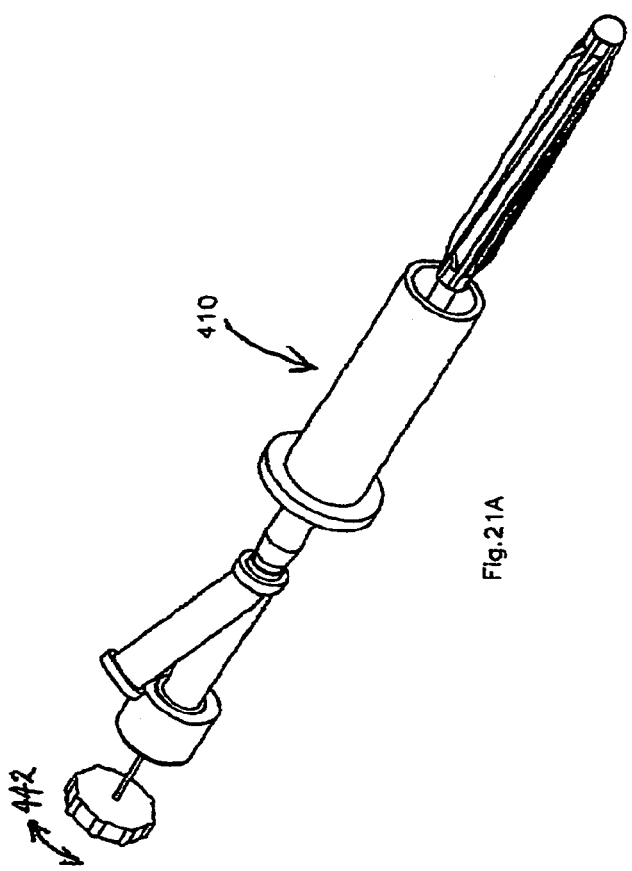
FIG. 21A is a schematic elevation view of the same apparatus shown in FIGS. 17A, 18A, 19A and 20A, except that in FIG. 21A the rod is attached to or engages the balloon and, as the formerly inflated balloon is being deflated, or after deflation, rotational force is manually applied to the proximal end of the rod to rotate the rod resulting in wrapping the deflated balloon around the rod to further reduce the balloon profile for easier withdrawal through the canula from a dilated bone cavity.

In FIGS. 20A-20C, dilatation pressure is removed and fluid is withdrawn from balloon 416 and from the interior of catheter 410 through fluid inlet/outlet branch 420. In a preferred embodiment, a vacuum may be applied to the proximal end of branch 420 to assist in withdrawing fluid and fully collapsing balloon 416. As balloon 416 becomes deflated, the force exerted by the compressed spring element 422 becomes greater than the force exerted by the collapsing balloon. Eventually this results in displacing disc element 430 toward the distal end of the catheter, in turn driving rod 434 in the distal direction, and thereby stretching and tensioning balloon 416. This automatic tensioning of the balloon element upon deflation assists in collapsing, folding and/or pleating the balloon to minimize its lateral profile for easier withdrawal through the small diameter interior channel of canula 426. In FIGS. 21A-21C, in addition to using rod 434 to stretch the deflated balloon 416, a rotational force (as indicated by arrows 442) is applied to knob 436 to rotate rod 434 causing balloon element 416 to be wrapped around rod 434, as best seen in FIG. 21C, thereby further reducing the profile of the deflated balloon.

FIGS. 22-25 illustrate a dilatation balloon tensioning apparatus according to a sixth embodiment of the present invention. The balloon dilatation catheter apparatus 510 in FIGS. 22A-22D generally comprises a proximal end catheter sleeve portion 512, a middle sleeve portion 514, and a balloon or inflation element 516 at or near the distal end of the catheter. As best seen in FIG. 22B, proximal end catheter sleeve portion 512 comprises a branched or Y-shaped element, of which one arm or branch 518 comprises a tubular shell with external threads 525 at its proximal end, and the second arm or branch 520 comprises a fluid inlet/outlet conduit for introducing pressurized fluid 540 into catheter 510 for inflating balloon 516 or for withdrawing fluid 540 after a dilatation procedure.

Cap element 524 has internal threads and is sized to mate with the external threads 525 at the proximal end of branch 518. As seen in FIGS. 22A-22D, the cap element 524 is loosely threaded onto branch 518, and there is no compression of a spring element 522, located inside balloon 516, the condition in which catheter 510 would ordinarily be shipped and stored. Balloon element 516 is shown extended, and, as seen in FIGS. 22A and 22C, is preferably pleated or folded for compactness.

An axially moveable rod element 534 having a head portion 530 at its proximal end runs axially through the interior of the catheter from the distal side of cap element 524 to the sealed tip portion 528 of balloon 516. Rod element 534 may or may not be physically connected to balloon tip portion 528. The head portion 530 of rod 534 moves axially within a region in the interior of branch 518 as rod 534 slides toward or away from tip portion 528.

At the distal end of rod 534 and located inside balloon 516 is a spring tensioning system comprising a spiral spring element 522 wrapped around at least a portion of rod 534. FIG. 22D is an enlarged view of the balloon end of the catheter which better shows spring element 522 spiraling around the distal end of rod 534. As best seen in FIG. 22D, the distal end of rod 534 in one embodiment may comprise two telescoping rod sections consisting of a hollow tubular section 546 and a smaller-diameter section 547 sized to slidably fit inside the hollow interior of section 546 and terminating in a bulbous rod tip 548. Spring element 522 is a spiral spring having a diameter smaller than the outer diameter of rod section 546 but larger than the outer diameter of rod section 547. Spring element 522 is not secured at either end but occupies a region bounded at the proximal end by the distal end of rod section 546 and at the distal end by the proximal surface of rod tip 548.

Figure 24C:
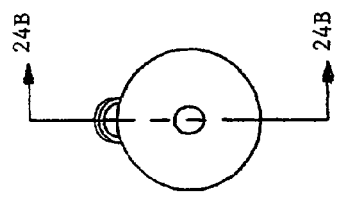
FIG. 24C is an end view of the apparatus of FIG. 24A as seen from the distal end.
Figure 24D:
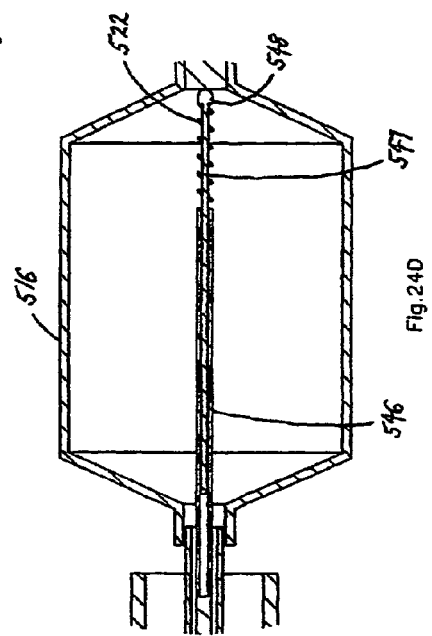
FIG. 24D is an enlarged cross-sectional view of the distal end of the device as shown in FIG. 24B to better illustrate details of the spring tensioning system at the balloon end of the apparatus.
Figure 24B:
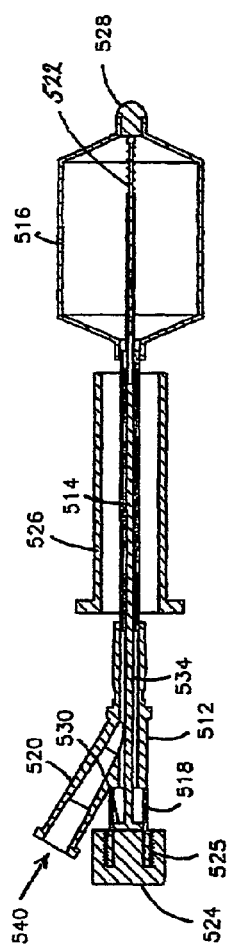
FIG. 24B is a cross-sectional view of the device as shown in FIG. 24C taken along line 24B-24B.
Figure 24A:
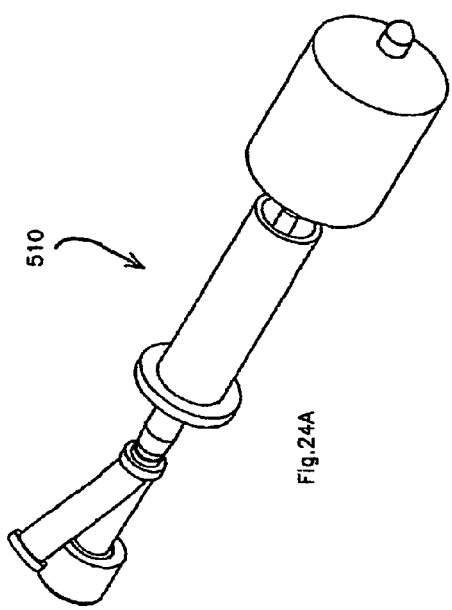
FIG. 24A is a schematic elevation view of the same apparatus shown in FIGS. 22A and 23A, except that in FIG. 24A pressurized fluid has been introduced to fully inflate the balloon element. As a consequence of the balloon being inflated, it expands in diameter and shortens in length thereby further compressing the spring element.

In FIGS. 23A-23D, catheter apparatus 510 of FIGS. 22A-22D is shown with cap element 524 screwed down resulting in at least partially compressing spring element 522 by the distal movement of rod section 546 relative to rod section 547, in preparation for use. In FIGS. 24A-24D, pressurized fluid 540 has been introduced through branch 520, through a part of the interior of proximal sleeve portion 512, and through the interior of middle sleeve portion 514 to fully inflate balloon 516. As balloon 516 is inflated, it expands in diameter and shortens in length causing further inward telescoping of rod section 547 into rod section 546 (as best seen in FIG. 24D), thereby further compressing spring element 522.

In FIGS. 25A-25D, dilatation pressure is removed and fluid is withdrawn from balloon 516 and from the interior catheter 510 through fluid inlet/outlet branch 520. In a preferred embodiment, a vacuum may be applied to the proximal end of branch 520 to assist in withdrawing fluid and fully collapsing balloon 516. As balloon 516 becomes deflated, the force exerted by the compressed spring element 522 becomes greater than the force exerted by the collapsing balloon. Eventually this results in an outward telescoping of rod section 547 out of rod section 546 driven by the decompression of spring element 522, and thereby stretching and tensioning balloon 516. This automatic tensioning of the balloon element upon deflation assists in collapsing, folding and/or pleating the balloon to minimize its lateral profile for easier withdrawal through the small diameter interior channel of canula 526.

Apparatus according to the present invention can be utilized in a variety of ways. As previously discussed, a principal intended application for the apparatus and methods of this invention is in treating vertebral fractures by dilating the interior of a vertebral element using a balloon catheter. FIGS. 26-33 illustrate various specific applications of apparatus and methods according to this invention in treating vertebral fractures.

Figure 26A:
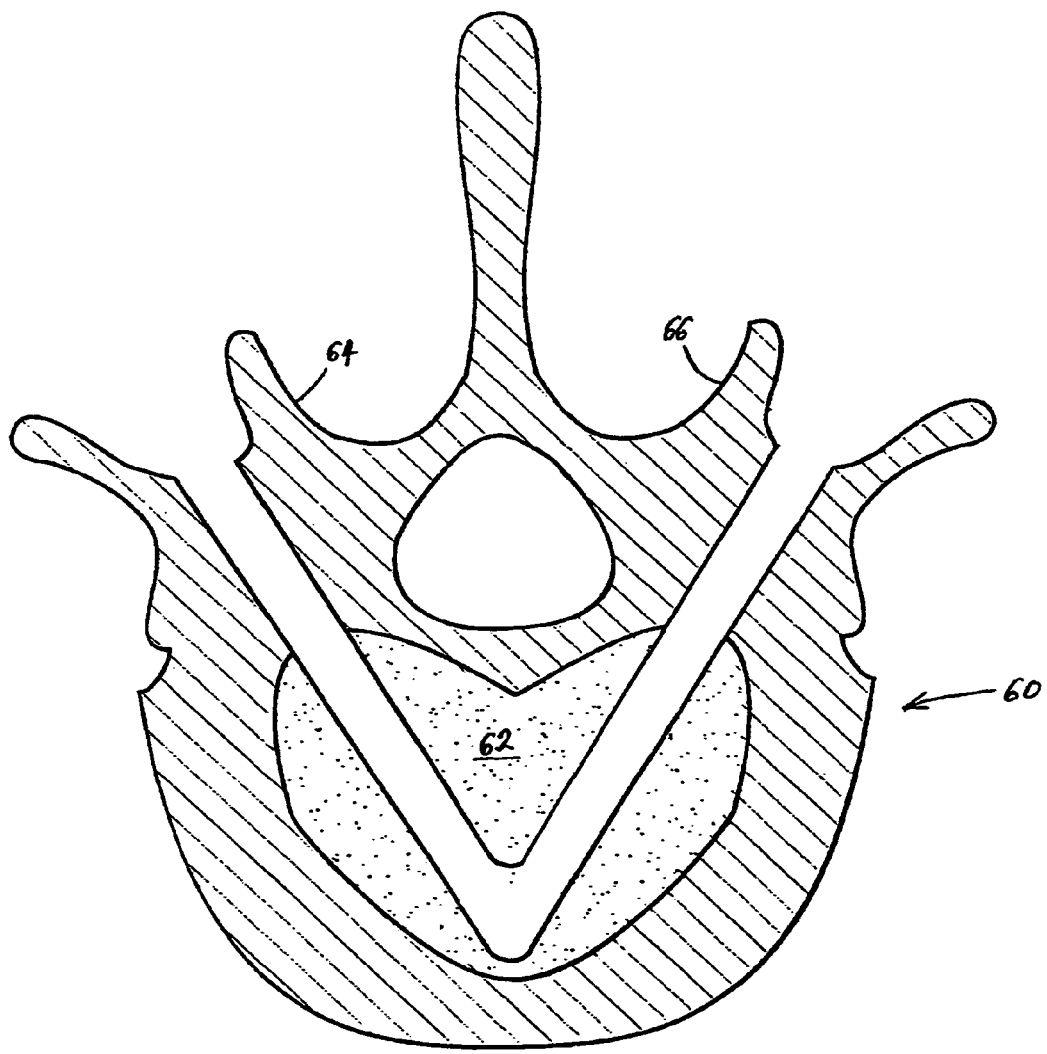

For example, FIGS. 26A-26D schematically illustrate the treatment of a partially collapsed vertebral segment with an apparatus according to one embodiment of this invention. FIG. 26A schematically illustrates a cross-section of a vertebral segment 60 comprising an interior region 62 filled with cancellous, or spongy, bone, and left and right pedicle portions 64 and 66 respectively. As seen in FIG. 26A, straight-line access holes have been drilled or otherwise created through pedicle portions 64 and 66 and into the adjacent cancellous bone in interior region 62 so as to meet and form a V-shaped passageway from the exterior of vertebral segment 60 through interior region 62.

Figure 26B:
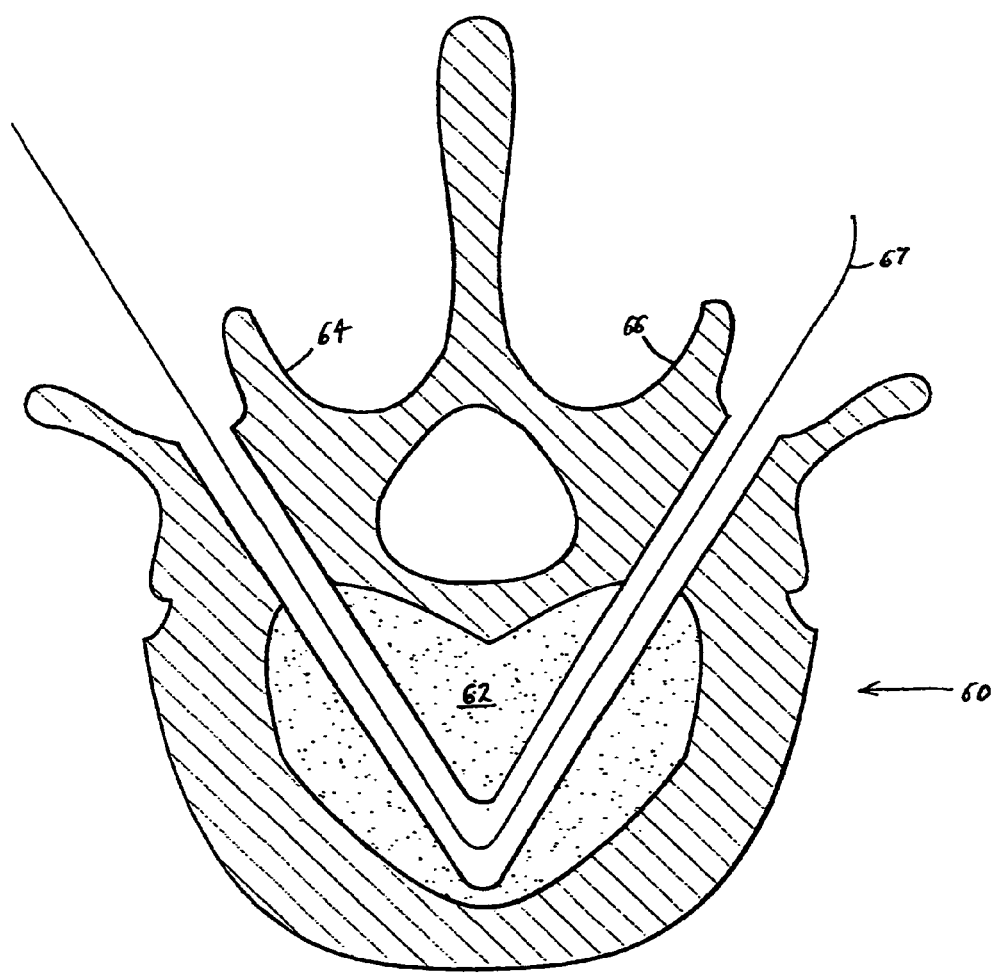
Figure 26C:
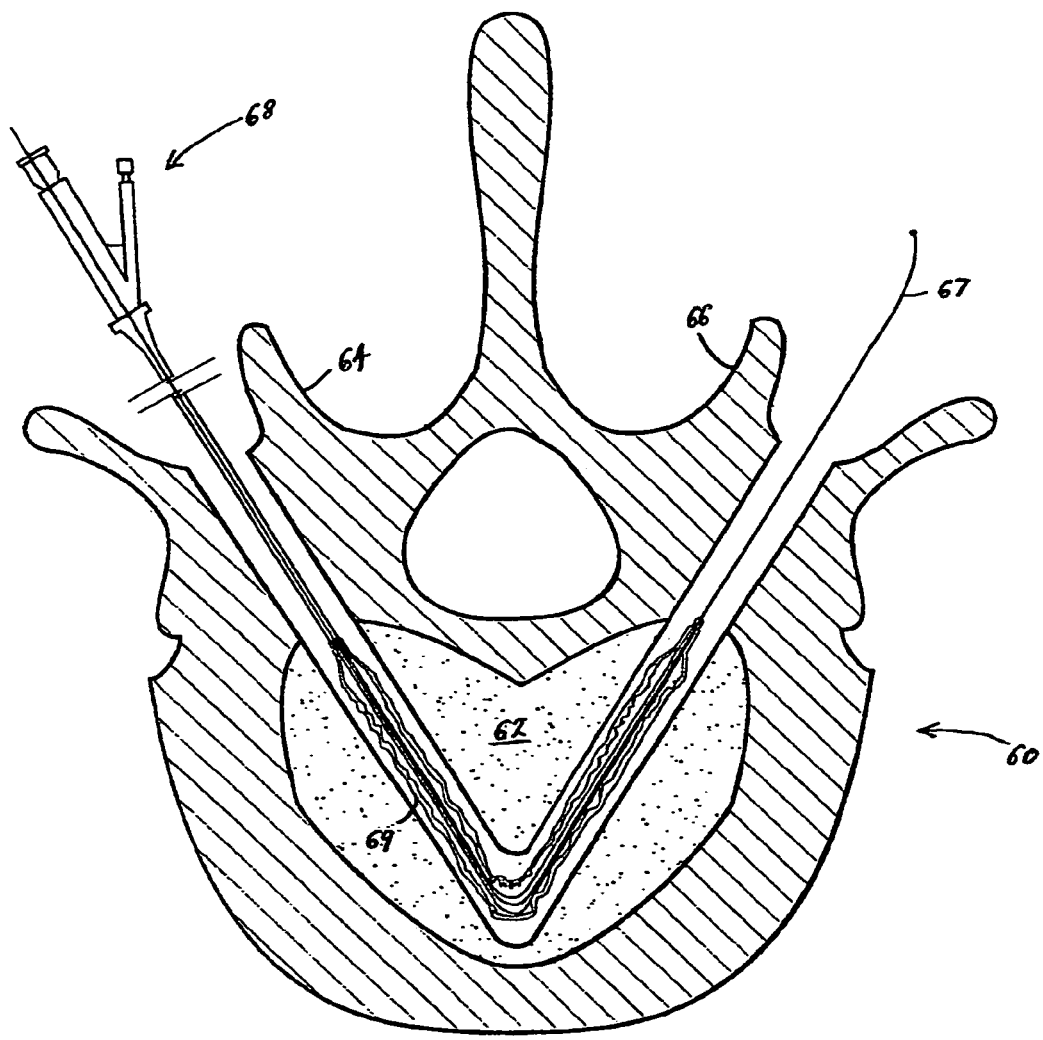

As shown in FIG. 26B, a catheter guidewire 67 may then be threaded through the V-shaped passageway. As shown in FIG.

Figure 26D:
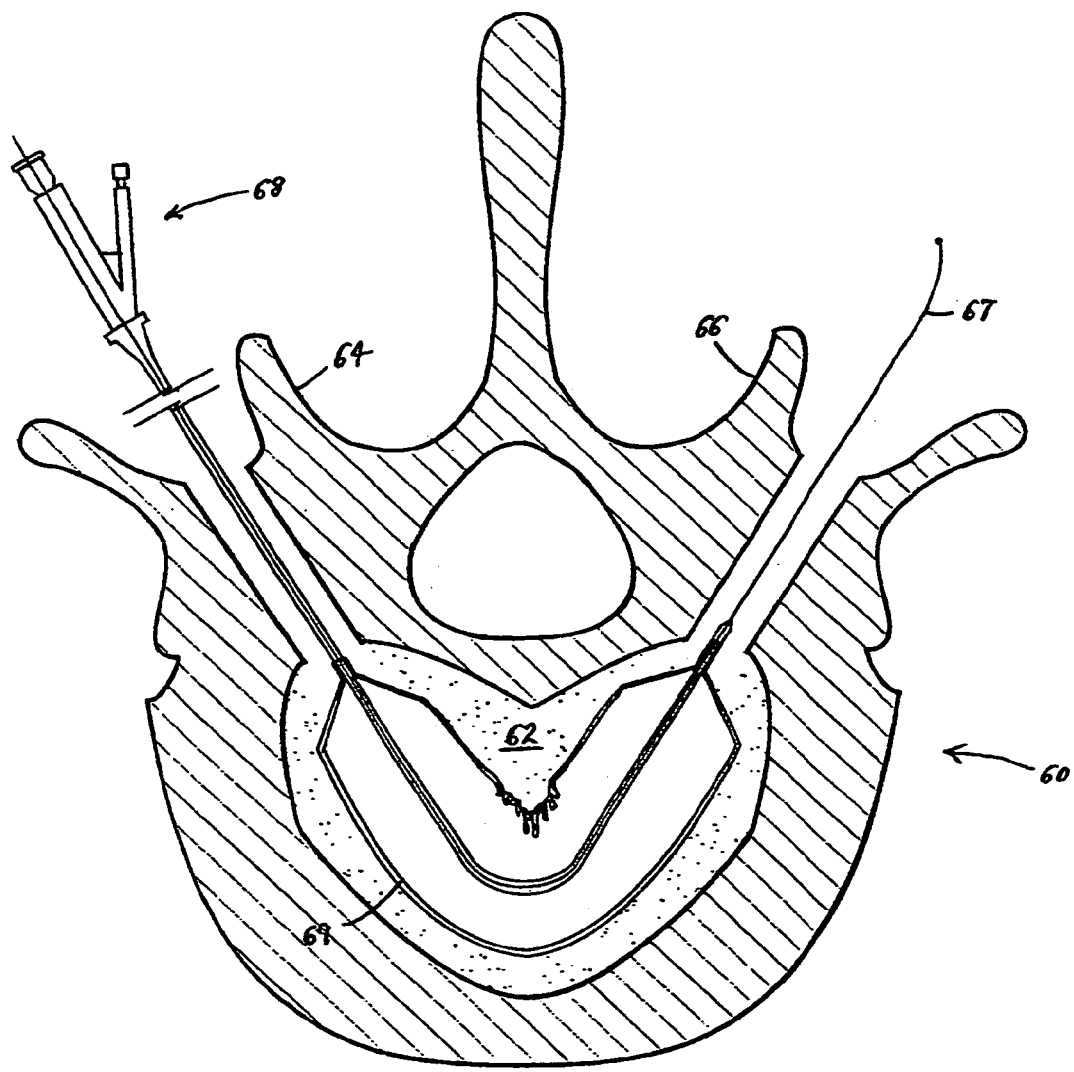

26C, a catheter apparatus 68 according to the present invention is introduced into the V-shaped passageway along guidewire 67 so as to position all of the uninflated balloon element 69 of the catheter apparatus inside interior region 62. As shown in FIG. 26D, once balloon element 69 is properly positioned in region 62, the balloon element can be inflated, expanding against the surrounding cancellous bone and thereby restoring the shape and size of the vertebral segment close if not identical to its pre-injury configuration. Following this procedure, balloon element 69 is deflated and its lateral profile is reduced by stretching, tensioning, folding or pleating the balloon element utilizing the automatic or manual tensioning and/or twisting techniques previously described for a catheter apparatus in accordance with this invention. Once the lateral profile of balloon element 69 is sufficiently reduced, catheter apparatus 68, including balloon element 69, can be easily withdrawn from the vertebral segment.

Figure 27A:
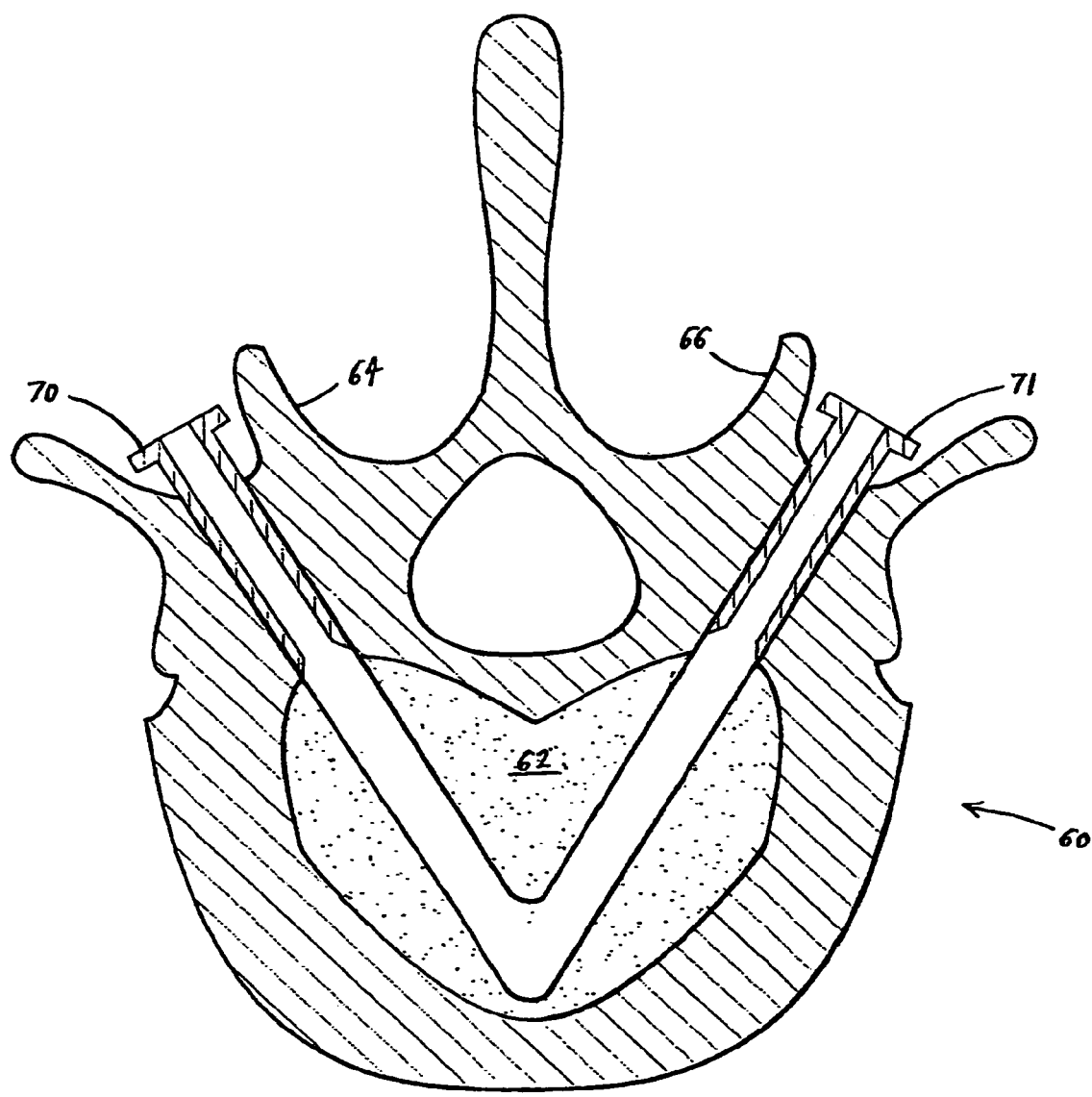
Figure 27B:
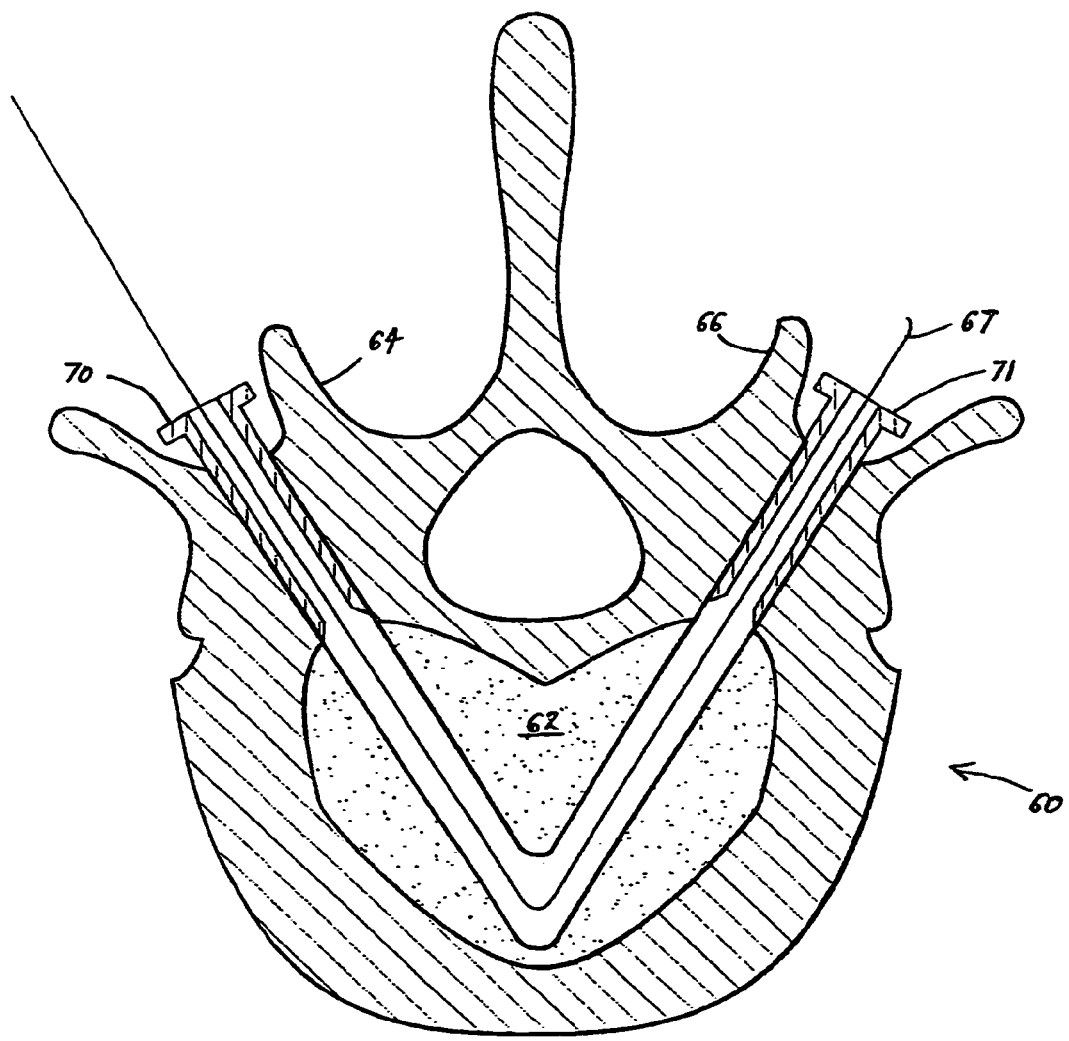
Figure 27C:
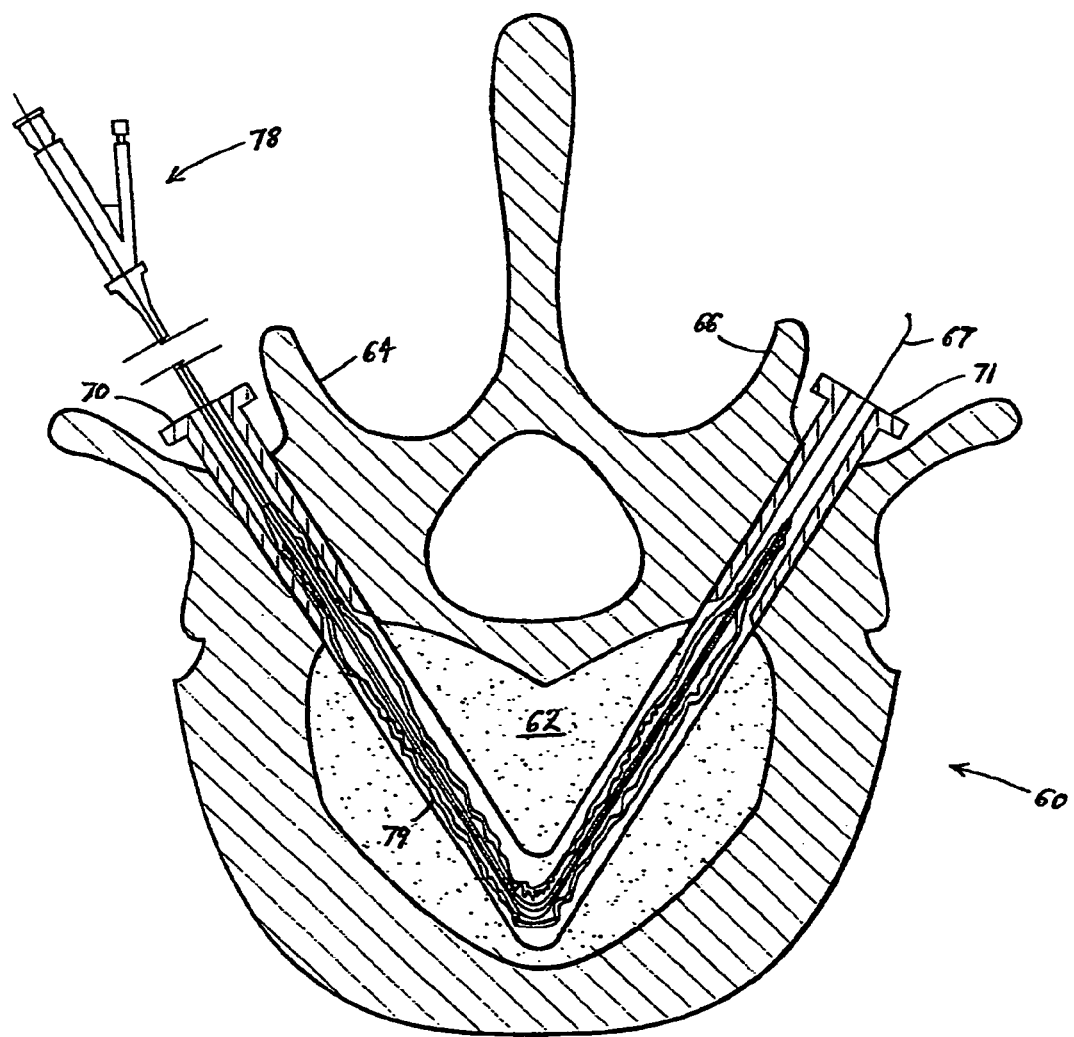
Figure 27D:
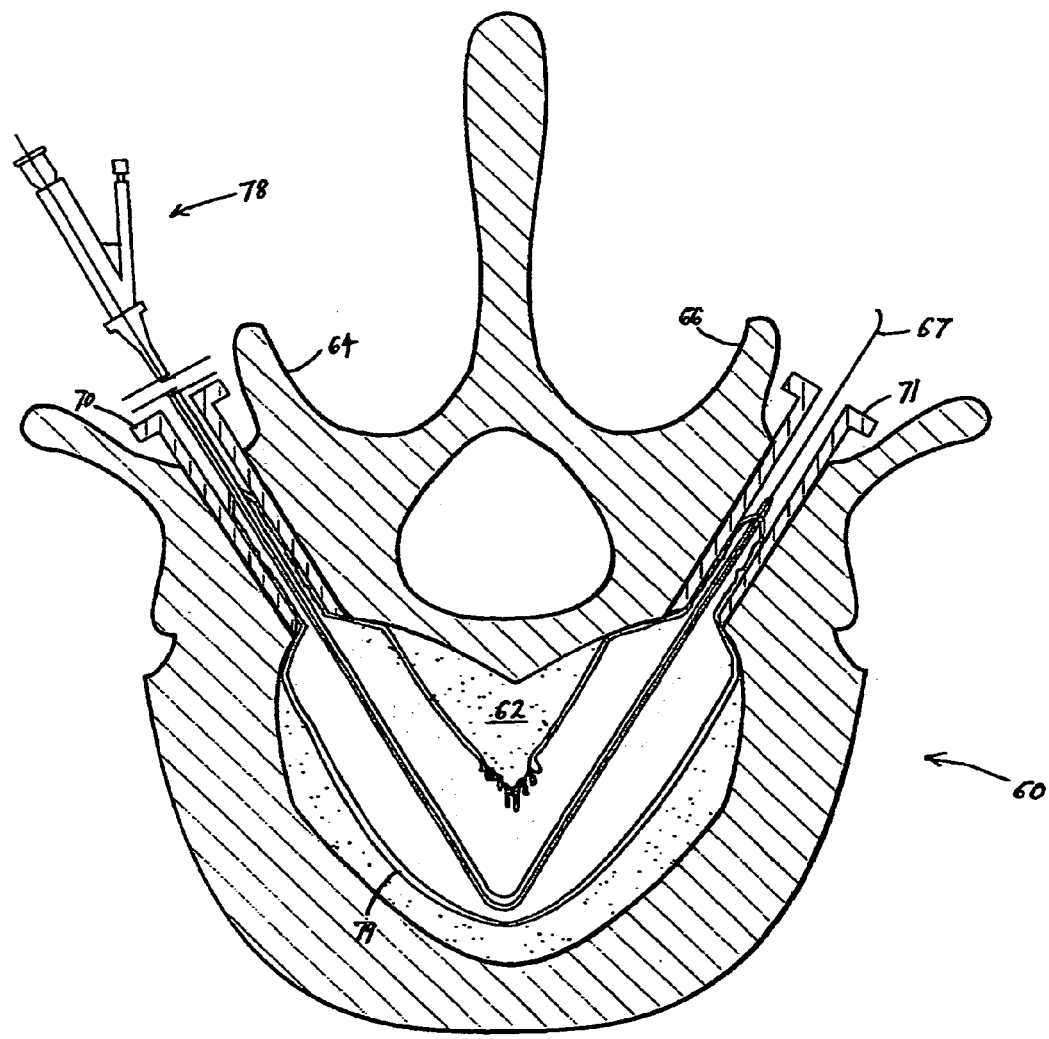

FIGS. 27A-27D generally correspond respectively to FIGS. 26A-26D, as described above, except that in FIGS. 27A-27D, after the V-shaped passageway is created through vertebral segment 60, canula elements 70 and 71 are inserted respectively into the passages through pedicle portions 64 and 66. As seen in FIG. 27C, the catheter apparatus 78 used with this embodiment of the invention includes a balloon element 79 which is longer than the length of the V-shaped passageway through interior region 62. As a result, a proximal-end portion of balloon element 79 remains in canula 70 and a distal-end portion of balloon element 79 is in canula 71. As seen in FIG. 27D, when balloon element 79 is inflated, only the middle portion of the balloon which is inside region 62 can fully inflate. The inflation of the proximal and distal ends of balloon element 79 is constrained by the inner walls respectively of canula elements 70 and 71. The canula elements 70 and 71 prevent the expansion forces exerted by the inflated balloon inside the passages through pedicle portions 64 and 66 from rupturing these relatively fragile bones.

Figure 28A:
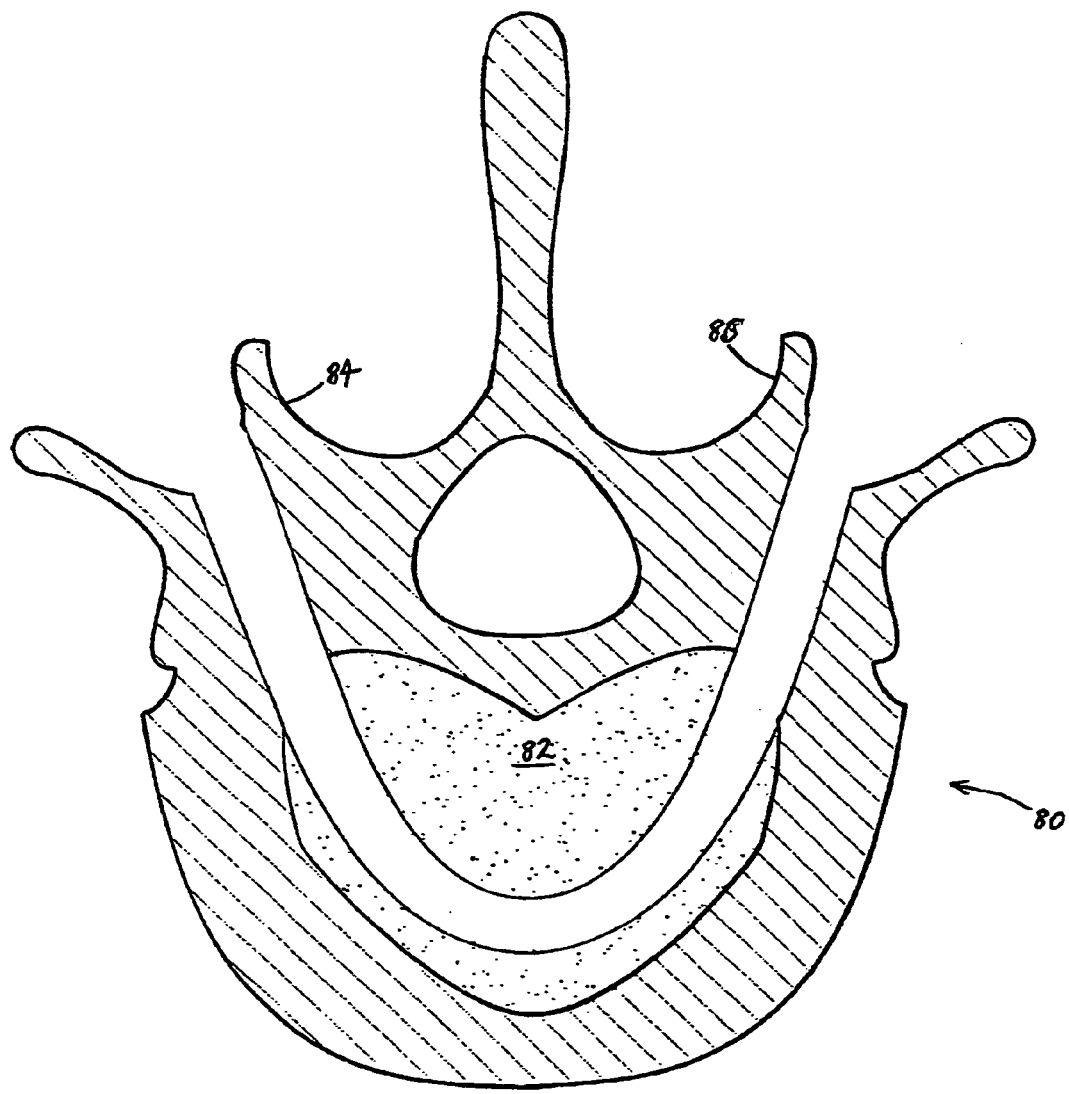

FIGS. 28A-28E schematically illustrate a cross-section of a vertebral segment 80 comprising an interior region 82 filled with cancellous bone, and left and right pedicle portions 84 and 86 respectively. As seen in FIG. 28A, a curved passageway has been created through left pedicle portion 84, through the cancellous bone in region 82, and through the right pedicle portion 86 to form a U-shaped channel from the exterior of vertebral segment 80 through interior region 82.

Figure 28B:
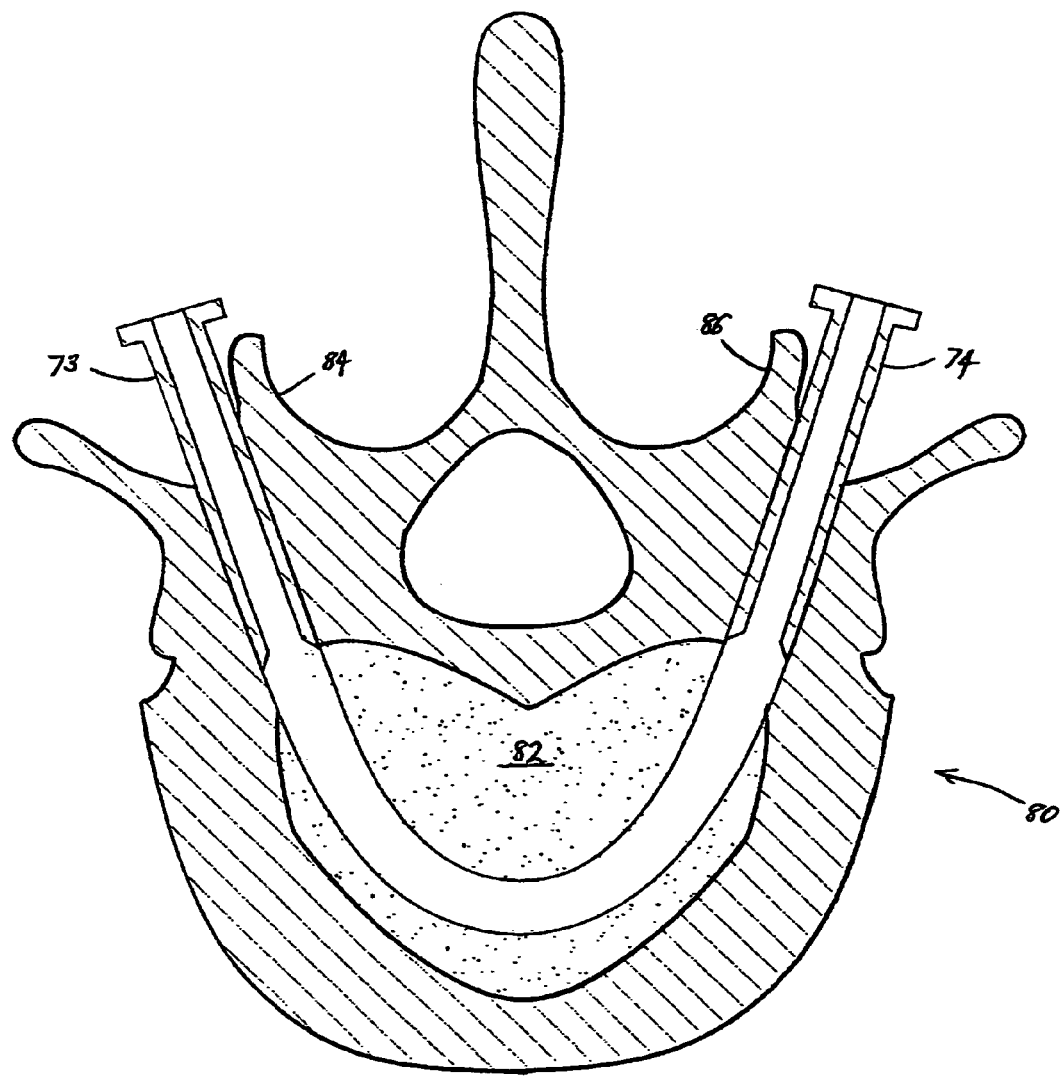
Figure 28C:
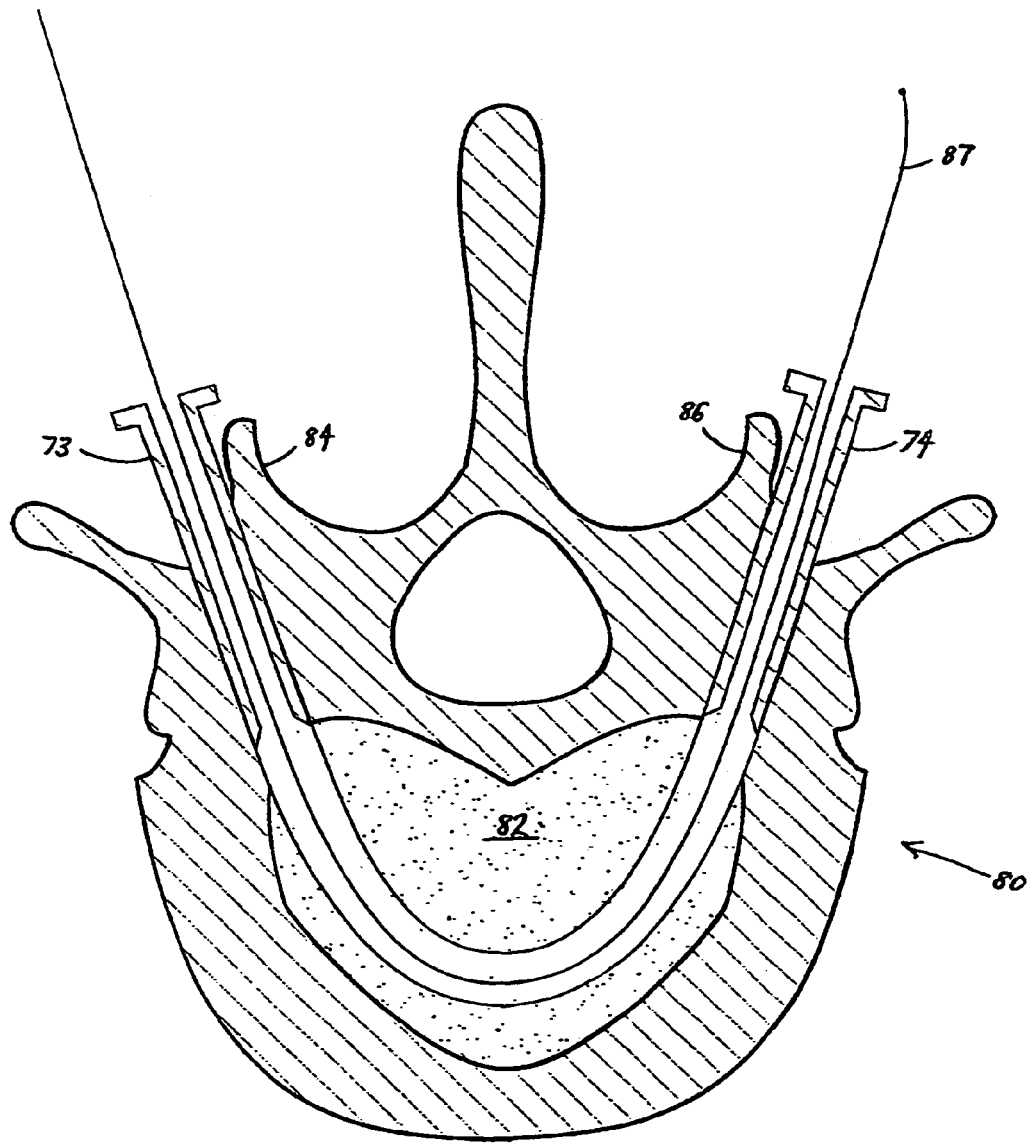
Figure 28D:
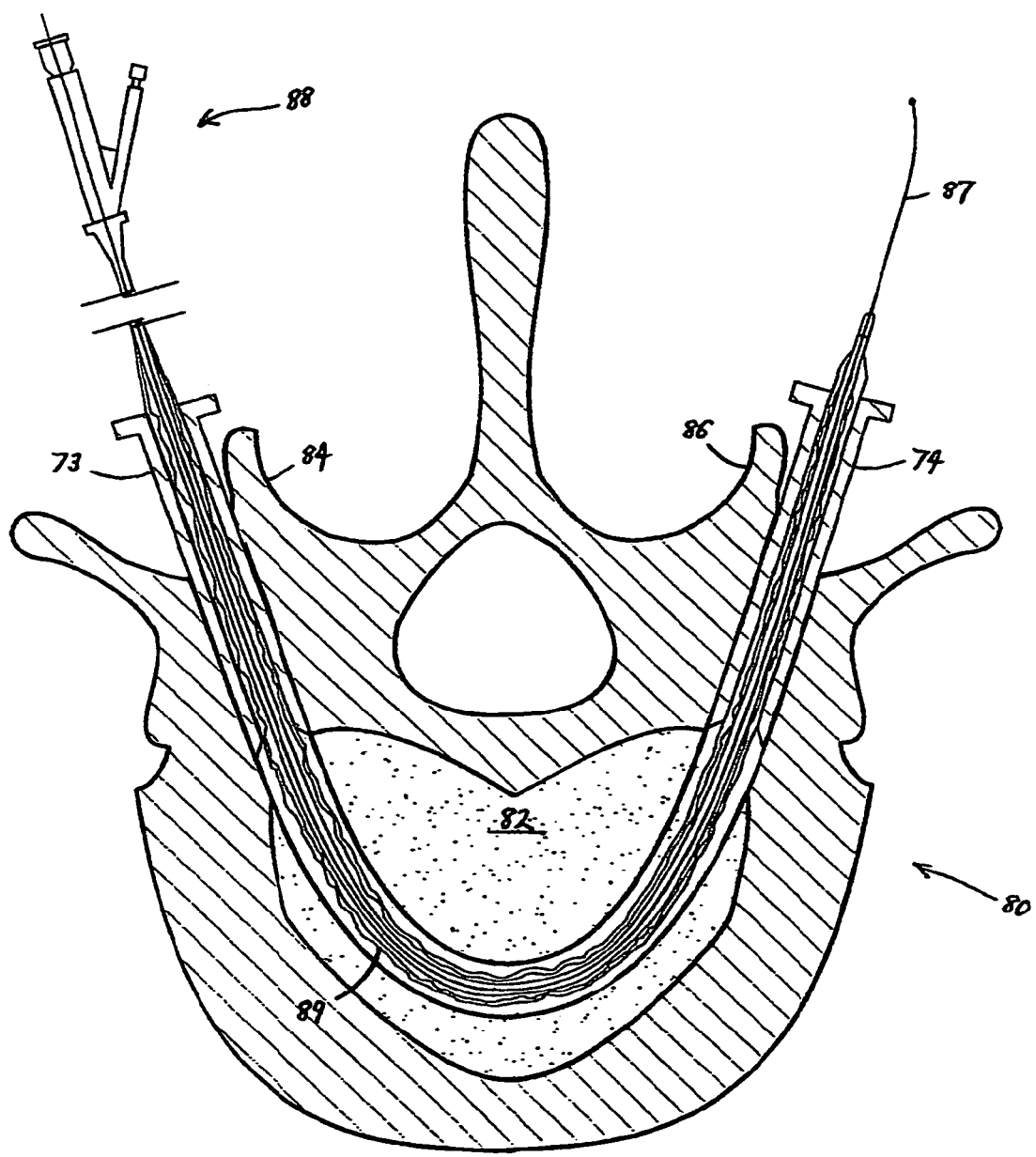

As shown in FIG. 28B, canula elements 73 and 74 are positioned respectively in the passages through left pedicle portion 84 and right pedicle portion 86. As seen in FIG. 28C, a guidewire 87 may then be positioned in the passageway through the vertebral segment 80. As seen in FIG. 28D, a catheter 88 in accordance with the present invention, having a balloon element 89, may then be positioned along guidewire 87 such that a middle portion of balloon element 89 is in interior region 82. Balloon element 89 is shown longer than the entire passageway through vertebral segment 80. As a result, when balloon element 89 is in place, a proximal-end portion of balloon element 89 extends completely through canula element 73 in left pedicle portion 84 and a distal-end portion of balloon element 89 extends completely through canula element 74 in right pedicle portion 86. In a variation of this embodiment, balloon element 89 may be fabricated so as to be pre-curved for easier placement and better fit when inflated inside the U-shaped channel.

Figure 28E:
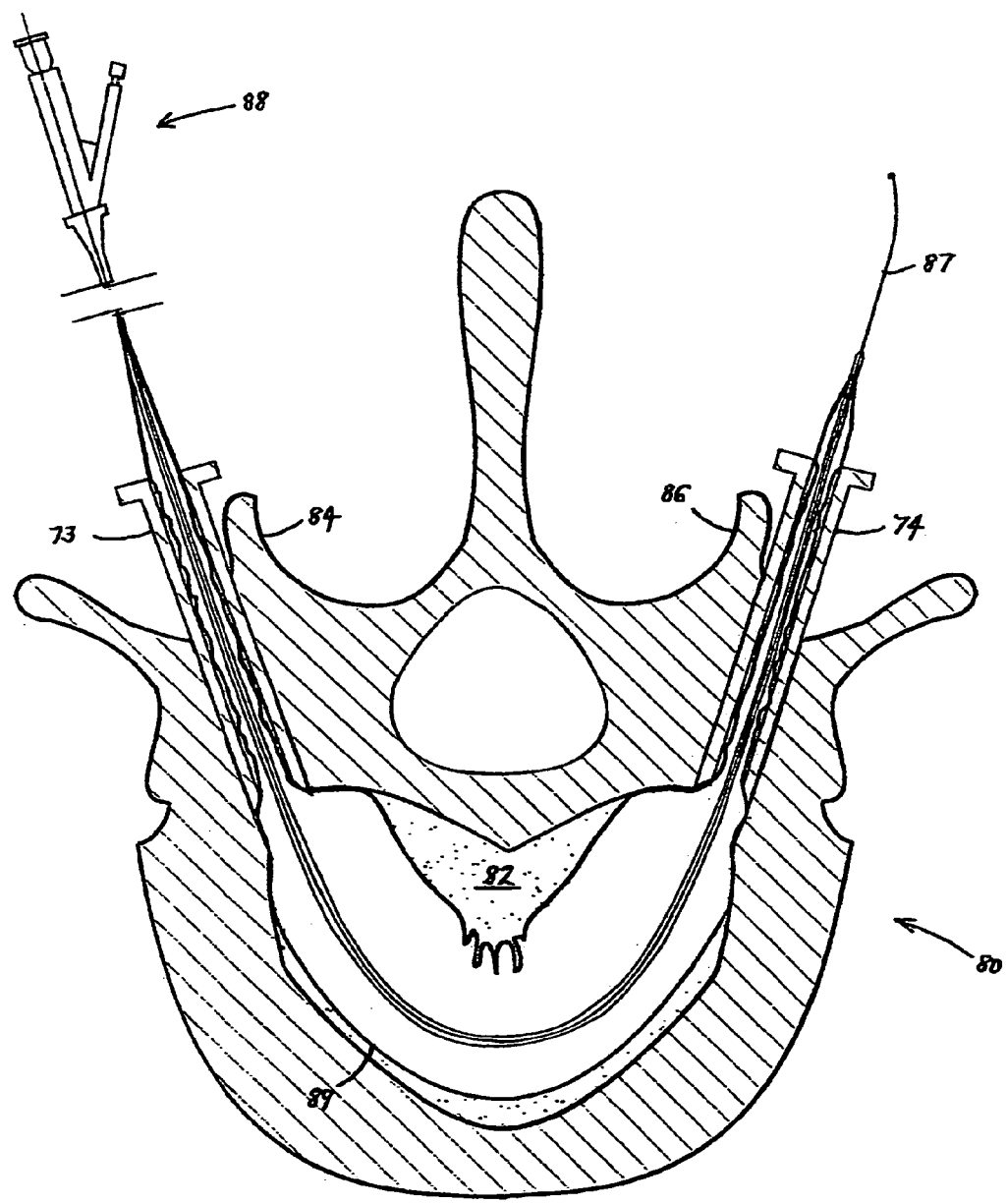

As seen in FIG. 28E, upon inflation of balloon element 89, only the middle portion inside interior region 82 can fully expand. As seen in FIG. 29, while balloon element 89 is in place and inflated, the proximal and distal ends of balloon element 89 are outside vertebral segment 80 and therefore accessible to the surgeon's hands 81 or to instruments.

FIG. 30 schematically illustrates a cross section of a vertebral segment 160 being treated with a catheter apparatus 162 which utilizes a pre-curved internal guidewire 163 but without a spring tensioning element according to another embodiment of the present invention. The pre-curved guidewire 163, fabricated for example from nitinol or other material having "memory" properties, assists in properly positioning the balloon element 169 in the preformed channel through the cancellous bone.

In one variation of this invention embodiment, balloon element 169 may be fabricated as a relatively thinner, more flexible balloon which can be fully inflated at relatively lower pressures inside vertebral segment 160. A more flexible balloon will have more uniform contact with the surrounding cancellous bone resulting in more surface area for expansion during inflation and the application of inflation forces at the interior locations where such forces are needed for expanding the bone mass.

In another variation of this invention embodiment, following a balloon inflation cycle, balloon element 169 can be deflated and guidewire 163 can be utilized similar to the push rods previously described for applying tension to the deflated balloon element to assist with removal through the small-diameter canula 165. If the balloon element 169 is of a thinner, more flexible construction than those previously described, less tensioning is required for removal. In addition, in the embodiment illustrated in FIG. 30, external tensioning can be applied to the distal end of the catheter, for example by simply pulling on the distal end, to assist in reducing the profile of the deflated balloon element for easier withdrawal. Alternatively or additionally, tensioning could be applied to the distal end of the catheter by twisting it.

In still another variation in accordance with this invention, balloon element 169 could be left in place in the interior of vertebral segment 160, and the cavity inside the balloon could be inflated and filled with cement for permanent support of the damaged vertebral element. During this procedure the push rod, if hollow, could be used as a vent tube that is removed after the balloon is filled with cement. The balloon walls would contain the liquid cement during the setting period thereby preventing leakage through bone fractures causing medical problems. Even after the cement is set, the balloon walls would prevent direct contact between the cement and the surrounding bone or tissue. For this embodiment, the long proximal neck of the balloon would be cut off after filling the balloon with cement and after removing the canula.

FIG. 31 schematically illustrates a pre-curved balloon element specially designed for use with a catheter apparatus according to this invention.

FIG. 32 schematically illustrates a cross section of a vertebral segment 170 being treated with a catheter apparatus 172 utilizing a pre-curved guidewire 173 according to another embodiment of the present invention.

FIG. 33 schematically illustrates a cross section of a vertebral segment 180 being treated with two catheter apparatuses 182 and 192 according to another embodiment of the present invention.

In still another embodiment of this invention, the catheter balloon element for expanding a damaged bone region may be a multi-lumen balloon as described in U.S. Pat. Nos. 5,342, 301 and 5,569,195, which patents are incorporated herein by reference. Use of a multi-lumen balloon can be of particular value where even using the spring tension or manual wrapping techniques described above will not allow production of a desired size and/or pressure balloon because the balloon profile is simply too large to fit in the canula.

Instead, by using a multi-lumen balloon, one can achieve both large diameters and higher pressures because each individual balloon can hold higher pressures with thinner walls. Even more important is that the cone or transition regions of the multi-lumen balloons are much thinner and much more flexible. For example, one could utilize a balloon element comprising four balloons/lumens with or without a central lumen for the shaft. Alternatively, with a 5-lumen multi-lumen balloon configuration, the shaft can pass through the central fifth lumen created by the four outside lumens or the shaft can pass through one of the four outside lumens.

As an alternative to a true multi-lumen catheter balloon construction, this embodiment of the invention could be practiced with many of the benefits of a multi-lumen balloon using several individual balloons in a side-by-side multiple balloon configuration. The individual balloons could be bonded together or, preferably, one could put an elastomeric or non-elastomeric sleeve over the group of individual balloons to keep them aligned during placement at the intended site, inflation and removal after the inflation cycle.

The multi-lumen and multiple balloon embodiments of this invention as described above may be practiced with straight balloons or with pre-curved balloons configured for easier placement and better fit inside a curved catheter access channel.

FIGS. 34A-34C illustrate yet another embodiment of the present invention. FIG. 34A is a schematic elevation view of a balloon dilatation apparatus 610 in some respects comparable to the balloon dilatation apparatus 210 of FIG. 10A. As best seen in the sectional view of FIG. 34B, this embodiment of the invention utilizes a stationary inner shaft or rod element 634 secured at its distal end to the tip 628 of inflation or balloon element 616 and a rotatable outer shaft 614. Rod element 634 runs through a central longitudinal channel in the catheter to the tip 628 of balloon element 616. Outer shaft 614 is connected at its distal end to inflation or balloon element 616 and at its proximal end to a rotatable sleeve element 612, which may advantageously include outward projections 615 to assist with manual rotation of the sleeve element and the connected outer shaft 614.

The proximal end of sleeve element 612 is designed with a lip portion 613 to receive and rotatably hold the distal end of a catheter inlet conduit 624 through which a fluid 640 can be introduced to inflate the balloon element 616. A gasket, seal, or O-ring 629, or a similar fluid-sealing element, having a centrally-located aperture, is seated between the end of conduit 624 and the lip portion 613 of sleeve element 612.

This embodiment of the present invention is especially useful in duct dilatation applications, for example in treating the lacrimal duct. In such applications, the inflation or balloon element 616 of apparatus 610 is positioned inside a duct that requires dilatation, for example to improve fluid drainage. Prior to insertion into the duct, the balloon element 616 can be tightly wrapped around the rod element 634 to reduce its profile and to facilitate insertion with minimal tissue damage or trauma. Once properly positioned, the balloon can be unwrapped by rotating sleeve element 612, for example using projections 615, either clockwise or counterclockwise as appropriate.

After it is positioned and unwrapped, balloon element 616 can be inflated with fluid 640 supplied from a pressurized fluid source through the hollow central channel running from the proximal end of inlet conduit 624 to the interior of the balloon element 616. The balloon element may be inflated to a desired size and/or a desired inflation pressure, depending on the elastic or inelastic nature of the balloon material, maintained fully inflated for a desired length of time, such as one to ten minutes, and then deflated by disconnecting the fluid source and/or withdrawing the fluid, for example by applying a vacuum. This inflation cycle may be repeated two or more times as appropriate for treating the duct dysfunction.

Following this medical procedure, the balloon or dilatation element is deflated and sleeve element 612 is again rotated either clockwise or counterclockwise in order to rewrap the deflated balloon element 616 tightly around rod element 634 to reduce its profile for removal from the duct. Projections 615 can be especially useful during this step to put additional twisting (rotational) forces on the deflated balloon element to obtain a tight wrap. Projections 615 can be held manually to maintain a tight wrap of the deflated balloon element or they can be used to secure this wrapped position such as with an elastic or other holding element. The rewrapped balloon element can then be relatively easily withdrawn from the duct with little or no trauma to surrounding tissue.

It will be apparent to those skilled in the art that other changes and modifications may be made in the above-described apparatus for adjustable epidermal tissue ingrowth cuffs and methods for using that apparatus without departing from the scope of the invention herein, and it is intended that all matter contained in the above description shall be interpreted in an illustrative and not a limiting sense.

Having described my invention, what We claim is:

1. An assembly with proximal and distal ends for bone, tissue and/or duct dilatation of a living being comprising in combination:
    (a) an inflatable and deflatable balloon element having a balloon interior;
    (b) a conduit defining a channel for accessing the balloon interior from a location outside a living body when the balloon is positioned inside the living body;
    (c) a balloon tensioning and/or balloon wrapping device for stretching the balloon element and/or folding, pleating or wrapping the balloon element to facilitate insertion and/or removal of the balloon element through a narrow diameter duct, access channel or cannula, the device comprising a rod having proximal and distal ends and extending through the channel to or into the balloon element at the distal end of the rod in combination with a spring adjacent the proximal end of the rod, whereby compression of the spring applies an axial force to the rod tending to move it in a distal direction so as to apply axial tensioning to the balloon element; and,
    (d) a rotatable cap at the proximal end of the assembly whereby rotating the cap in a first direction compresses the spring and rotating the cap in a second direction decompresses the spring.

2. An assembly according to claim 1 wherein active and/or passive forces can be applied to the rod for tensioning and/or wrapping the balloon element.

3. An assembly according to claim 1 wherein the distal end of the balloon element is sealed, and the rod extends to the sealed distal end of the balloon element.

4. An assembly according to claim 3 wherein the cap can be rotated manually or automatically to compress the spring and push the rod against the sealed distal end of the balloon element causing tension and axial elongation of the balloon element.

5. An assembly according to claim 1 wherein the rod is not attached to the balloon element.

6. An assembly according to claim 1 wherein the rod is attached to or otherwise engages the balloon element.

7. An assembly according to claim 1 further wherein compression of the spring also applies rotational force to rotate the rod from its free-standing position causing the balloon element at least in part to wrap around the rod.

8. An assembly according to claim 1 wherein the spring has been at least partly compressed and said rod has been moved in a distal direction causing axial tensioning and elongation of the balloon element.

9. An assembly according to claim 1 wherein the spring has been at least partly compressed and said rod has been rotated causing wrapping and rotational tensioning of the balloon element.

10. An assembly according to claim 1 wherein the spring has been at least partly compressed and said rod has been moved in a distal direction and rotated causing both axial and rotational tensioning of the balloon element.

11. An assembly according to claim 1 further comprising a disc element between the distal end of the spring and the proximal end of the rod.

12. An assembly according to claim 1 wherein the proximal end of the assembly comprises a hollow tube portion housing the spring.

13. An assembly according to claim 1 wherein the balloon tensioning and/or wrapping device is hydraulically or pneumatically actuated.

14. An assembly according to claim 1 wherein said rod is adjustable in length.

15. An assembly according to claim 1 further comprising at least a cannula element wherein at least one end of the balloon element extends into or completely through said cannula element when the balloon element is positioned in a cavity to be dilated.

16. An assembly according to claim 1 wherein said rod is spring loaded to apply axial tensioning to the balloon element and is also adapted for rotational tensioning of the balloon element.

17. A dilatation apparatus able to fit through a narrow opening, said dilatation apparatus comprising an inflatable balloon element at a distal apparatus end in fluid communication with a hollow tube, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus.

18. A dilatation apparatus according to claim 17 wherein said balloon element is stretched and/or folded, pleated or wrapped to a diameter of about 4-5 mm or less.

19. A dilatation apparatus according to claim 17 wherein the distal end of the balloon element is sealed.

20. A dilatation apparatus according to claim 19 wherein the rod element is attached to or otherwise engages the balloon element.

21. A dilatation apparatus according to claim 20 further wherein the balloon element is at least in part wrapped around the rod element.

22. A dilatation apparatus according to claim 20 wherein said rod element is applying rotational tensioning to the balloon element.

23. A dilatation apparatus according to claim 17 further comprising a hydraulic or pneumatic spring actuation system.

24. A dilatation apparatus according to claim 17 wherein said rod element is adjustable in length.

25. A dilatation apparatus able to fit through a narrow opening, said dilatation apparatus comprising an inflatable balloon element at a distal apparatus end in fluid communication with a hollow tube, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus, and also wherein the distal end of the balloon element is sealed and the rod element is not attached to the balloon element.

26. A dilatation apparatus able to fit through a narrow opening, said dilatation apparatus comprising an inflatable balloon element at a distal apparatus end in fluid communication with a hollow tube, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus, and also wherein said rod element is spring loaded to automatically apply axial tensioning to the balloon element during a balloon deflation.

27. A dilatation apparatus able to fit through a narrow opening, said dilatation apparatus comprising an inflatable balloon element at a distal apparatus end in fluid communication with a hollow tube, and a rod element spring loaded at a proximal apparatus end running through the interior of the hollow tube and the inflatable balloon element, wherein said balloon element is inflated and is wrapped, folded, pleated or stretched at least in part about said rod element to reduce the profile of the balloon portion of the dilatation apparatus, and also wherein said rod element comprises concentric inner and outer tubular members.

28. A dilatation apparatus able to fit through a narrow opening, said dilatation apparatus comprising an inflatable balloon element at a distal apparatus end in fluid communication with a hollow tube, and a rod element spring loaded at a proximal apparatus end running through the interior of the hollow tube and the inflatable balloon element, wherein said balloon element is uninflated and is wrapped, folded, pleated or stretched at least in part about said rod element to reduce the profile of the balloon portion of the dilatation apparatus, and also wherein a cannula element threadably engages external threads along a portion of the dilatation apparatus such that the cannula annularly surrounds a portion of the balloon element.

29. A dilatation apparatus having the following configuration: a proximal end catheter sleeve portion, a middle sleeve portion, and a balloon or inflation element at or near the distal end of the catheter; the proximal end catheter sleeve portion comprises a branched or Y-shaped element, of which a first arm or branch comprises a tubular shell with external threads at its proximal end and a spring inside the tubular shell, and a second arm or branch comprises a fluid inlet/outlet conduit for introducing pressurized fluid into the catheter for inflating the balloon or for withdrawing fluid after a dilatation procedure; the tubular shell of the first branch comprises a region adjacent to the threaded region for housing the spring; a cap element with internal threads sized to mate with the external threads at the proximal end of the first branch engages the proximal end of the first branch; at the distal end of the region housing the spring element, a disc element or circular fitting is sized to slide inside the region housing the spring element so as to compress the spring element by displacement in the proximal direction or to decompress the spring element by displacement in the distal direction; associated with the disc element is an axially moveable rod element which runs axially through the interior of the catheter from the distal side of the disc element to a sealed tip portion of the balloon and thus can act like a piston to alternately compress and allow decompression of the spring element.

30. A medical dilatation apparatus having proximal and distal ends and adapted to fit through a narrow opening into a body location, said dilatation apparatus comprising an inflatable balloon having a balloon interior in fluid communication with a hollow tube, a rod element running through the interiors of the hollow tube and the inflatable balloon, and a spring element which, when compressed, applies axial and/or rotational forces to the balloon by means of the rod element, said spring element being housed in a spring housing section located at the proximal end of the apparatus, wherein said balloon is initially uninflated and is wrapped, folded, pleated or stretched at least in part about said rod element to reduce the profile of the balloon portion of the dilatation apparatus.

* * * * *